(12) United States Patent
Bellemare et al.

(10) Patent No.: US 9,933,346 B2
(45) Date of Patent: Apr. 3, 2018

(54) CONTACT MECHANIC TESTS USING STYLUS ALIGNMENT TO PROBE MATERIAL PROPERTIES

(71) Applicant: Massachusetts Materials Technologies LLC, Cambridge, MA (US)

(72) Inventors: Simon C. Bellemare, Weston, MA (US); Steven D. Palkovic, Somerville, MA (US); Phillip A. Soucy, Chelmsford, MA (US); Michael J. Tarkanian, West Roxbury, MA (US); Brendon M. Willey, Dedham, MA (US)

(73) Assignee: Massachusetts Materials Technologies LLC, Cambridge, MA (US)

( * ) Notice: Subject to any disclaimer, the term of this patent is extended or adjusted under 35 U.S.C. 154(b) by 0 days.

(21) Appl. No.: 15/256,276

(22) Filed: Sep. 2, 2016

(65) Prior Publication Data

US 2016/0370272 A1    Dec. 22, 2016

Related U.S. Application Data

(63) Continuation-in-part of application No. 14/310,611, filed on Jun. 20, 2014, now Pat. No. 9,778,158, and
(Continued)

(51) Int. Cl.
*G01N 3/46* (2006.01)
*G06F 17/50* (2006.01)
*G01N 3/60* (2006.01)

(52) U.S. Cl.
CPC .............. *G01N 3/46* (2013.01); *G01N 3/60* (2013.01); *G06F 17/5018* (2013.01); *G01N 2203/0032* (2013.01); *G01N 2203/06* (2013.01)

(58) Field of Classification Search
CPC ........ G01N 3/46; G01N 3/60; G01N 2203/06; G01N 2203/0032
See application file for complete search history.

(56) References Cited

U.S. PATENT DOCUMENTS

| | | | |
|---|---|---|---|
| 5,866,807 A | * | 2/1999 | Elings ................. G01N 3/46 73/105 |
| 6,520,004 B1 | | 2/2003 | Lin |

(Continued)

FOREIGN PATENT DOCUMENTS

| | | |
|---|---|---|
| JP | 2002506221 A | 2/2002 |
| WO | 0216907 A1 | 2/2002 |

OTHER PUBLICATIONS

European Patent Office, Extended European Search Report—Application No. 14814061.9 dated Jan. 30, 2017, 8 pages.
(Continued)

*Primary Examiner* — Ryan Walsh
(74) *Attorney, Agent, or Firm* — Sunstein Kann Murphy & Timbers LLP

(57) ABSTRACT

An apparatus for performing a contact mechanics test on a substrate includes a stylus, a core configured to engage the stylus against the substrate, a stylus engagement mechanism configured to induce a contact load or a penetration depth to the stylus, a core engagement mechanism configured to maintain contact of the core and to move the core along the substrate surface, a frame configured to be fixed with respect to the apparatus or to be moved together with the core engagement mechanism as an assembly, a frame engagement mechanism configured to engage the frame with the substrate surface; and a substrate monitoring device configured to measure characteristics of substrate contact response and/or collect material machined from the substrate. Methods of performing a contact mechanics test are also provided.

25 Claims, 74 Drawing Sheets

Related U.S. Application Data a continuation-in-part of application No. 15/061,415, filed on Mar. 4, 2016.

(60) Provisional application No. 61/837,724, filed on Jun. 21, 2013, provisional application No. 62/270,416, filed on Dec. 21, 2015, provisional application No. 62/237,950, filed on Oct. 6, 2015, provisional application No. 62/128,753, filed on Mar. 5, 2015.

(56) References Cited

U.S. PATENT DOCUMENTS

| | | | |
|---|---|---|---|
| 7,685,868 B2* | 3/2010 | Woirgard | G01N 3/42 73/81 |
| 2004/0011119 A1 | 1/2004 | Jardret et al. | |
| 2006/0150710 A1 | 7/2006 | Moyse et al. | |
| 2006/0174699 A1 | 8/2006 | Hicks et al. | |
| 2007/0227236 A1 | 10/2007 | Bonilla et al. | |
| 2008/0028840 A1* | 2/2008 | Smith | G01N 3/42 73/81 |
| 2009/0145208 A1 | 6/2009 | Coudert et al. | |
| 2014/0373608 A1 | 12/2014 | Bellemare et al. | |
| 2016/0258852 A1 | 9/2016 | Bellemare et al. | |

OTHER PUBLICATIONS

International Searching Authority, International Search Report—International Application No. PCT/US2014/043498, dated Aug. Oct. 16, 2014, together with the Written Opinion of the International Searching Authority, 17 pages.

* cited by examiner

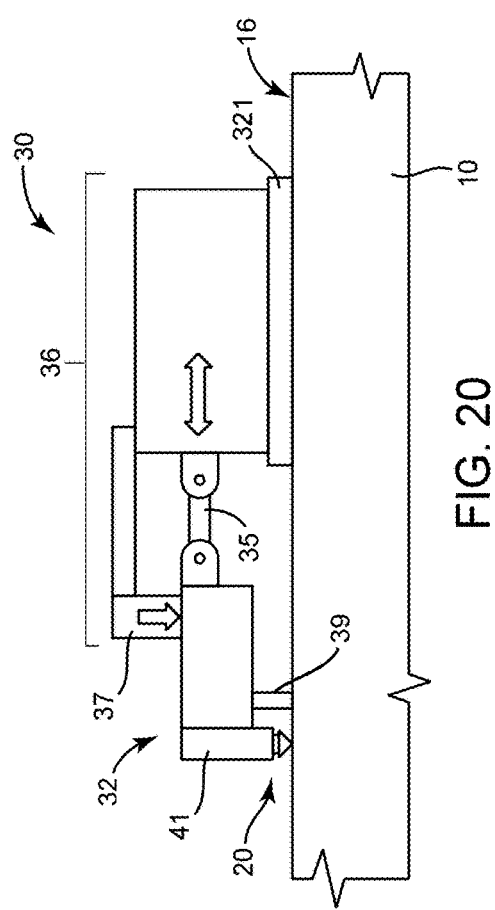
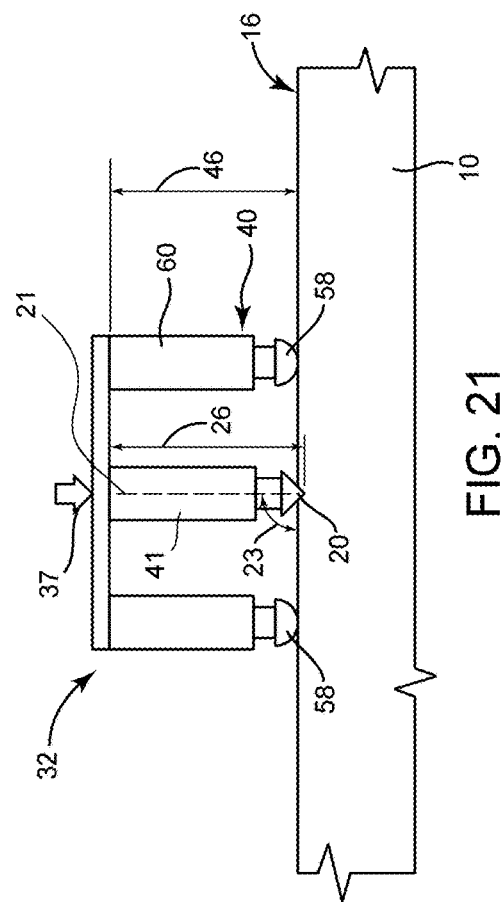

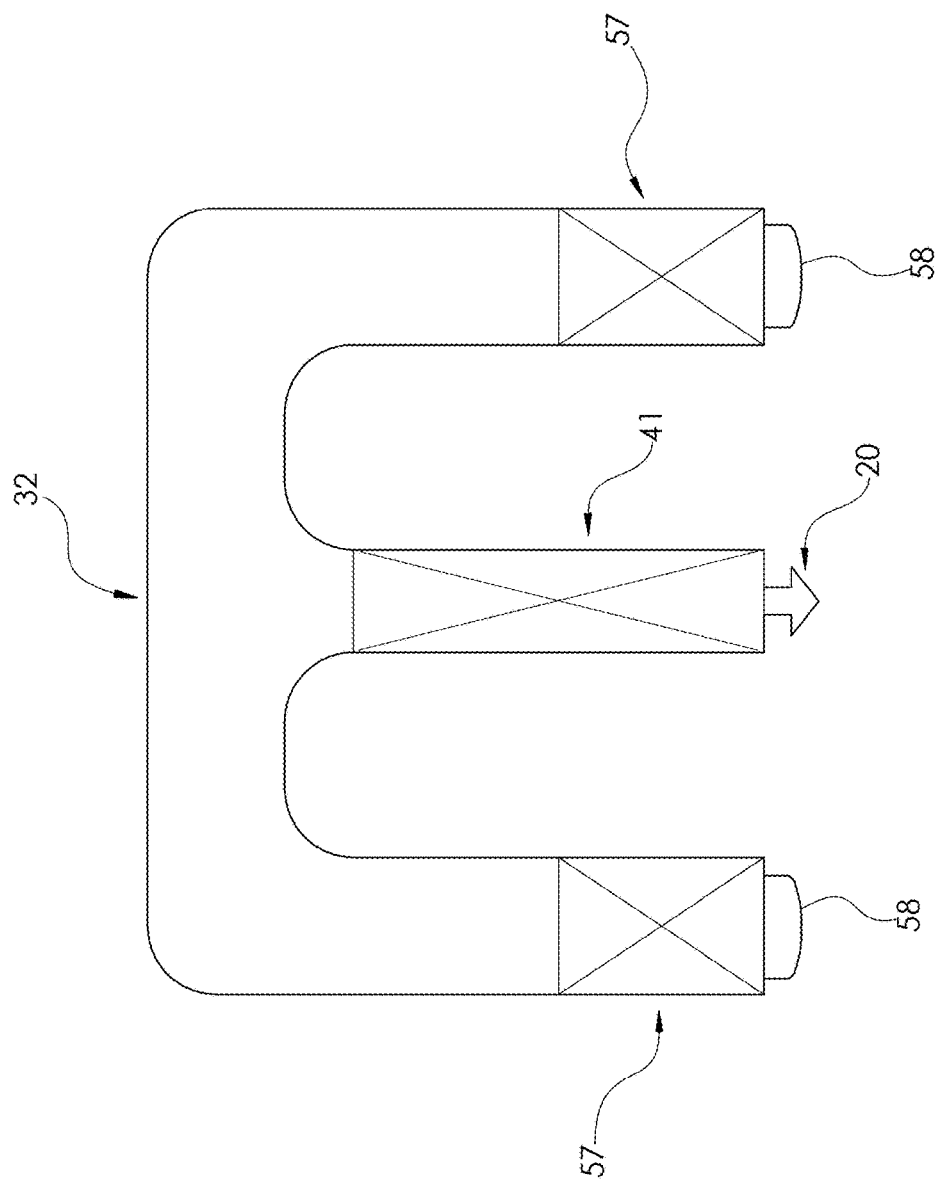

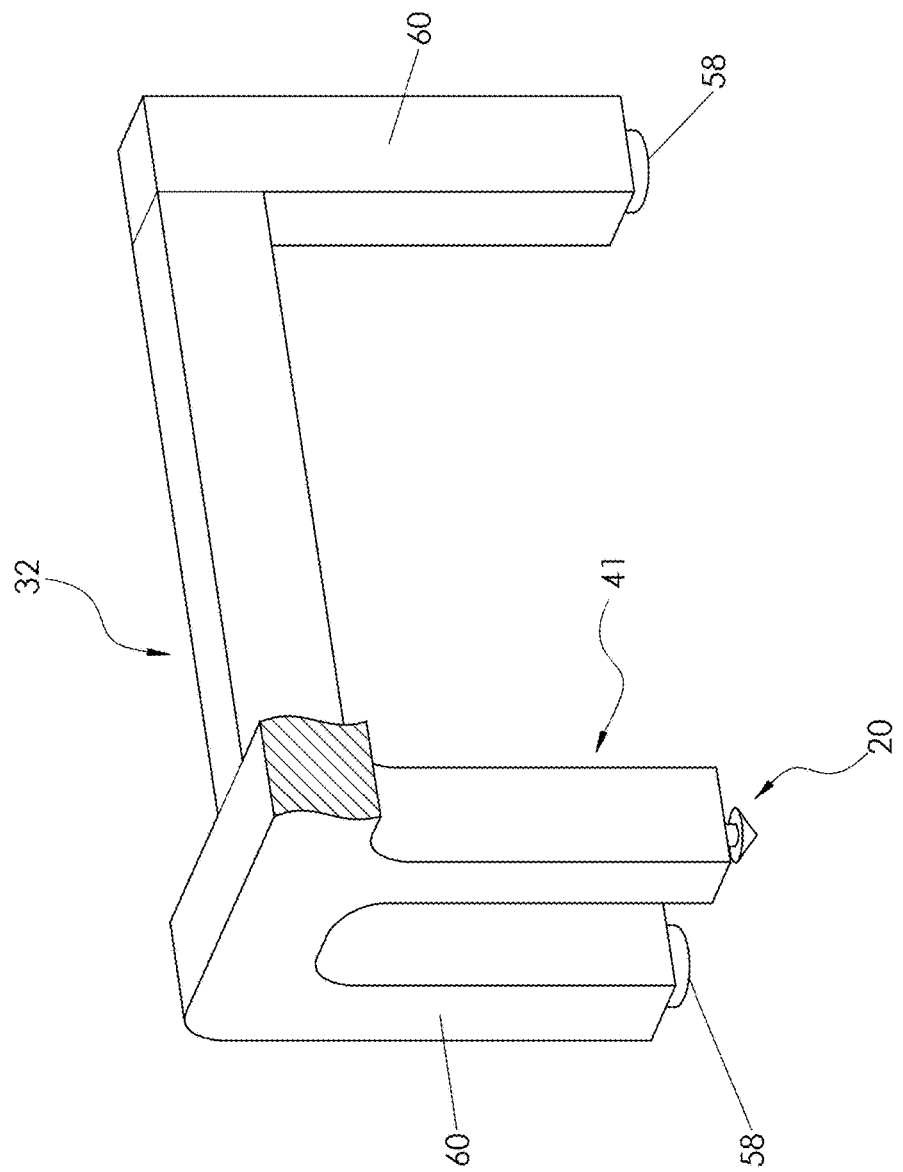

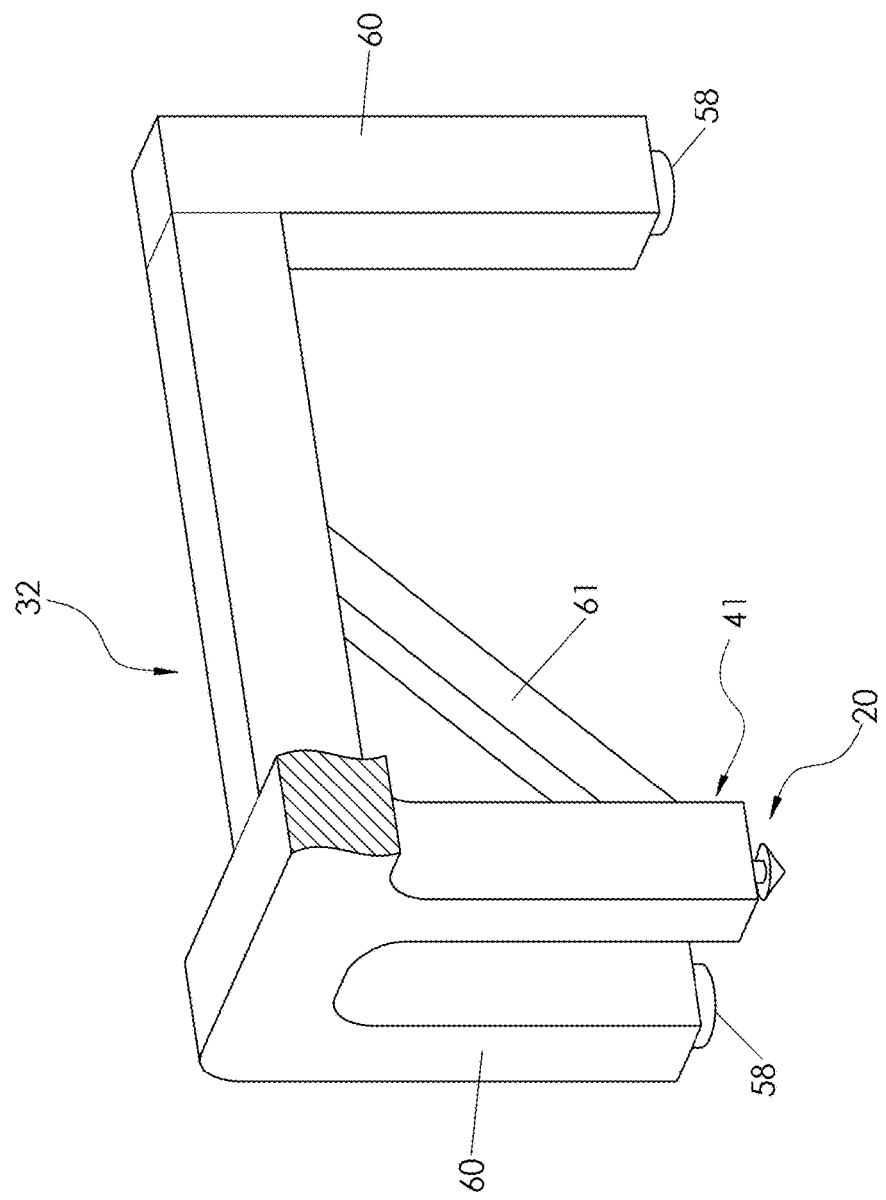

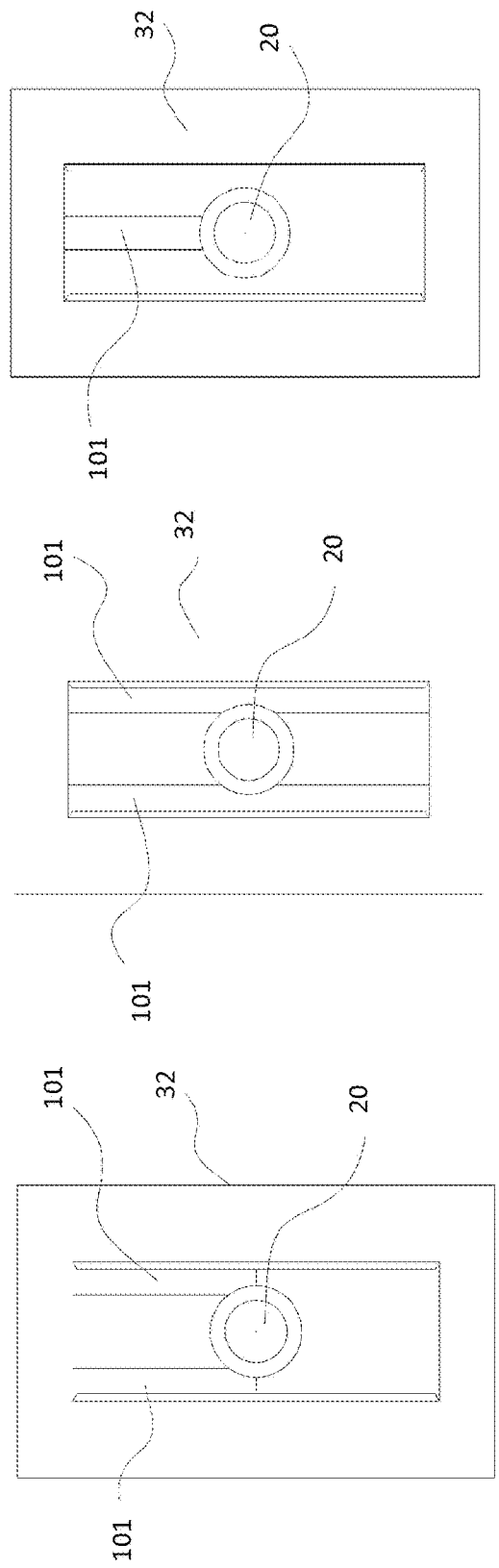

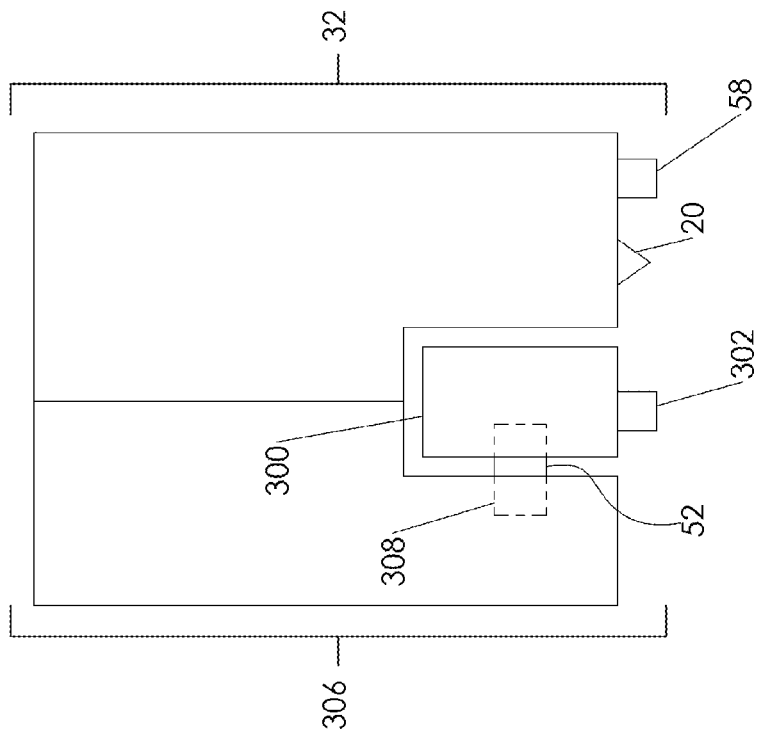
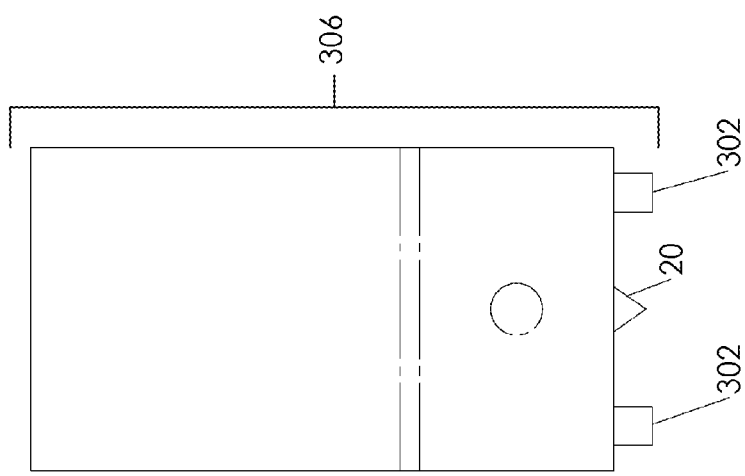
FIG. 30B
FIG. 30A

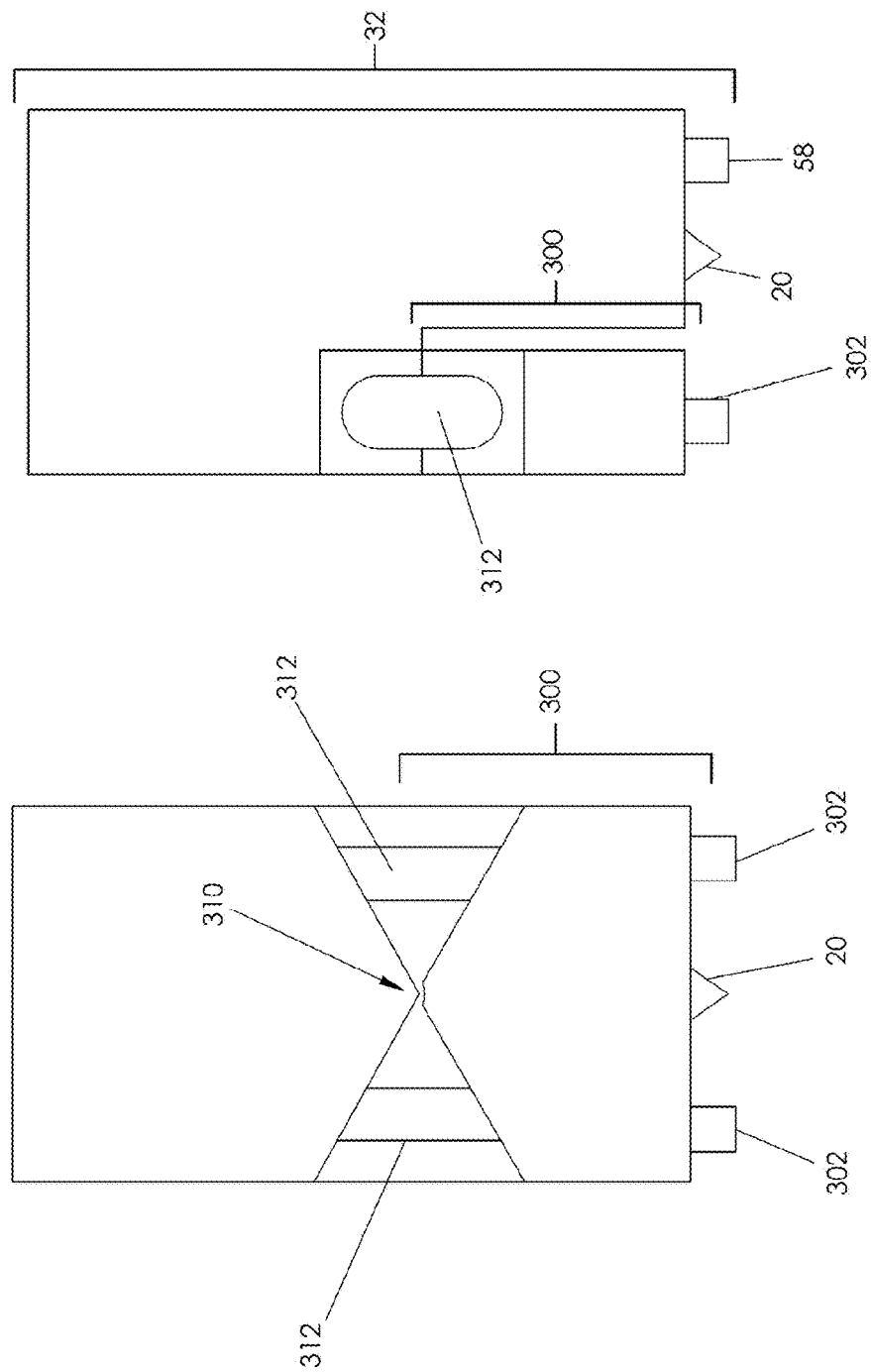

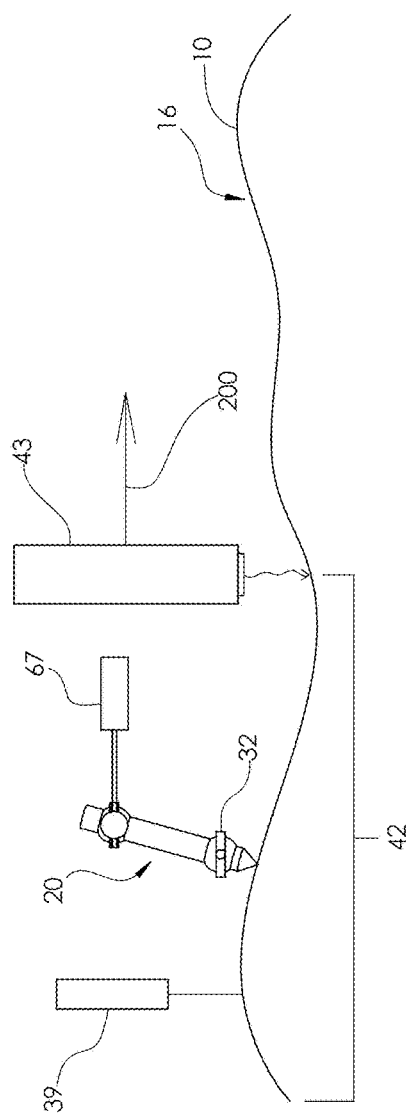
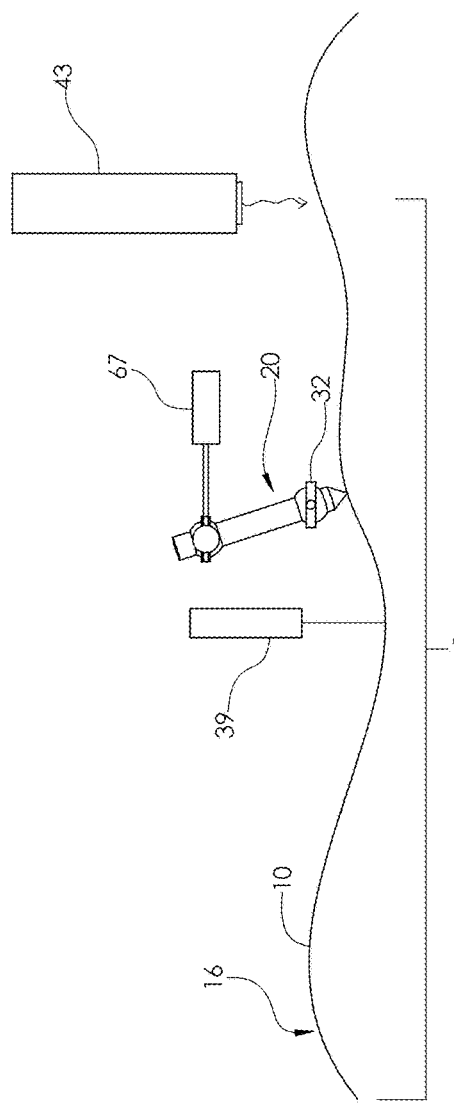
FIG. 34A
FIG. 34B

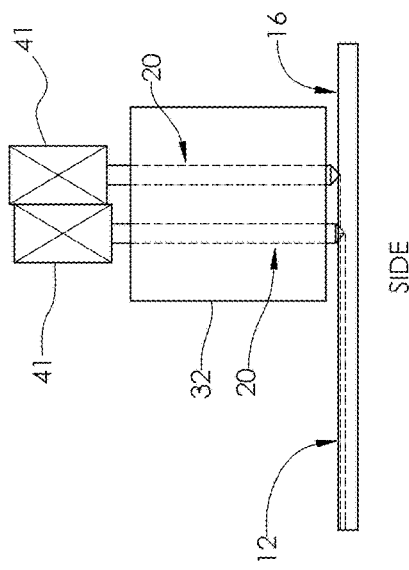
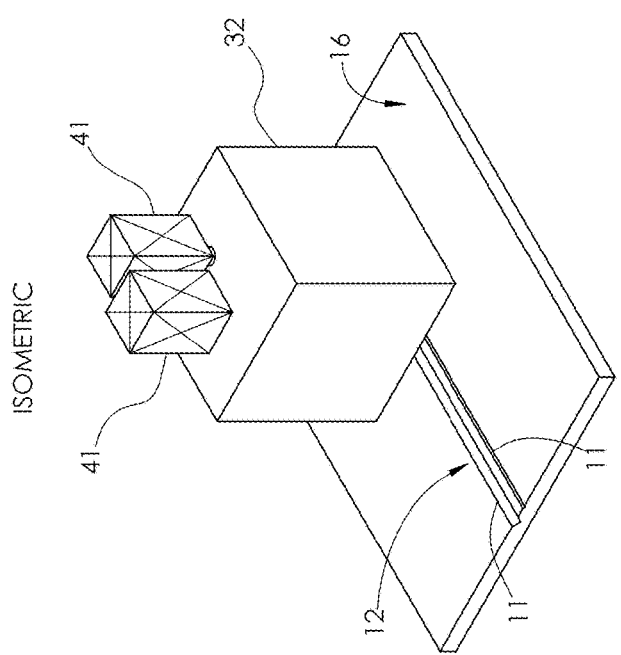
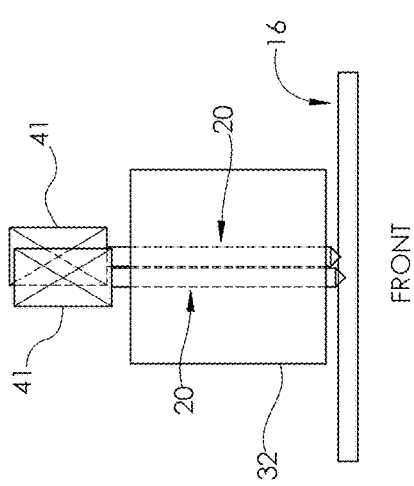
FIG. 35A
FIG. 35B
FIG. 35C

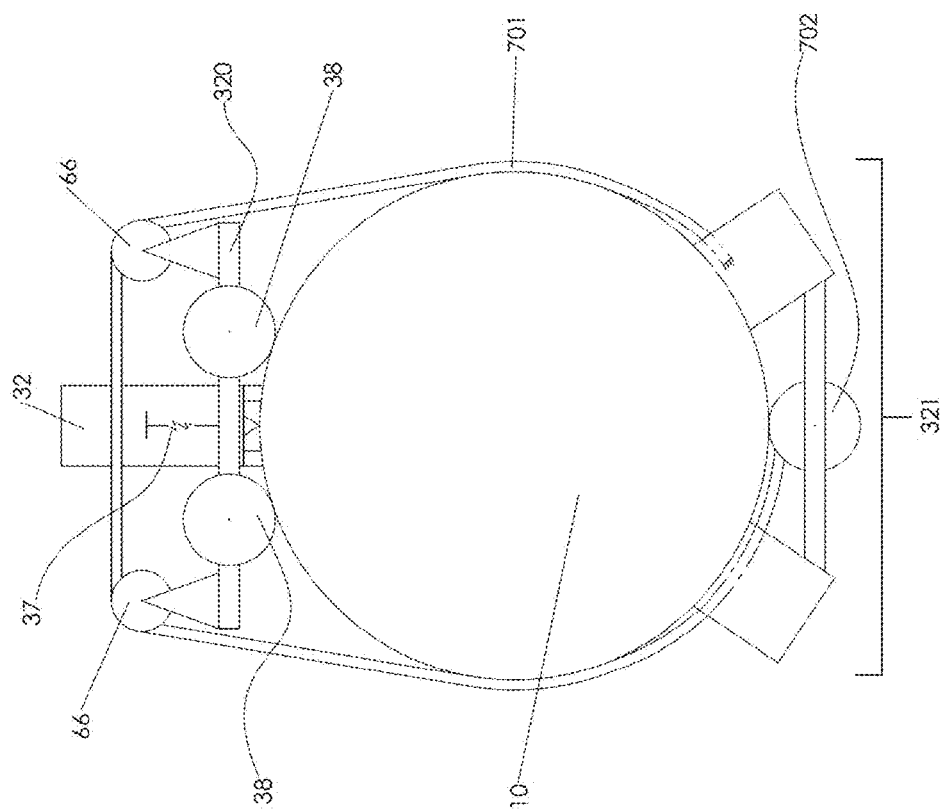

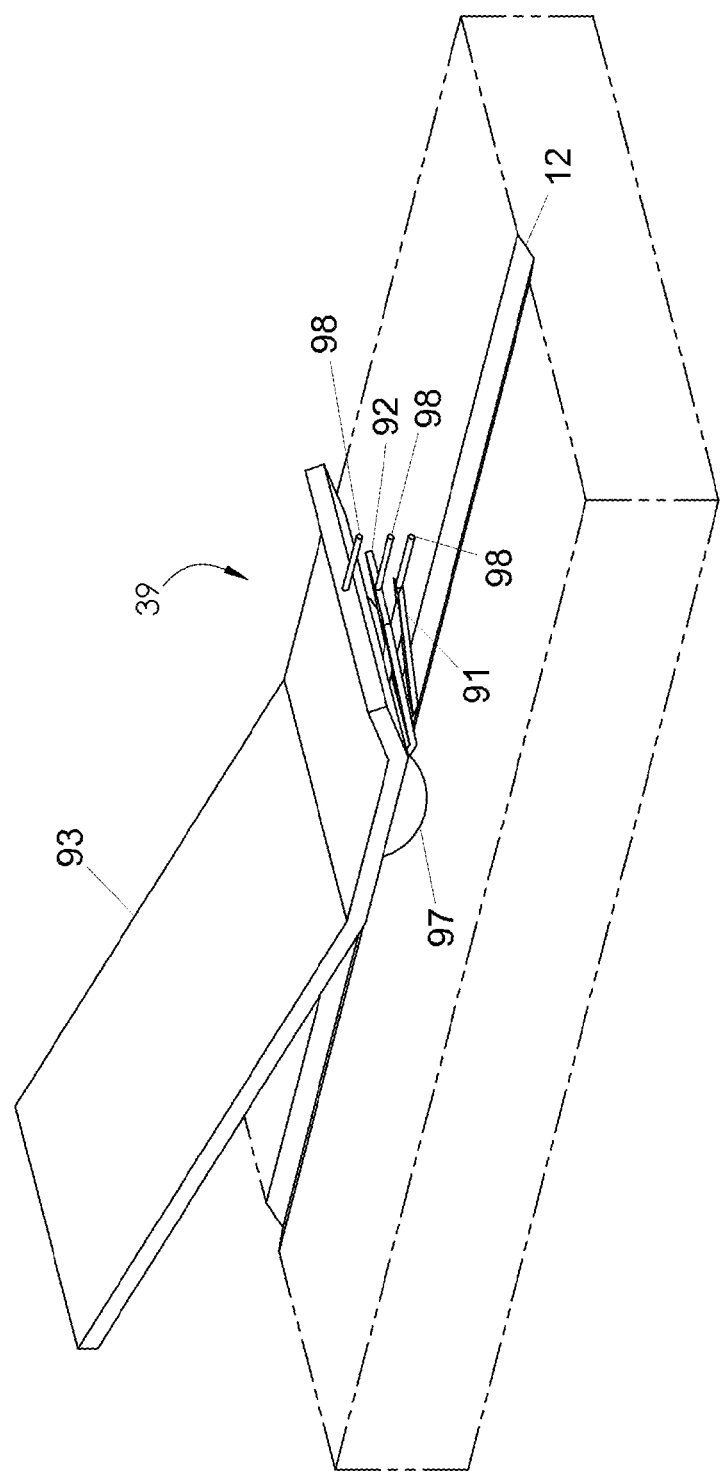

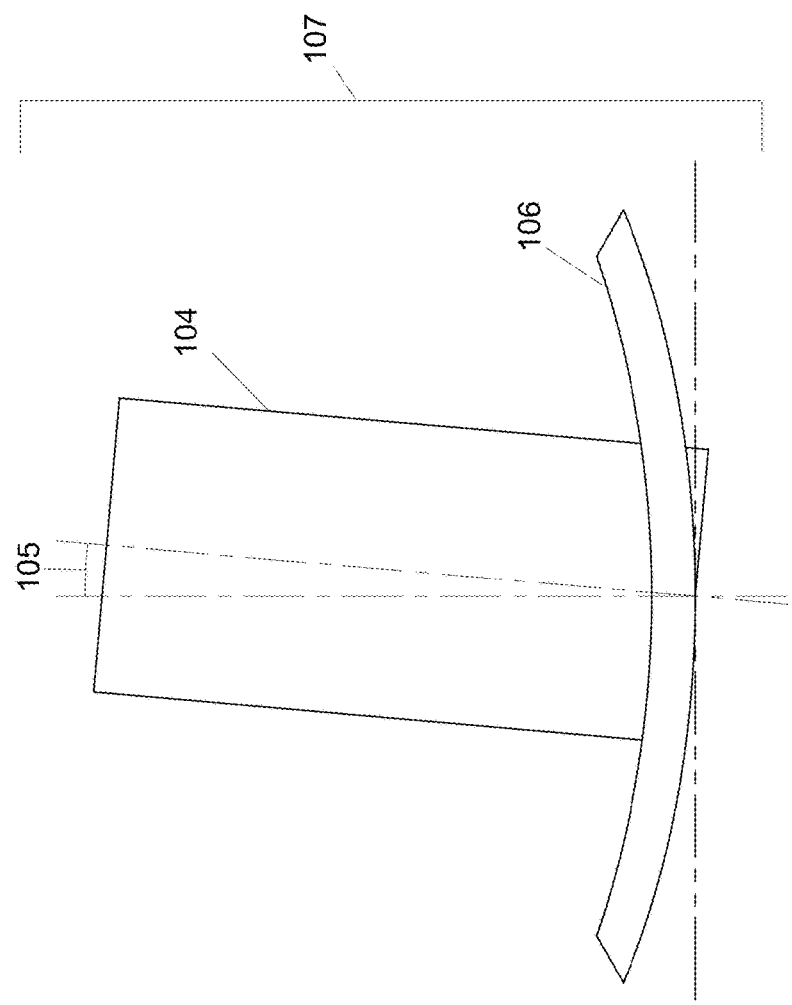

CONTACT MECHANIC TESTS USING STYLUS ALIGNMENT TO PROBE MATERIAL PROPERTIES

CROSS REFERENCE TO RELATED APPLICATIONS

The present application is a continuation-in-part application of U.S. patent application Ser. No. 15/061,415, filed Mar. 4, 2016, which claims the benefit of U.S. Provisional Patent Application No. 62/128,753 filed Mar. 5, 2015, U.S. Provisional Patent Application No. 62/237,950 filed Oct. 6, 2015, and U.S. Provisional Patent Application No. 62/270,416 filed Dec. 21, 2015. The present application is also a continuation-in-part application of U.S. patent application Ser. No. 14/310,611, filed Jun. 20, 2014, which claims the benefit of U.S. Provisional Patent Application No. 61/837,724 filed Jun. 21, 2013. The disclosures of the above applications are incorporated by reference herein in their entirety.

TECHNICAL FIELD

The present invention relates to the use of contact mechanics to gain data and information related to material state and properties, and more specifically to the sampling of material surface characteristics, including mechanical behavior, without requiring the use of conventional cutting or machining tools to remove a large sample from an existing structure, component or product.

BACKGROUND ART

Engineers and other decision-making agents utilize data about the materials of fabrication of load bearing structures to determine their durability, reliability and the overall safety. The data can be from a number of sources including the original manufacturing specifications, from manufacturing quality control, or from measurements done after the fact as part of condition assessment. Non-destructive testing (NDT) methods are appealing because they allow for estimating the characteristics and properties of assemblies and structures without damaging or jeopardizing the function of the structure during testing.

Non-destructive testing during condition assessment on existing structures in the field is very important to safety and the protection of the environment. We have a large inventory of existing infrastructures that may have changed from the time they were originally manufactured as well as existing infrastructures that would not meet the current standards of design and fabrication. One goal with condition assessment is to minimize the risk of a catastrophic event such as the break of a large oil or gas pipeline, the collapse of a bridge or the failure of a large pressure vessel. These events still occur too frequently in our society.

Non-destructive testing can be used to evaluate, among others, the existence and size of cracks, changes in material thickness for corrosion, and the properties of the materials. Properties of the materials that can be of interest include the chemistry, mechanical properties and the cracking resistance under the service environment and/or the cyclic loads.

Current industrial non-destructive techniques for mechanical properties can be limited in scope to measuring the hardness of a material by indentation, which provides an index of a material's resistance to penetration by a hard indentor or stylus. Although indentation testing is widely used, the traditional equipment provides a hardness value which is not a reliable measure of mechanical properties such as yield strength or ultimate strength, and provides no measure of ductility. A recent variation of the indentation hardness test uses a series of spherical indentations of progressively increasing depth at the same material location to provide an estimate of the stress-strain curve of the material. This technique requires generating multiple indents in each region of the structure where an estimate of the material properties is desired. Therefore, these series of indents have limitations with respect to the study of microstructural gradients, such as changes in properties through welds and surface modifications. This apparatus and method are detailed in U.S. Pat. No. 6,945,097 B2 dated 20 Sep. 2005. Another variation is instrumented indentation, whereby the reaction force on the stylus and its relative displacement is monitored during a loading and unloading cycle. The load-displacement information is then used to predict material hardness and elastic stiffness as described in Oliver and Pharr's 1992 paper, "An improved technique for determining hardness and elastic modulus using load and displacement sensing indentation techniques." More recently, Dao et al. utilized the load-displacement information along with numerical models to develop predictive algorithms for determining the complete stress-strain curve.

It is known in the prior art to use a hard indentor or stylus to deform materials by applying a vertical force and displacement and inducing a lateral movement of the indentor or stylus. These tests are often called scratch, or contact mechanics experiments. They introduce material and geometrical changes to the substrate surface. Contact mechanics tests have been used for material characterization throughout history, including in 1812 with the publishing and later broad adoption of the Mohs scale of mineral hardness. Over the past decades, advances in instrumentation to perform contact mechanic experiments have helped to elevate the amount of information that can be obtained through contact mechanics experiments. A number of test apparatus and methods have been developed and disclosed. However, the apparatus and techniques known to the inventors assume that the substrate can be brought at a desired angle with respect to the stylus.

Currently, contact mechanics tests are used to measure the strength of thin-films and coatings. This test is done by using a hard stylus to engage with the material while moving the stylus along the material's surface and controlling the load being applied to the stylus until failure occurs. This testing method is described in U.S. patent application Ser. No. 10/362,605, and is limited to select applications where materials utilize thin-films or coatings. This restriction makes the technology unsuited for assessing mechanical properties of common engineering materials. In addition to coating strength, recent academic research by A. T. Akono et al. has used contact mechanics tests in an attempt to correlate with the fracture toughness of materials. The implementation assumes that the crack forms at the apex of the stylus in-front of the direction of sliding. Contact mechanics tests have also been utilized to predict the yield strength and ductility of metals through the use of numerical modeling and dimensional analysis. All of these contact mechanics methods utilize existing laboratory testing devices and systems, but the underlying test apparatus is either too complex or not sufficiently accurate for broad commercial use. As a result, existing testing systems provide only partial solutions for evaluating mechanical properties.

Based on the above, contact mechanics experiments are not performed in the field or in industrial facilities as much as they could be if the capabilities were improved. Field testing solutions have been developed using indentation techniques. Examples include the King Portable Brinell Tester, Telebrinell Tester, Shear Pin Brinell Tester, Leeb (or rebound) Tester, and Automated Ball Indentation (ABI) Tester. These field devices use various methods of aligning the system with the structure being tested. Each method, however, requires the use of contact points that remain stationary. As a result, the devices must be connected and disconnected for each individual test location, or alignment of the devices is not maintained. Furthermore, these indentation testers provide limited information about the ductility of the material, especially within the heat affected zone of welded joints. Indentation testing also typically provides limited information with respect to the cracking resistance and toughness of the material under service conditions. The ductility of a material is an indication of how it will stretch or deform permanently before it breaks. The alternative solution for evaluating existing structures in the field is material removal for laboratory testing, which requires repair and limits the number of locations that can be tested without jeopardizing the integrity of the structure.

In some instances, the surface properties of the material that is measured through contact mechanics may not be representative of the bulk behavior. This is because gradients in properties may exist due to prior fabrication and manufacturing processes. These processes include heat treatments, cold forming, hot rolling, shot-peening, and others. There are currently no existing methods to systematically account for these gradients in mechanical properties, and therefore contact mechanics tests are only applicable for the small volume of material that is directly probed.

SUMMARY OF THE EMBODIMENTS

In one embodiment of the invention, an apparatus for performing a contact mechanics test on a substrate, the apparatus comprising (i) a stylus having a principal axis and shaped to deform the substrate at a stylus contact location, (ii) a core, in which the stylus is hosted, configured to engage the stylus against the substrate, (iii) a stylus engagement mechanism, coupled to the core or the stylus, configured to induce a contact load or a penetration depth to the stylus, (iv) a core engagement mechanism, coupled to the core, configured to maintain contact of the core and to move the core along the substrate surface, (v) a frame, in which the core engagement mechanism is hosted, configured to be fixed with respect to the apparatus or to be moved together with the core engagement mechanism as an assembly, (vi) a frame engagement mechanism configured to engage the frame with the substrate surface, and (vii) a substrate monitoring device configured to measure characteristics of substrate contact response, collect material machined from the substrate, or both. In this embodiment, the core, the core engagement mechanism or the frame engagement mechanism includes an alignment mechanism configured to provide a desired local angular orientation of the principal axis of the stylus relative to the substrate surface at the stylus contact location. In another embodiment of the invention, a method for performing a contact mechanics test on a substrate surface using one or more styluses, each stylus having a principal axis and shaped to deform the substrate surface, the method comprising (i) maintaining the principal axis of the stylus at a desired local angular orientation with respect to the substrate surface, (ii) causing the stylus to engage and deform the substrate surface, (iii) re-aligning the stylus as or after the stylus engages the substrate surface, and (iv) measuring a substrate contact response.

In another embodiment of the invention, a method for determining the distribution of material properties at any location of a structural component through a local measurement obtained at a known position. This is achieved by (i) obtaining a local measurement with experimental testing, (ii) developing a computational model of the changes in the initial material properties within a structural component induced by one or more manufacturing processes, (iii) developing an algorithm through multiple computational models considering various initial stress-strain curves to correlate fabricated material condition gradients with initial uniform material properties, and (iv) verification and refinement of the algorithm based on material properties directly measured through contact mechanics from exemplar materials in the field or laboratory.

In some embodiments of the apparatus, one or more coupled components are contiguous. The apparatus may further include a mount, configured to attach to the substrate surface, having a magnetic device or attachment mechanism that allows the apparatus to be portable. The apparatus may be coupled to the substrate surface in order to perform contact mechanics with a frictional sliding test on the substrate surface. The apparatus may also be coupled to the substrate surface in order to perform contact mechanics with a series of indentation tests on the substrate surface. The core may further comprise an alignment mechanism that includes two or more floats configured to contact the substrate surface away from the stylus contact location in order to perform contact referencing without significantly damaging an area of the substrate being tested. The frame engagement mechanism may include an alignment mechanism utilizing a pre-set track in order to perform path referencing. The alignment mechanism may be configured to adjust for position and contour of the substrate surface through control of the local angular orientation of the stylus with respect to the substrate surface to perform scanning referencing. The alignment mechanism may be configured to adjust for position and contour of the substrate surface through control of the substrate with respect to the stylus to perform scanning referencing. The stylus engagement mechanism may measure force or displacement in an orientation normal or in plane with the substrate surface. The core may host two or more styluses in parallel or in sequence, wherein the styluses have similar or dissimilar geometries, to perform two or more contact mechanics tests in parallel or in series. The stylus may be manufactured such that the surface is the undeformed surface of a spherical ball bearing. The core may host one or more wedge-shaped styluses which are used to generate a substrate contact response, including micro-modifications on or beneath the sample surface. Two or more cores may be provided along with corresponding core engagement mechanisms for performing the contact mechanics test simultaneously or sequentially in different substrate surface areas or orientations. The core engagement mechanism may include at least one torsional spring.

In some embodiments, the method of utilizing stylus alignment may further include the preparation of the substrate surface prior to engaging the substrate surface with the stylus. The method may further include rehabilitating the substrate surface subsequent to measuring the substrate contact response. The method may utilize a contact mechanic test in a frictional sliding test mode. The method may utilize contact mechanics in a series of indentation tests mode. The method may re-align the stylus by contact referencing. The method may re-align the stylus by path referencing. The method may re-align the stylus by scanning referencing. The method of claim 15, further comprising controlling surface friction through the condition of the contact surfaces or lubrication. The method may further include the determination of the surface-to-surface friction coefficient experimentally through repeated frictional sliding tests on the same location of the substrate surface. The method may further include measuring the thickness of the substrate before and after preparing the substrate surface and/or before or after the contact mechanics test. The method may further include a contact mechanics test that is performed in more than one direction and orientation with respect to the sample surface. The method may further include the implementation of two or more contact mechanics tests performed in series or parallel while utilizing different stylus geometries to induce different effective strains within the substrate. The method may further include measuring the substrate contact response at multiple times to quantify rate-dependent and time-dependent strain release through viscoelastic and viscoplastic relaxation. The method may further include the use of the characteristics of the substrate contact response to predict mechanical properties using predictive equations derived from finite element analysis or by correlation of experimental data. The method may further include measuring the substrate contact response through a weld to determine if any manufacturing processes were performed to improve material characteristics, such as local yield or low toughness.

In some embodiments, the method determining the distribution of material properties at any location of a structural component through a local measurement obtained at a known position further may use local surface measurement taken on the surface of a structural component using a contact mechanics test. The method may further include the use of local measurement is of the material yield strength, ultimate tensile strength, strain hardening exponent, hardness, or fracture toughness. The method may further include a validation database which is used to develop and iterate the predictive algorithms. The method may further comprise the prediction of an effective property from the material condition gradient to obtain a single representative value for comparison with standardized tests that probe a larger sample volume. The method may further include the prediction of an effective property through further computational modeling, analytical equations according to homogenization theory, or validation database. The method may further include the consideration of an effective property that is the material yield strength, ultimate tensile strength and/or strain hardening exponent that is measured experimentally through laboratory tensile testing or contact mechanics. The method may further include an effective property which is the material fracture toughness or material properties from Charpy V-Notch testing.

DEFINITIONS

Definitions. As used in this description and the accompanying claims, the following terms shall have the meanings indicated, unless the context otherwise requires:

A "substrate" is the material being probed for mechanical properties through a contact mechanics test.

To "deform" or producing "deformation" includes making a permanent or time-dependent change in the shape of the substrate, including by removal of material from the substrate. In some instances, the deformation will also include micromodifications.

A "stylus" is an element engaging the substrate. The stylus geometry may be conical, spherical, 3-sided pyramid, 4-sided pyramid, wedge-shaped, or a combination thereof.

A "contact mechanics test" is the use of one or more styluses to create localized deformation and probe the mechanical response of a substrate while the rest of the structure remains unchanged. Specific implementations include a series of indentation tests, whereby for each indentation a hard stylus deforms the surface of a softer substrate by moving with its principal axis at a target angle approximately perpendicular to the substrate surface. Another implementation is a "frictional sliding test," whereby a hard stylus deforms the surface of a softer substrate while moving the stylus in a direction tangential to the local substrate surface. A contact mechanics test may be performed in a "machining" mode, where the stylus geometry, frictional contact conditions, and stylus travel velocity are selected to ensure that a ribbon or chip of material is removed from the sample surface. A contact mechanics test may also be performed in a "ploughing" mode, where the stylus geometry, frictional contact conditions, and stylus travel velocity are selected to ensure a ductile material response without any chip formation. Finally, the deformation can be in an opening mode where the material is flowing on each side of a wedge-shape.

An "irregular" surface is a substrate surface having local deviations from a planar orientation.

A "principal axis" of a stylus is defined as (i) the axis of revolution of the leading portion of the stylus, or as (ii) the axis intersecting the center of mass of the stylus with the leading portion of the stylus penetrating the furthest into the substrate.

A "local angular orientation" is the relative angle formed between a principal axis of the stylus and the direction tangent to the substrate surface at the position of engagement with the stylus.

A "frame" is a stiff element connecting the various apparatus devices, components, and subassemblies to a frame engagement mechanism.

A "frame engagement mechanism" is a combination of supports and mounts which engage the frame with the substrate surface.

A "mount" is a device or subassembly which operate and may consist of any combination of magnets, cables, belts, rails, wheels, rollers, fasteners, or adhesives.

A "multiaxial attachment" is a connecting member that may limit, transfer, or alter one or more degrees of relative motion between two or more devices and/or links connecting devices.

A "translational attachment" is a multiaxial attachment which limits the relative translation along up to two local axes and the rotation about at least two local axes.

A "rotational attachment" is a multiaxial attachment which limits the relative rotation about up to two local axes and the translation about at least three local axes.

A "float" is an element contacting the substrate outside of the area being engaged by the stylus for the purpose of maintaining a local angular orientation of the stylus.

A "rocking float subassembly" is an assembly of devices that allows for the independent relative motion between two or more floats, and may be configured to include,
  (i) "independent floats" which are floats that move with respect to floats mounted directly to the core,
  (ii) a rotational attachment,
  (iii) an "on-core attachment" which is a subassembly attachment location on the core that the rocking float subassembly can be mounted to via a rotational attachment, (iv) an "off-core component" which is a supporting member that may be attached to the core independently of the rocking float subassembly,
(v) an "off-core attachment" which is a subassembly attachment location on an off-core component that the rocking float subassembly can be mounted to via a rotational attachment,
(vi) a "float subassembly stabilizer" which is any number of springs and/or limit stops that controls the motion of the rocking float subassembly,
(vii) a "pivot attachment" which is a subassembly attachment location where the rocking float subassembly directly contacts the core to provide independent motion while being mounted or stabilized by a float subassembly stabilizer.

A "mode of displacement" is a combination of linear and/or rotational displacements about relative axes which describes the allowable motion of an attachment and connected devices and/or linkages.

An "alignment mechanism" is an apparatus to establish the position and/or local angular orientation of the principal axis of the stylus relative to an irregular substrate surface which may be accomplished through
(i) "path referencing," which is when the alignment mechanism is defined by a pre-set path which guides the mode of displacement of the core,
(ii) "contact referencing," which is when the alignment mechanism utilizes two or more floats which contact the substrate surface outside of the area engaged by the stylus in order to orient the stylus relative to the substrate surface, or
(iii) "scanning referencing," which is when the alignment mechanism probes the substrate surface topography, either before or during a contact mechanics test, and makes continuous adjustments of the local angular orientation of the principal axis of the stylus to adequately engage with the substrate.

A "stylus engagement mechanism" is a device that transfers forces to the stylus to penetrate the substrate surface during a contact mechanics test by either (i) applying force through the stylus or (ii) developing a reaction force locally normal to the substrate surface by setting an engagement depth of the stylus relative to the substrate surface. The stylus engagement mechanism may be directly coupled to the stylus or integral to the core. The stylus engagement mechanism may also be configured to measure a normal force and/or tangential force resulting from the engagement between the stylus and the substrate.

A "load control" test is when the stylus engagement mechanism is set to apply a known and nearly constant load (through the stylus) to the substrate.

A "displacement control" test is when the stylus engagement mechanism is set to maintain a constant the stylus relative to the surface of the substrate which is set by floats.

A "constant demand" condition is setting the stylus engagement mechanism in load control or displacement control.

A "core" is an element that transfers the action from external devices to the stylus. The stylus and the stylus engagement mechanism can be contiguous with the core so that the core and the stylus are formed from the same material (such as zirconia), or can be separate components. These external devices may include the alignment mechanism and core engagement mechanism.

A "core engagement mechanism" is a device configured to control the path of the core during the test. The path can be translational, rotational, or a combination thereof.

A "normal force actuator" is a device that, when a contact referencing alignment mechanism is used, applies a sufficient force to maintain the contact between the core and the substrate surface.

A "yoke" is a connecting member that may transfer the translational and rotational forces and displacements from the core engagement mechanism to the core without impeding the functionality of the normal force actuator(s).

A "transfer module" is an assembly that transfers the desired displacements and forces from one or more actuators to an alternate point of application, and is configured to couple the frame, core engagement, and core, or any combination thereof. For a specific application, one or more load transfer modules may be used separately or in series.

A "substrate contact response" is the characteristics that remain in the substrate after a contact mechanics test has been performed. Each substrate contact response may contain,
(i) a normal or tangential reaction force response
(ii) a normal or tangential displacement response
(iii) a "depth" which is the offset between the undeformed substrate surface and the distance of penetration of the stylus,
(iv) a "pile-up height" which is the offset between the undeformed substrate surface and the material that accumulates along the sides of the stylus above the original substrate surface,
(v) a "contact width" which is the peak-to-peak distance between pile-up heights which form on opposing sides of the stylus,
(vi) an "uncontacted substrate surface" which is the substrate surface that was deformed by movement of surrounding material but was not directly contacted by the stylus,
(vii) a "contacted substrate surface" which is the substrate surface that was deformed by engagement with the stylus through direct contact with the stylus,
(viii) a "microcrack" which is the creation of new surfaces in the substrate having an initiation position, length, and direction,
(ix) a "microstructural change" which is any change in the internal structure of the material. This includes, but is not limited to, the volume fraction of each crystalline structure, crystallographic and molecular texture, the free volume in the material, and the molecular arrangement,
(x) a "microvoid" which is the creation of additional space in the material such as crazes, interface debonding, and other phenomena generally associated with tension in the material, and
(xi) a "micromodification" which is any combination of microcracks, microvoids, or other noticeable changes in the substrate that is not a microstructural change.

A "substrate monitoring device" is an apparatus configured to allow for the measurement of one or more characteristics of the substrate contact response and/or the collection of material removed from the substrate.

A "field environment" is any location outside of a controlled laboratory setting which includes, but is not limited to, construction sites, manufacturing plants, trenches, repair or inspection facilities, but may also include locations on structures such as ships, bridges as well as any component of an assembly.

"Substrate surface preparation" is a method of removing large asperities and irregularities from the substrate surface through the use of physical or chemical processes such as etching, sanding, grinding, milling, and/or cleaning through traditional resources or guided tools.

"Substrate surface restauration" is a method of removing the substrate contact response from the substrate surface through the use of physical or chemical processes such as deformation, etching, sanding, grinding, milling, and/or cleaning through traditional resources or guided tools.

"Existing stresses" are stresses within a substrate which may arise due to existing service loads imposed on the substrate component and/or residual stresses from prior-manufacturing operations.

A "structural component" is any load bearing geometry which has been developed from a raw material, including but not limited to a plate, shell, pipe, I-beam, channel, angle, tubular sections, and more complex shapes that are cast, formed, machined or produced through additive manufacturing.

A "manufacturing process" is one or more steps used to produce and form a raw material into a fabricated structural component, including but not limited to casting, forming, heat treating, surface engineering and additive manufacturing processes. Examples of forming include rolling, bending and forging. Examples of surface engineering include shot-peening. Manufacturing processes can be further defined to include:
 i. A "permanent mechanical deformation" which arises due to tension, compression, or shear loading, in addition to localized processes such as shot-peening or abrasive wear. These processes cause greater strain hardening in regions of higher stress, and an associated change in mechanical properties.
 ii. A "thermal load" which includes the input or removal of heat to expose a material to a specific temperature at a pre-defined rate, such as during casting or heat treating. The material condition gradients will then develop due to differences in temperature from the heating or cooling of the material, in addition to microstructural changes from phase transformation or grain growth.

A "material condition gradient" is the change, if any, in the material characteristics, material properties or existing stresses in the material. The "material condition gradient" is a function of position within the structural component, such as in the through-thickness direction.

"Material characteristics" include the microstructural parameters, such as grain size and chemical composition.

An "effective property" is a value which represents the overall response of the non-uniform material condition gradient existing within a structural component. This value is representative of the bulk material property of a greater sample volume that is measured through standardized testing methods, such as tensile, Charpy V-notch or fracture toughness testing.

"Local measurements" are indicators of material properties or characteristics obtained by probing a small volume of material. The material property may be a direct measurement or indirect estimation of yield strength, strain-hardening exponent, ultimate tensile strength, elongation, Young's modulus, hardness, and fracture toughness. Material characteristics may be the chemistry, the grain size or other microstructural characteristics. The indicators are obtained at a known location within a gradient.

"Normalization" is the manufacturing process applied post-forming which induces changes in the post-forming material characteristics with the goal of homogenizing the material. This includes, but is not limited to, the manufacturing process commonly referred to as normalization, as well as cold-working processes, such as cold-expansion.

A "computational model" is a numerical tool, such as Finite Element Analysis (FEA), finite difference methods or molecular dynamics, used to simulate the material condition gradient caused by the fabrication of a structural component with a known geometry using a specific manufacturing process and material model.

A "validation database" is a set of empirical test results where the technique has previously been used, with some of the previous testing including a verification that the predictions were correct by testing at multiple positions with respect to the material condition gradient.

An "algorithm" is a predictive function that is developed through a computational model, with or without additional calibration input from a validation database, to correlate local measurements with material condition gradients and effective material properties.

BRIEF DESCRIPTION OF THE DRAWINGS

The foregoing features of embodiments will be more readily understood by reference to the following detailed description, taken with reference to the accompanying drawings, in which:

FIG. 20 is a schematic side view of a contact mechanics test apparatus and contact referencing alignment mechanism according to an exemplary embodiment.

FIG. 21 is a schematic front view of a contact referencing alignment mechanism for the apparatus of FIGS. 1 and 19 according to embodiments of the present invention. This includes exemplary testing apparatuses capable of performing both displacement and load control experiments.

FIG. 22 is a schematic front view of the contact referencing alignment mechanism of FIG. 21, showing a contact indicator according to embodiments of the present invention.

FIG. 25 is a schematic perspective view of another exemplary contact referencing alignment mechanism for the contact mechanics testing apparatus of FIGS. 1 and 19 according to embodiments of the present invention.

FIG. 26 is a schematic perspective view of another exemplary contact referencing alignment mechanism for the contact mechanics testing apparatus of FIGS. 1 and 19 according to embodiments of the present invention.

FIGS. 27A-F depict various schematic views of an exemplary testing apparatus with an alignment mechanism capable of contact referencing according to embodiments of the present invention.

FIGS. 30A and 30B are schematic views of an exemplary rocking float subassembly according to embodiments of the present invention.

FIG. 31A-C are schematic views of an exemplary rocking float subassembly according to embodiments of the present invention.

FIGS. 34A and 34B are schematic side views of another exemplary scanning referencing alignment mechanism for the contact mechanics testing apparatus of FIGS. 1 and 19 according to embodiments of the present invention.

FIGS. 35A-C are schematic perspective view, front view, and side view, respectively, of an exemplary testing apparatus core capable of hosting two styluses according to embodiments of the present invention.

FIG. 50 is a schematic view of an exemplary frame and frame engagement mechanism for the testing apparatus of FIGS. 1 and 19 according to embodiments of the present invention.

FIGS. 54A and 54B are schematic perspective views.

FIG. 56A depicts a schematic perspective view and FIG. 56B depicts a schematic side view of an apparatus capable of substrate surface preparation according to embodiments of the present invention.

DETAILED DESCRIPTION OF SPECIFIC EMBODIMENTS

Overview of Apparatus, Methods and Applications

Figure 1:
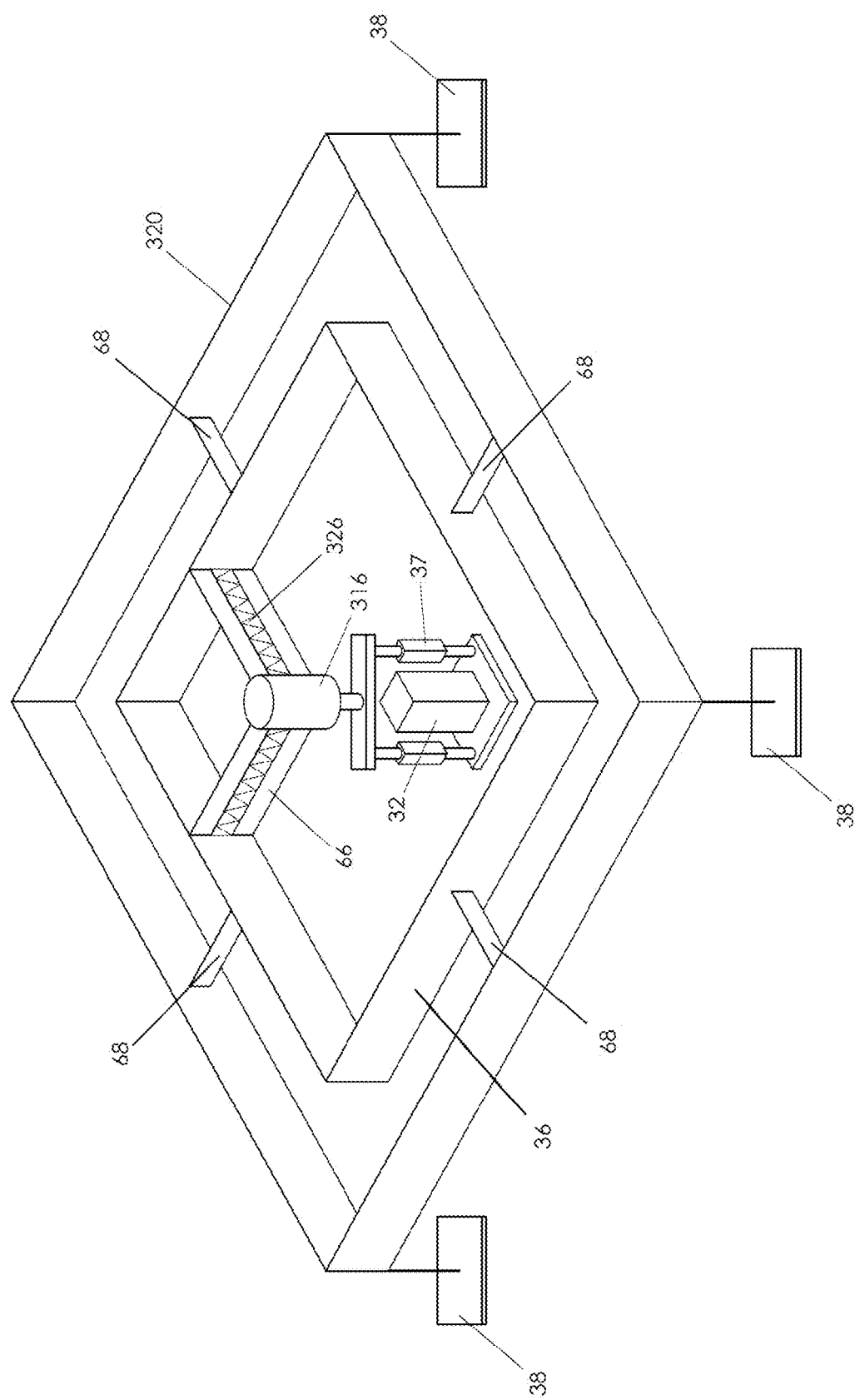
FIG. 1 is a schematic perspective view of a contact mechanics test apparatus according to exemplary embodiments.
Figure 19:
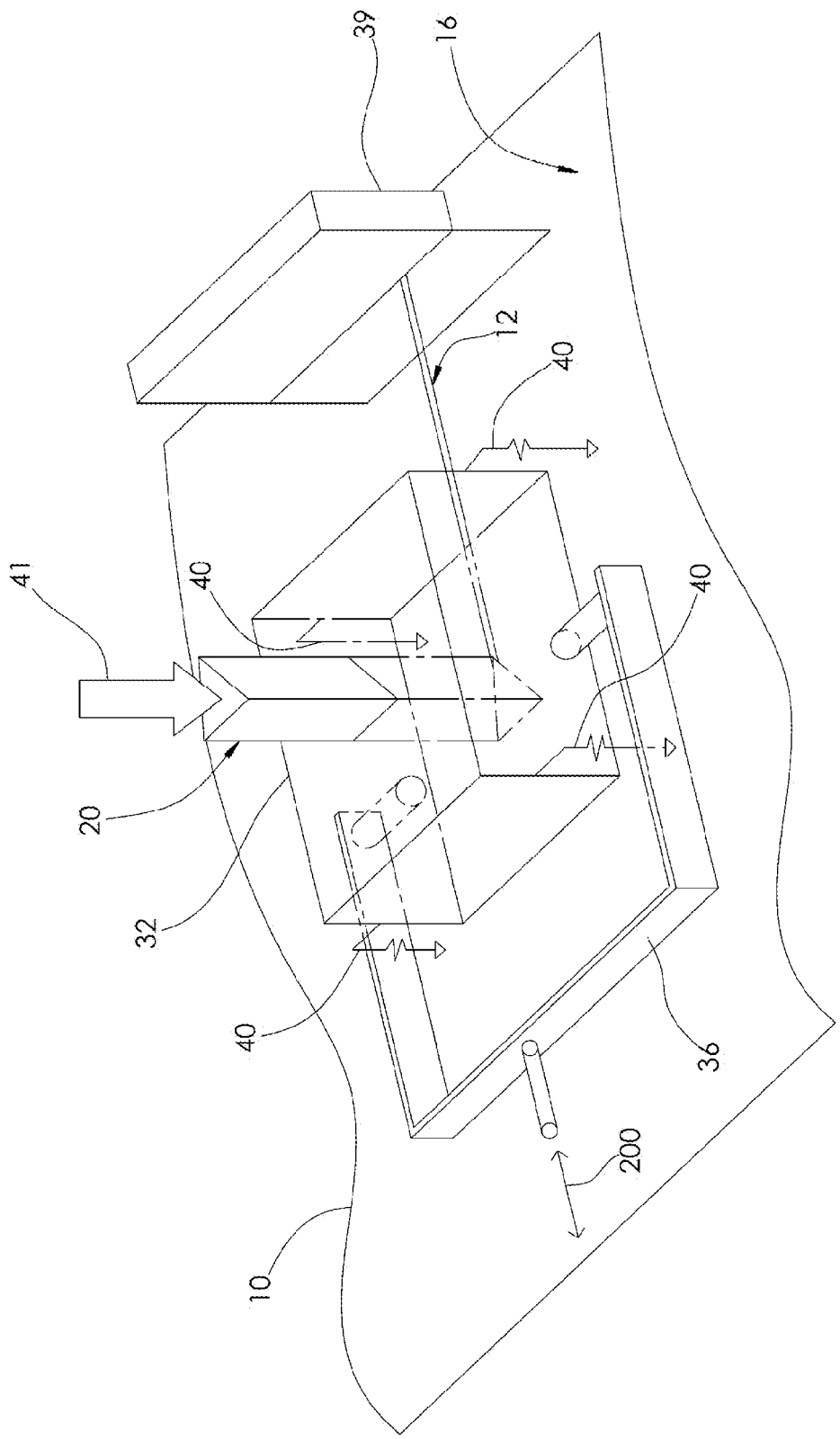
FIG. 19 is a schematic perspective view of a contact mechanics test apparatus according to exemplary embodiments.

Provided in one embodiment is a contact mechanics test apparatus, as shown in FIGS. 1 and 19, configured to deform a substrate with at least one stylus, and the monitoring of the substrate response with at least one substrate monitoring device. In at least one embodiment, the apparatus may be also referred to as a testing apparatus, particularly when the apparatus is configured to perform a contact mechanics test. In one version of the embodiment, the deformation and the measurement device are part of a single sequence of travel on the substrate. The apparatus embodiment, as shown in FIG. 19, can be comprised of the following elements: a stylus 20, a core 32, a stylus engagement mechanism 41, a core engagement mechanism 36 a frame 320, a frame engagement mechanism 321 and a substrate monitoring device 39. FIG. 1 is a schematic diagram of an apparatus capable of performing a multi-directional frictional sliding test. This embodiment requires a test apparatus frame 320 which is fixed to the substrate surface 12 via the frame engagement mechanism 321 further comprised of supports 68 and mounts 38, which may include magnets. The test apparatus frame 320 acts as a structural support for two displacement actuators 66, which provide translational displacement to the core 32 along two perpendicular axes. This displacement is guided via two load transfer modules 35 and applied via two translation transfer modules 35. In this embodiment, a yoke 316 is also utilized to transmit the translational and rotational displacements to the core 32 with respect to the substrate surface. A normal force is applied to the core 32 via normal force actuators 37, which are coupled to a yoke 316. The testing apparatus may also be configured to be portable so that it may be attached to existing large structures in a field environment, or may be used in small-scale laboratory testing. The apparatus provided herein simplifies, expedites, and improves the testing procedure in comparison to existing contact mechanics test apparatuses.

Figure 2:
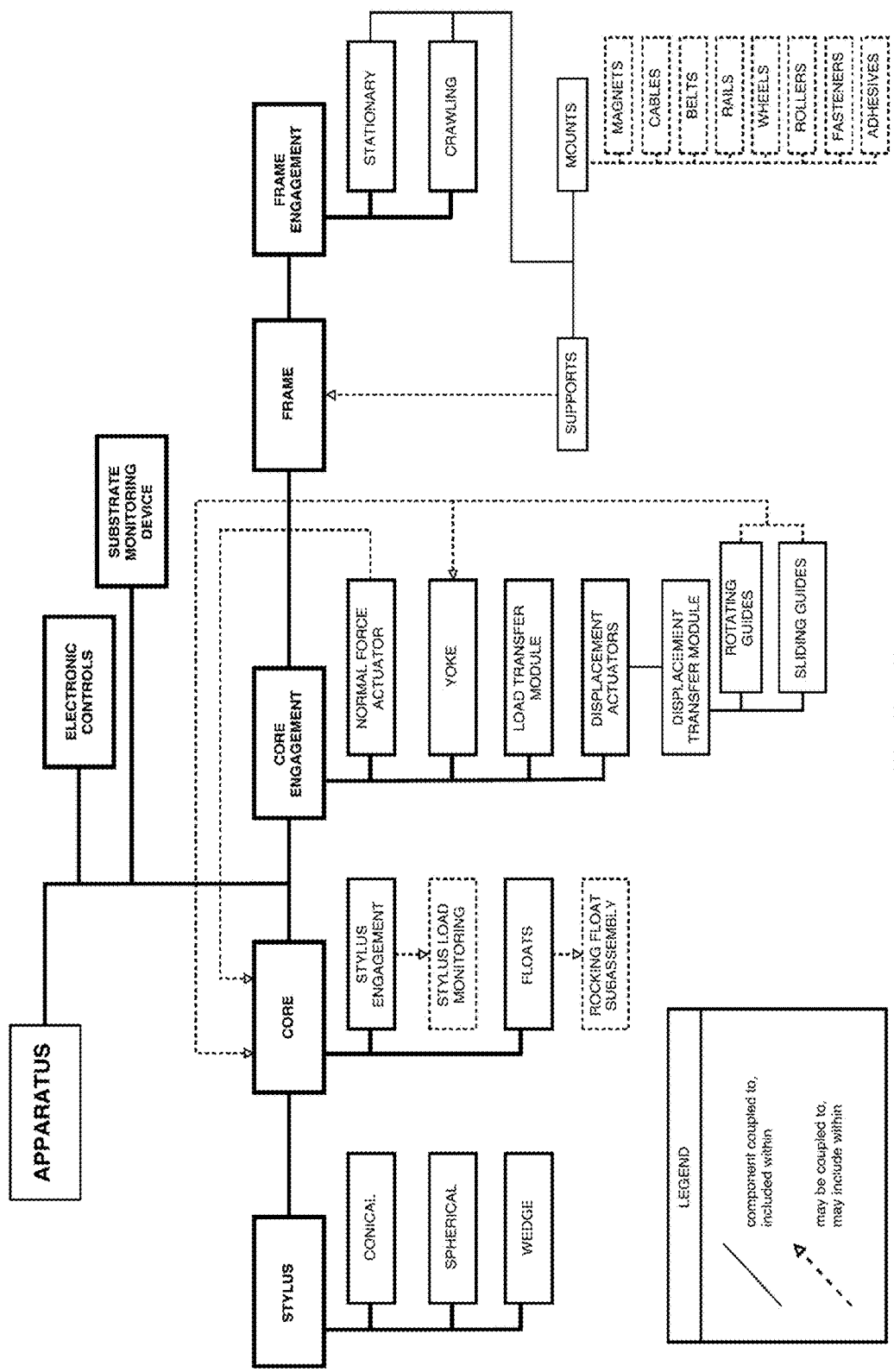
FIG. 2 is a flow chart indicating the essential components of the apparatus according to embodiments of the present invention.
Figure 3:
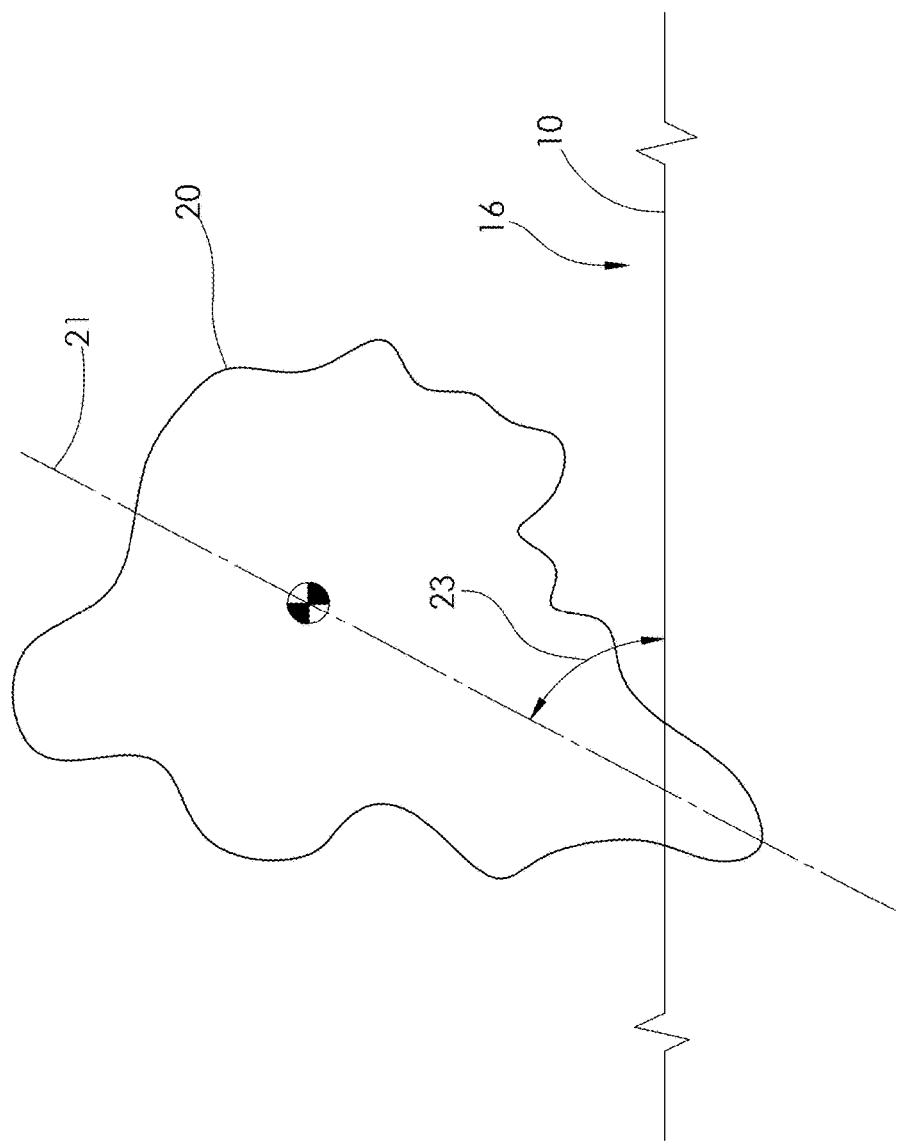
FIG. 3 is a schematic side view of a stylus with irregular geometry according to embodiments of the present invention.
Figure 4:
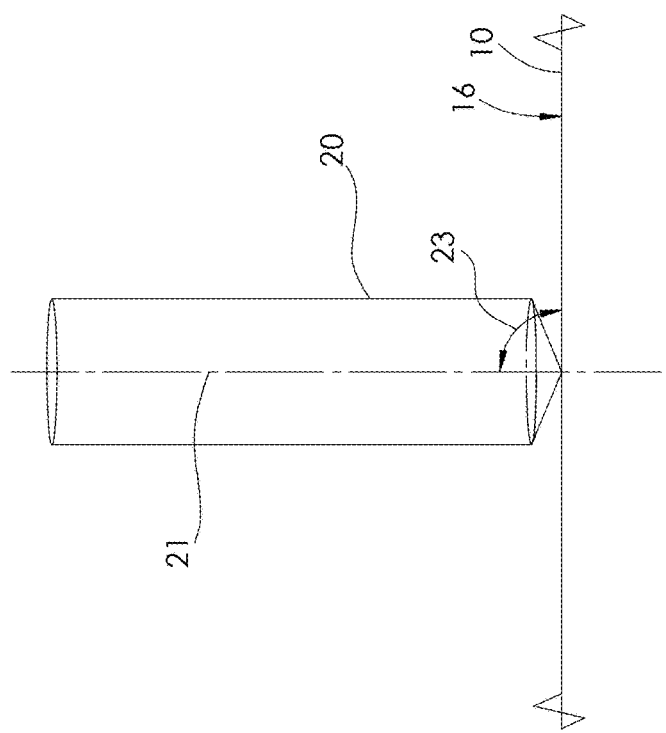
FIG. 4 is a schematic side view of a stylus with axisymmetric geometry according to embodiments of the present invention.

One novelty of the present apparatus over the prior art is the ability to perform stylus alignment with respect to the substrate surface through the use of an alignment mechanism 40 that adapts to the local substrate surface 16. The impact of this novelty is that tests on a curved substrate can be done at different locations on the sample while ensuring that the alignment is the same at each of these locations. For a series of indentation tests, the stylus 20 is either aligned by the apparatus as it travels along the substrate surface 16 or aligned as needed prior to each indent. For a frictional sliding test, the stylus 20 is continuously aligned as it travels along the substrate surface 16. The alignment mechanisms of the apparatus ensures stylus alignment for any in-plane substrate surface geometry, whereas prior art methods used two separate operations, deformation and surface scanning, to correct for curvature only in the direction of stylus translation. The alignment mechanism 40 can be embodied in a number of different ways which are discussed in detail later in this document along with demonstrative images. The general concept is to maintain reference of the apparatus with the substrate surface 16 when the stylus 20 moves along the surface (See Alignment Mechanism). Another novel feature of the apparatus is the shaping of one or more stylus 20 geometries to obtain different substrate contact responses. Some embodiments include multiple styluses 20, to either gain more reliability in the response we measure, or to capture the response of different testing conditions at the same time. In general, the testing conditions produced by the stylus 20 or multiple styluses 20 have one or more purposes: to deform the substrate 10 to generate permanent deformation and/or time-dependent response characteristics and/or capture the built-in residual stress of the substrate 10. Some embodiments can further have multiple cores. The specific embodiments for these different styluses 20 are further discussed after the general description of the testing methods and their effect (See Stylus). A summary of all of the essential components of the apparatus described herein is provided in FIG. 2.

One method is a novel use of contact mechanics testing to maintain a local angular orientation of a stylus 20 relative to the substrate 10, engaging the stylus 20 with the substrate 10, deforming the substrate 10, and characterize the response of the material by measurement of the substrate contact response 12. The testing apparatus may determine a full set of mechanical properties of a substrate 10 without destroying the function of the structure. In addition, the testing apparatus allows for the measurement of changes in local material mechanical properties along the length of deformation through characteristics of the substrate contact response 12.

One method is a novel use of iterations of contact mechanic tests along with other physical measurements and analysis to predict property gradients and effective mechanical properties of a substrate based on substrate surface tests and additional manufacturing information available about the substrate. Although analysis techniques have previously been developed to perform a simulation of the effect of manufacturing on property gradients, the new method incorporates a combination of a series of laboratory tests to develop and validation the predictive equations, including the use of contact mechanic tests on cross-sections of representative samples.

The testing apparatus and methods may therefore be utilized for material property characterization in advanced small-scale fabrication, as well as in traditional industries involving welded structures, damaged structures, wear applications and other locations that are susceptible to failure. The testing apparatus and methods are also suitable as a tool for accurately probing mechanical material properties in manufacturing quality control, condition assessment, and diagnostic testing applications. The testing apparatus may provide a system configured to perform a testing method for evaluating mechanical properties of engineering, or structural, materials, including a measure of the strength, hardness, ductility, fracture toughness, Charpy v-notch properties, fatigue resistance, and both existing and pre-existing stresses. The testing apparatus provides an apparatus and instrumentation to simplify the implementation of the testing method. It also allows for characterizing material anisotropy.

For many applications, mechanical properties of interest include yield strength, strain hardening behavior, ductility and toughness. Contact mechanics testing has recently been proven to allow users to accurately quantify the strength and ductility of metals and other materials. The ploughing of material during a contact mechanics test by a hard stylus 20 induces a steady flow of permanent deformation in the softer substrate 10. The material displaced from the deformation is piled on both sides of the stylus 20, and the piles have an identifiable height relative to the surface of the substrate 10. The characteristics of the substrate contact response 12, along with the reaction force from engagement between the stylus 20 and the substrate 10, are used as inputs into reverse algorithms which output mechanical properties of the substrate 10.

In addition to substrate mechanical properties, the testing apparatus and method are suitable for evaluating residual stresses that exist in the substrate prior to testing, as well as the intrinsic coefficient of adhesive friction for sliding contact between the material of the stylus 20 and substrate 10. Additional applications include the quantification of time or rate-dependent material behavior, such as viscoelastic, viscoplastic, or strain-rate dependent properties. In other applications, the mechanical characterization may be combined with chemical and geometrical characterization techniques, such as non-destructive substrate thickness measurements.

In certain applications, the apparatus may be used to perform a series of indentation tests by using the same stylus engagement mechanism to apply the load and the core engagement mechanism to relocate the stylus 20 between indentations.

In other applications, a frictional sliding test is conducted in a machining mode to remove one or more ribbons or chips of material. These removed materials are collected using a substrate monitoring device 39, and may be tested using existing methodologies for microstructure, chemistry, and mechanical properties. With this approach, more sophisticated laboratory testing techniques can be used to study a substrate 10 while only removing a superficial amount of material.

This apparatus and method will greatly impact practicing engineers and scientists, who can use the apparatus and method to obtain a quantitative assessment of the mechanical properties of substrates from assembled components. This allows for the measurement and prediction of the remaining service life in aging infrastructure and equipment without the removal of the substrate for traditional mechanical testing in a laboratory. In addition, the apparatus and method can be used on production lines to continuously perform quality control and assurance in manufacturing. These capabilities will greatly impact many professions, such as civil, mechanical, nuclear, naval, aerospace, and automotive engineering. The ultimate result will be greater confidence in the structural integrity and mechanical behavior of both newly manufactured and existing structures, promoting lower costs, less uncertainty, and greater public safety.

Following below are more detailed descriptions of various concepts related to, and embodiments of, a contact mechanics testing apparatus and a method of contact mechanics test. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Detailed Description of the Methods

The method of using the apparatus can be generally described as follows. Referring to FIGS. 1, 3-5B, and 19, a stylus 20 is forced to engage with a substrate 10 with the principal axis of the stylus 21 at a specified local angular orientation 23 to the substrate surface 16. A novel characteristic of one of our methods is stylus alignment utilizing an alignment mechanism that maintains the stylus local orientation for a series of indentation tests and/or a frictional sliding test. Depending on the embodiment, the alignment mechanisms can be implemented by different components of the apparatus. When the method of stylus alignment is used for a series of indentation tests, it is important that the surface in the area of subsequent tests remains unaffected by contact of the apparatus. Similarly, the test results should not be affected by contact of the apparatus over an area of the substrate deformed in a prior test. This effectively allows for precise and efficient positioning of one or more styluses that are properly aligned with the local substrate surface for each test within the series. This is important for curved or irregular surface geometries where the local surface orientation changes as the stylus is repositioned along the substrate surface.

During a contact mechanics test, the stylus 20 engages with the substrate 10 through the stylus engagement mechanism 41 to deform the substrate 10 and create a substrate contact response 12. The deformation of the substrate 10 may form piles 14 on one or both sides of the stylus 20, which then remains as a characteristic of the substrate contact response 12. During a frictional sliding test, the core engagement mechanism 36 further deforms the substrate 10 by moving the stylus 20 along the substrate surface 16. During an indentation test, the core engagement mechanism 36 translates the stylus to different locations along the substrate surface 16 for additional tests. The amount of substrate deformation by the stylus 20 may be dependent on the geometry of the stylus 20 (e.g., the stylus included angle 22), the magnitude of the engagement load applied to the stylus 20, physical properties of the substrate 10, and the type of contact mechanics test (i.e. frictional sliding or indentation). The physical properties of the substrate 10 may be determined by analyzing the substrate contact response 12. Other novelties of this method include how the material response is studied and how the stylus 20 is shaped and aligned to obtain specific responses.

An embodiment of the method includes utilizing data collected by the substrate monitoring device 39 of the contact width 24, depth 26, and pile-up height 28 along with reverse algorithms to predict the stress-strain curve of the substrate 10 and establish a quantitative index for the hardness, yield strength, ultimate testing strength, strain hardening behavior and elongation at break of the substrate 10.

Figure 5A:
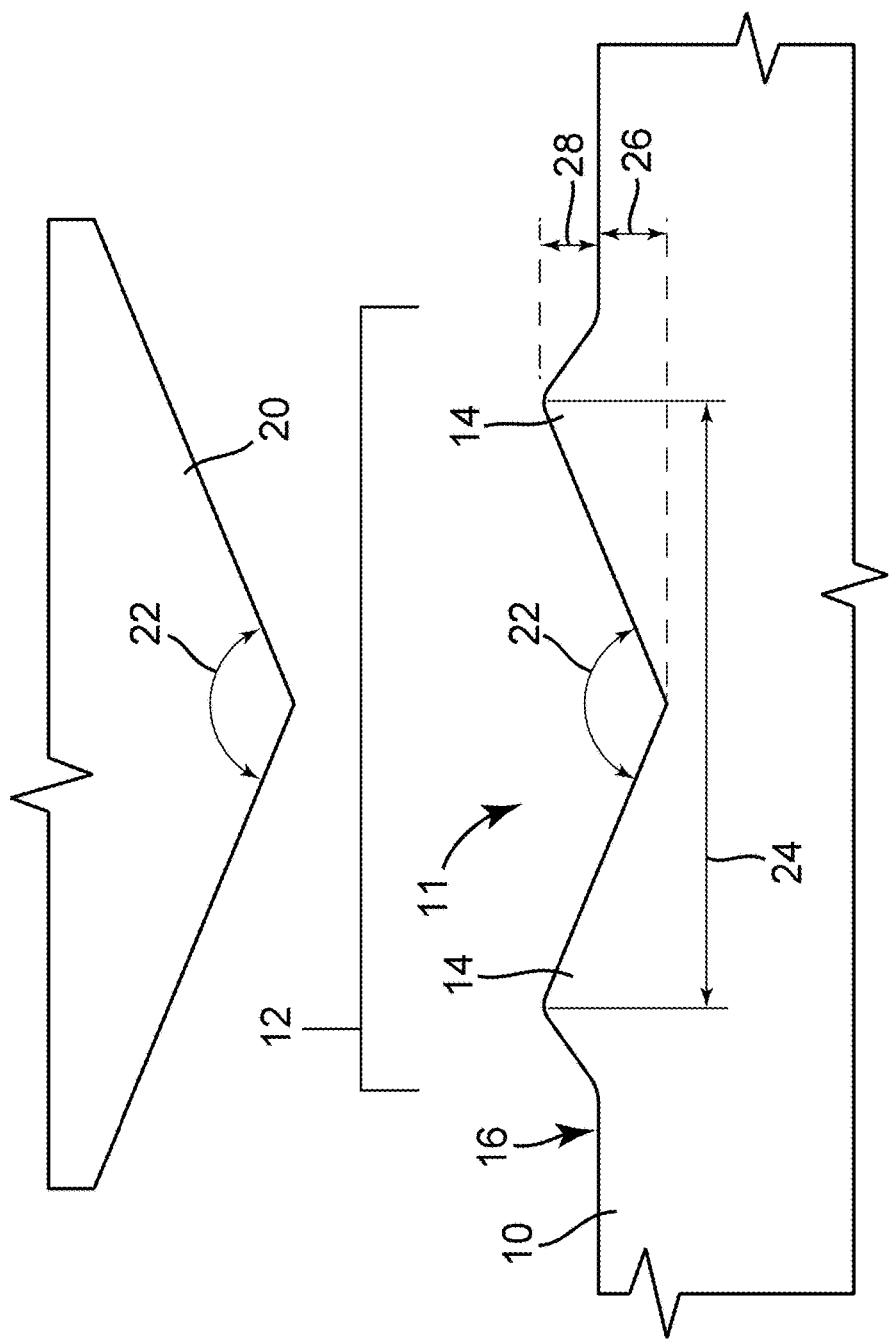
FIGS. 5A-B are schematic front views of a stylus and substrate contact response after deformation of the substrate by the stylus according to an exemplary embodiment.
Figure 5B:
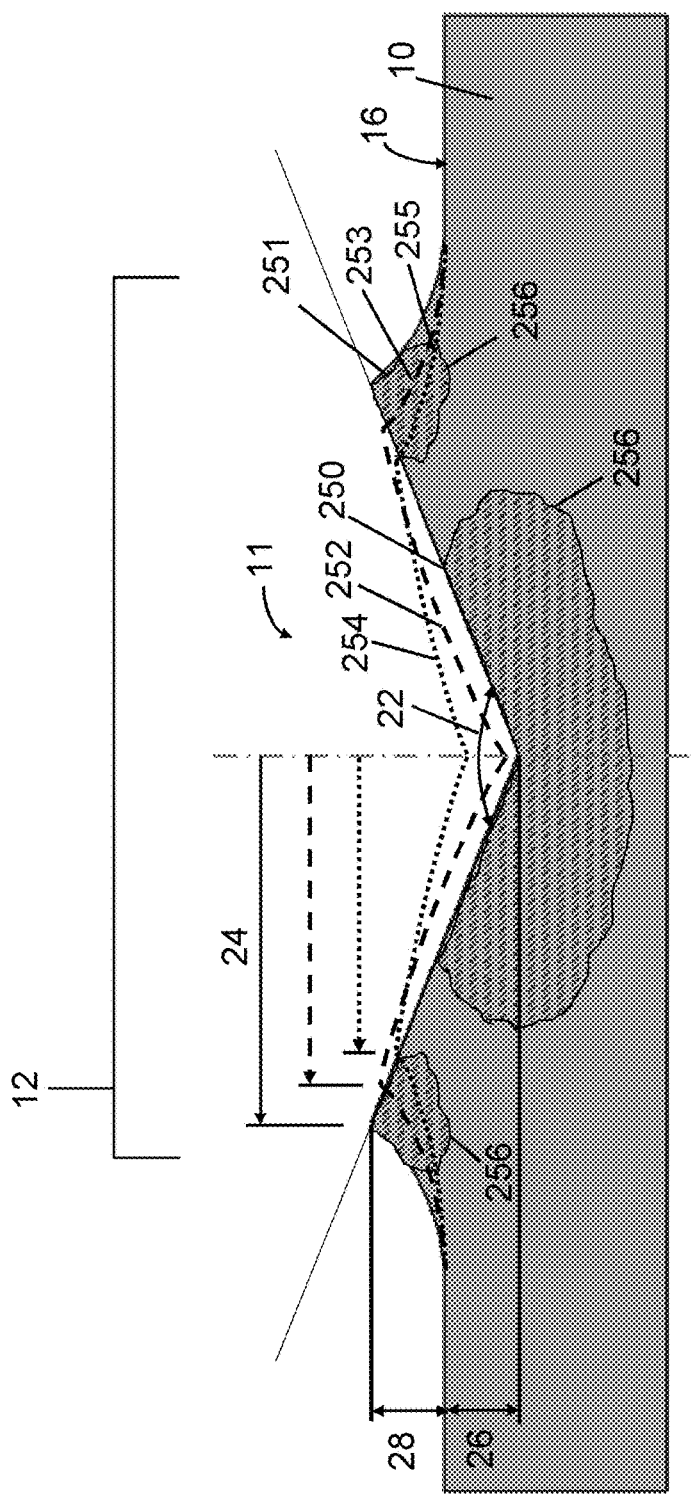

FIG. 5A provides an example of an idealized substrate contact response 12 which may be expected in a substrate being deformed by a conical or pyramid-shaped stylus 20. This substrate contact response 12 is typical of an indentation test or frictional sliding test in a ploughing mode to induce plastic deformation. Distortions of this profile occur from the relaxation of elastic strains from removing the stylus 20, time-dependent strain relief like viscoelasticity or viscoplasticity, or the redistribution of existing stresses which may be caused by either existing service loads or prior manufacturing processes. In FIG. 5B, multiple substrate contact response 12 profiles are shown. The contacted substrate surfaces, designated 250, 252, 254, are in direct contact with the face of the stylus 20, and the uncontacted substrate surfaces, designated 251, 253, 255, are created by deformation of the substrate 10 being pushed around the stylus 20. Profiles 250 and 251 represent the geometry of the loaded substrate, where the contact profile 250 matches the geometry of the stylus. Profiles 252 and 253 represents a substrate which has relaxed, with resulting changes in the depth 26, pile-up height 28, contact width 24, and stylus included angle 22. Profiles 254 and 255 represents a substrate that has experienced greater strain relaxation than profiles 252 and 253. These measurements of deviations in substrate contact response characteristics may be utilized for predicting material properties related to strain relaxation. For a viscoelastic or viscoplastic substrate, profiles 250 and 251 represent the geometry under loading, profiles 252 and 253 represent the geometry after unloading, and profiles 254 and 255 represent the geometry a longer time after unloading. For a substrate with existing stresses, profiles 252 and 253 may exhibit the geometry of a substrate contact response parallel to the direction of maximum stress, and profiles 254 and 255 may exhibit the geometry of a substrate contact response 12 perpendicular to the direction of maximum stress where greater strain relaxation will occur. Additionally, regions 256 may undergo some form of micromodification.

Based on these observations of changes in the substrate contact response 12, another embodiment of the method includes utilizing data collected by the substrate monitoring device 39 to predict the extent of existing service loads and/or pre-existing residual stresses. Loads (e.g., weight on a beam) induce stresses within a material during service in addition to residual stresses which remain from prior loading during manufacturing, e.g., welding. A common method for evaluating the magnitude of these existing stresses within a material is to measure the extent of elastic strain relief when those stress distributions are changed. For instance, this may be done by drilling a hole in the material and measuring the change in diameter of the hole from strain relief. For one embodiment, the apparatus is used to perform a contact mechanics test to change the existing stress distributions, and the strain relief may be observed by distortions from the idealized substrate contact response 12, specifically deviations of the contacted substrate surface after the stylus 20 has been removed. In one embodiment, the directional nature of stress and strain is used to quantify the magnitude of existing loads. For example, a beam in bending has significantly greater stresses along its length than in the transverse direction perpendicular to its length. This understanding is used to examine the effects of the greater stress direction on the resulting substrate contact response measurements by performing a series of frictional sliding tests, including at least one in the direction of the anticipated maximum principal stress (e.g., length direction for a beam in bending or axial loading), and another roughly perpendicular to the first test in the direction of minimum principal stress (e.g., transverse direction), if these may be determined. The substrate contact response 12 from these deformations can then be directly compared to assess the extent of built-in or existing stresses within the substrate 10. In another embodiment, the strain-relaxation of residual stresses may be quantified by examining the change in substrate contact response 12 geometry along the length of a single contact mechanics test. For example, when performing a contact mechanics test through a welded connection it can be expected that the area closest to the weld will contain significantly more residual stresses than the substrate 10 farther from the weld. This difference will be observed by measuring the differences in substrate contact responses 12, where the greater release of elastic compressive strains in the area closer to the weld would lead to a closing displacement in the direction of the contact width 24.

Another application of measuring deviations in the substrate contact response is for observing rate-dependent material properties such as viscoelasticity or viscoplasticity. This may be accomplished by performing contact mechanics tests at multiple speeds, using styluses with dissimilar geometries, or by repeatedly measuring the substrate contact response at different time intervals.

Another embodiment of these concepts is to compare the substrate contact responses 12 made with different engagement loads and stylus geometries, allowing for information to be obtained regarding the mechanical behavior of the substrate 10. Consider, for example, a case where two simultaneous deformations were made at a fixed load and velocity, but one stylus 20 had an included angle 22 of 140° and a second stylus 20 had an included angle 22 of 170°. These two styluses 20 would create different amounts of deformation 11 in the substrate 10 and different strain rates. Being able to collect data on different amounts of strain would allow us to get more accurate yield (using the 170° included angle stylus) and strain hardening data (using the higher deformation 140° included angle stylus). Being able to compare strain rates allows viscoelastic deformation to be ascertained in materials where such behavior is possible and relevant. In this multi-deformation setup, the ability to adjust the engagement load on each stylus 20 would allow us to fine tune the stress-strain regime we are measuring, ranging from very low plastic strain at the yield point to extremely high strains for enhanced strain hardening data. Using various engagement loads allows for different penetration depths below the substrate surface 16. By comparing the substrate contact response 12 from a low load (shallow) test and high load (deep) contact mechanics test, information concerning the gradients of existing stresses within the substrate 10 can be measured. These gradients through the thickness direction of a substrate 10 often exist from the manufacturing processes associated with forming a structural component from a raw material.

In addition to substrate 10 mechanical properties, the intrinsic coefficient of friction between the stylus 20 material and substrate 10 may be measured using embodiments of the apparatus and methods. This is accomplished through repeated frictional sliding tests performed at the same location within the substrate. During a frictional sliding test, the tangential load between the stylus 20 and substrate 10 is considered to contain two components, the adhesive component from friction which is dependent on the surface conditions of the materials in contact, such as roughness and lubrication, and the ploughing component which is dependent on the material properties of the substrate material and depth of penetration of the stylus. With repeated frictional sliding tests performed at a constant load, the ploughing component of the tangential load will go to zero and only the adhesive component remains, allowing for a simple description of the coefficient of friction between materials. The use of various lubricants may also be included in the experiment to assess the changes in friction coefficient.

In certain embodiments, the method may include a series of indentations in conjunction with frictional sliding tests. Such a method may be used, for example, for calibration and alignment verification. In other embodiments, the core is set to rotate during the contact mechanics test, such that the trajectory of the contact mechanics test changes in order to study the behavior of the substrate when deformed at different orientations.

Gradients and Effective Properties from Local Measurements

Material properties can be different at the substrate surface test location than within the substrate. The following new method enables the use of contact mechanics test results to predict the material condition gradients within a fabricated structural component as well as the effective property measured through standardized tests, including but not limited to tensile tests and contact mechanics. Material condition gradients arise due to existing stresses within the material, which occur due to the manufacturing processes required to fabricate a structural component from a raw material. These manufacturing processes include permanent mechanical deformation, thermal loads, or the combination of the two processes. The method may comprise the use of one or more local measurements that are input into predictive algorithms to obtain a material condition gradient as a function of position within the structural component. The algorithms are developed through computational models that simulate the creation of these gradients from an initially homogeneous material. These algorithms are verified and refined through the direct testing of material condition gradients via contact mechanics in the field and the laboratory. The models consider the changes in the material properties induced by manufacturing processes by including the relevant structural component geometry, mechanical or thermal loads, and boundary conditions. By considering multiple initial stress-strain curves, algorithms can be derived to correlate fabricated material condition gradients with the initial stress-strain curve. With this approach, a local measurement, obtained through a contact mechanics test or otherwise, is correlated to material properties throughout the structural component. In one embodiment, this local measurement is taken on the exposed surface of the structural component.

An effective property can be obtained from the material condition gradient through an additional computational model, such as the simulation of a tensile test with the material condition gradient, or analytical expressions through established techniques like homogenization theory. A validation database developed through prior empirical tests may also be used.

Figure 6:
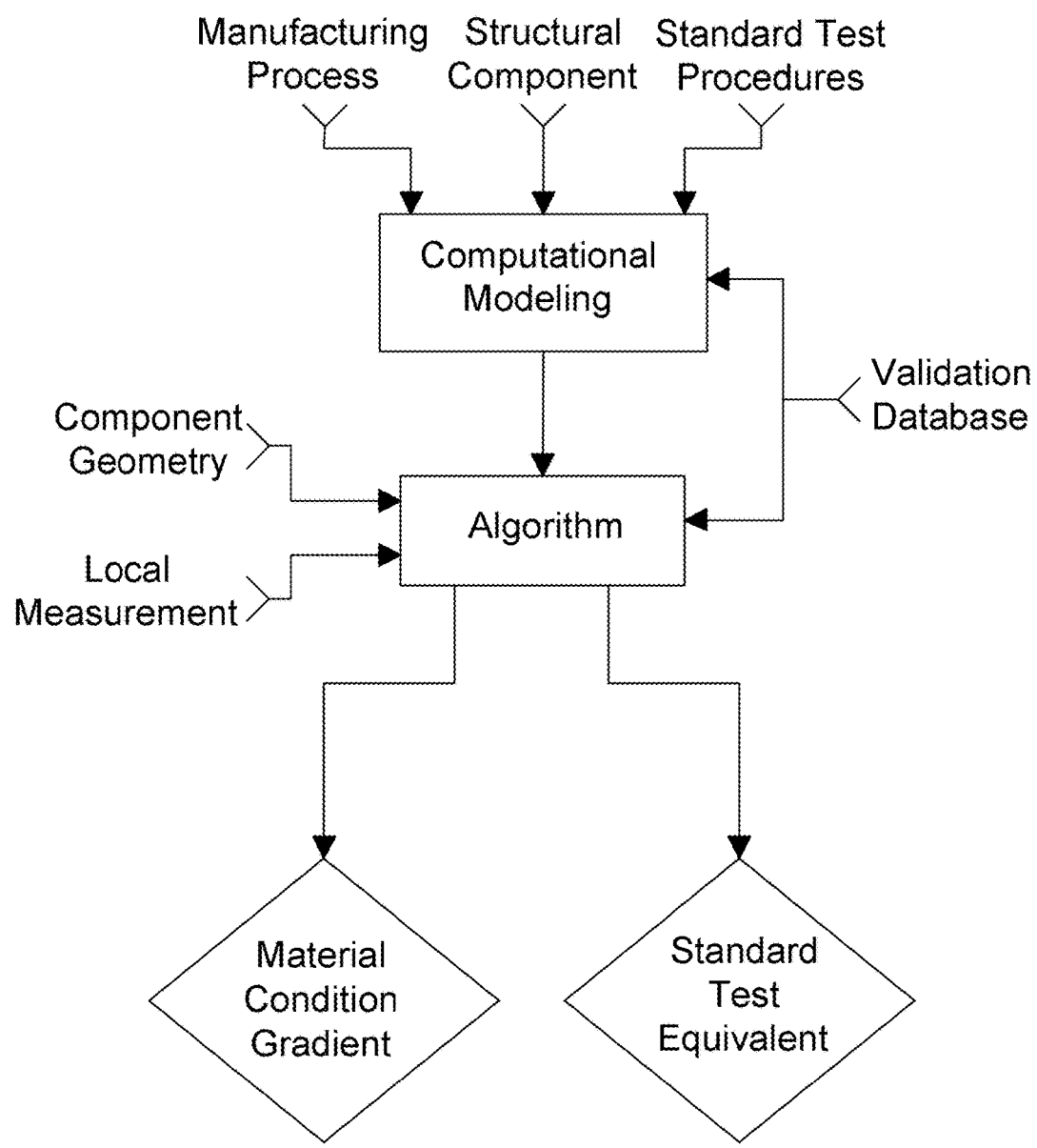
FIG. 6 is a flow chart indicating the general process of developing algorithms with computational models, and using local measurements to predict material condition gradients and effective material properties for a structural component of known geometry and manufacturing process.

The general approach to predicting bulk mechanical properties from local measurements is provided in FIG. 6. Algorithms are developed based on a computational model specific to the type of manufacturing process, the structural component and standard test procedure, when a standard test equivalent is desired. The computational models and algorithms are validated against known databases built from field and laboratory test results. These algorithms are used to describe the changes in material properties from chemical and microstructural segregation, strain hardening from shape forming, and microstructural changes induced by manufacturing processes. Once these algorithms are developed, the application of the method no longer requires computational modeling; the inputs are the component geometry of the structural component and a local measurement, and the outputs are the material condition gradients and the effective property value.

Computational models are used to develop algorithms by simulating changes in material characteristics and/or material properties from the initial material to a fabricated material. This includes the true stress true strain material response in viscoelasticity or plasticity. It also includes approximations of changes in material characteristics as a function of the distance within the structural component, such as away from the surface. Computational modeling also offers the ability to predict residual stresses from forming and other prior or post manufacturing process. For example, residual stresses can be used and included in algorithms where contact mechanics is used to obtain and use indirect measurements of mechanical properties from the surface. Computational modeling and/or the algorithms can be improved using a validation database. This may include, for example, correction factors for expected material condition gradients that are typical for the application such as alloy and microstructure segregation.

Figure 7A:
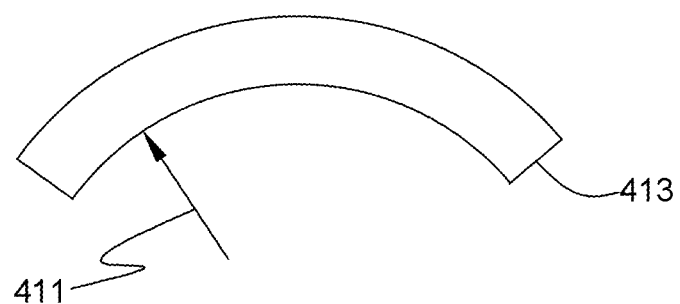
FIGS. 7A-B are schematics detailing component geometry for exemplar embodiments of structural components.
Figure 7B:
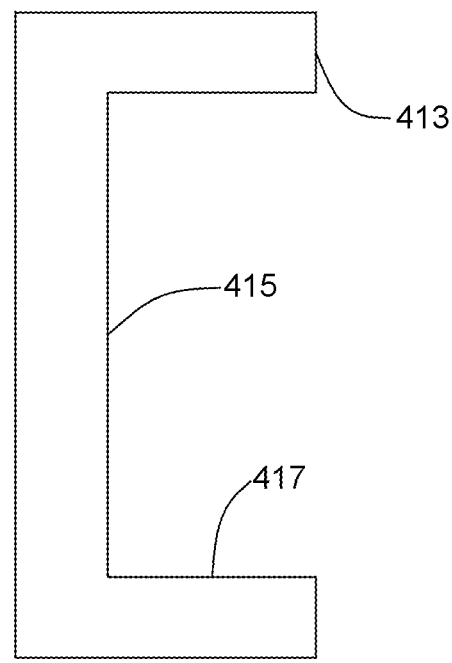

The component geometry is dependent on the type of structural component as shown in FIG. 7, and can generally be described as the dimensions necessary to build a representative computational model. For the specific embodiment of a cylindrical pipe FIG. 7A this includes two parameters, the wall thickness 413 and radius 411. For another embodiment involving a more complicated channel FIG. 7B, three parameters describing the thickness 413 and lengths of the web 415 and flange 417 would be required.

Figure 8:
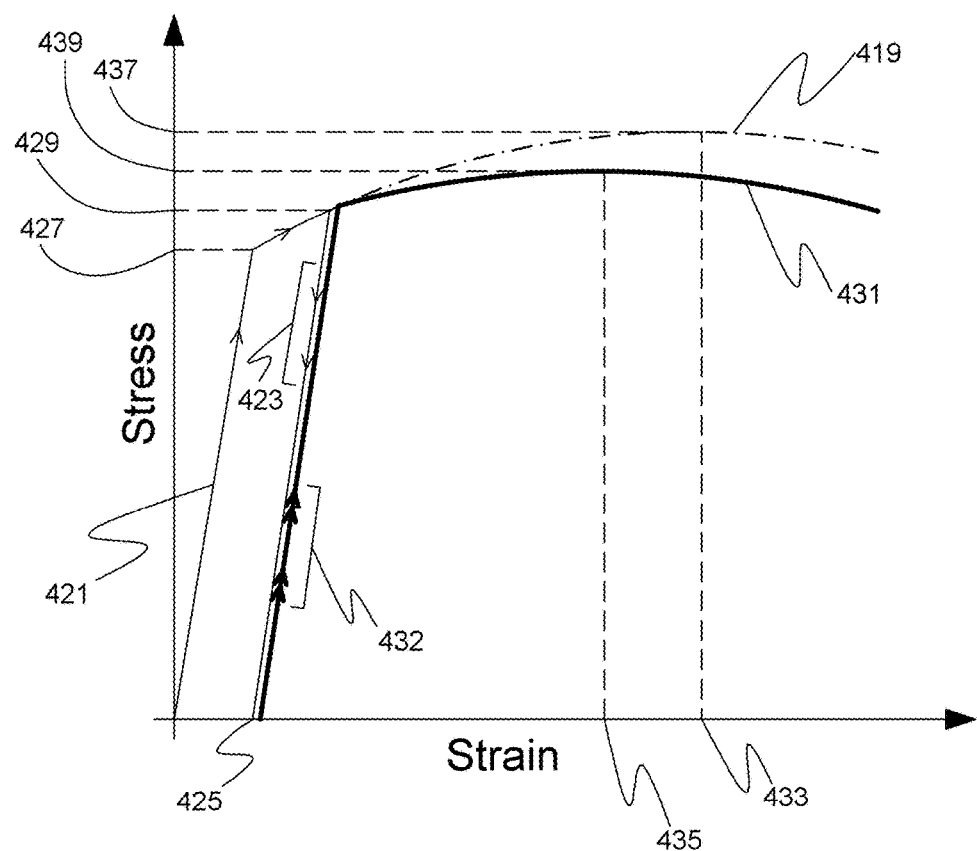
FIG. 8 is a schematic demonstrating the change in initial material properties induced by manufacturing processes.

Material models include equations on how the material characteristics and properties vary for different manufacturing processes. In FIG. 8, a metal or alloy material exhibits an initial stress-strain curve 419. Manufacturing processes apply loading to the material 421, which may or may not be subsequently removed 423. These manufacturing process result in permanent plastic strain 425 if the material is loaded beyond the initial yield strength 427. This causes a change in the mechanical properties of the material, such as an increase in the fabricated yield strength 429. A stress-strain curve representative of the fabricated material 431 is shown along with the reloading segment 432 (offset for clarity). Other changes between the initial and fabricated material include the strain hardening behavior (433 and 435) and ultimate tensile strength (437 and 439). The changes in yield strength (427, 429), strain hardening (433, 435), and ultimate tensile strength (437, 439) may be inverse to what is shown in FIG. 8, depending on the type of manufacturing process.

Figure 9:
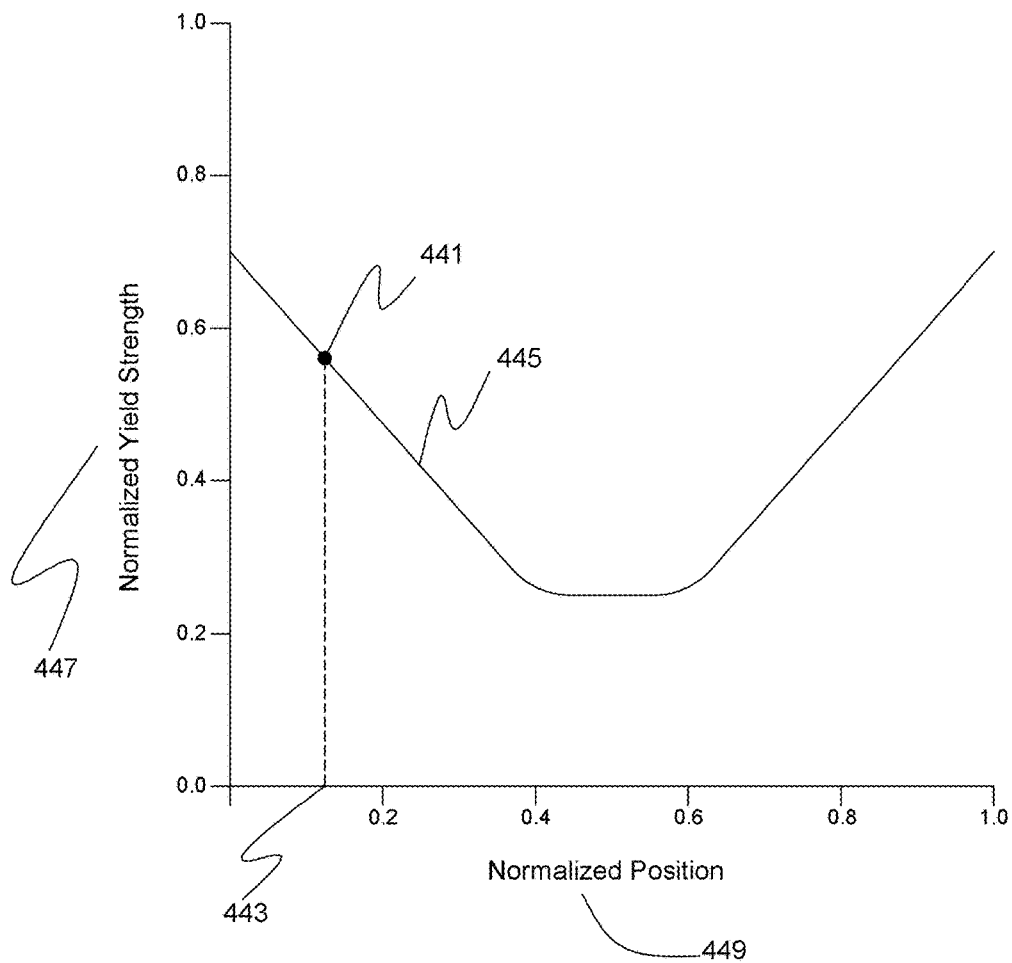
FIG. 9 is a schematic describing the relationship between local measurements along a material condition gradient in material properties.

FIG. 9 illustrates how a local measurement 441, obtained at a known location within a structural component 443, can be related to a material condition gradient 445. The shape and magnitude of the gradient 445 is dependent on dimensions of the structural component (FIG. 7) and the changes to the initial material from manufacturing processes (FIG. 8). Predictive algorithms are thus established to solve this reverse problem, where a unique solution will exist for a local measurement 441 obtained at a known location 543 for a given manufacturing process, geometry and initial stress-strain curve 419. These predictive algorithms can be verified and refined with contact mechanics data from field and laboratory testing. The prediction illustrated by 445 could be directly compared to contact mechanics measurements across the range of normalized positions. In the case of a cylindrical pipe, this could be a measurement of material conditions across the full thickness of the pipe wall; from the outer diameter to the inner diameter. The prediction illustrated by 445 will vary due to metallurgical variations including grain size, processing history, and chemistry. These data will need to be confirmed via appropriate laboratory or field testing. Improvement of the algorithm requires iterative refinement based on knowledge of metallurgical variations and contact mechanics measurements of material conditions through the wall thickness. In one embodiment, the local measurement 441 may be obtained at the exposed surface of the structural component through a contact mechanics test. In another embodiment, the local measurement 441 may be obtained within the structural component through another suitable method. The embodiment shown in FIG. 9 is for changes in normalized yield strength 447 as a function of normalized position 449 within the structural component. Normalized yield strength 447 is the ratio between the fabricated material yield strength 429 and initial material yield strength 427 that was shown on FIG. 8. Additional embodiments include other material properties such as strain hardening behavior, ultimate tensile strength, hardness, Young's modulus, and fracture toughness. The position may be through the thickness, or away from other features such as stress risers and welded seams. Normalized values allow for more general dimensionless predictive functions.

Figure 10A:
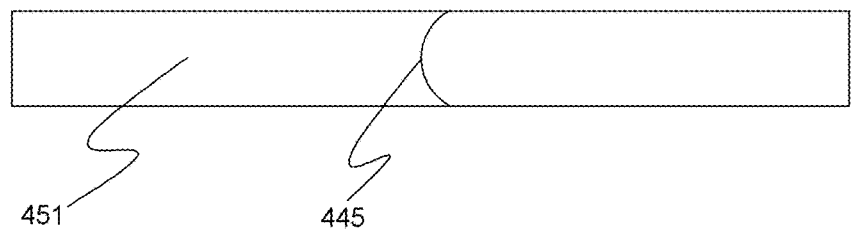
FIGS. 10A and 10B are schematics representing the use of a material condition gradient to obtain an effective property of a larger material volume measured through standard tests.
Figure 10B:
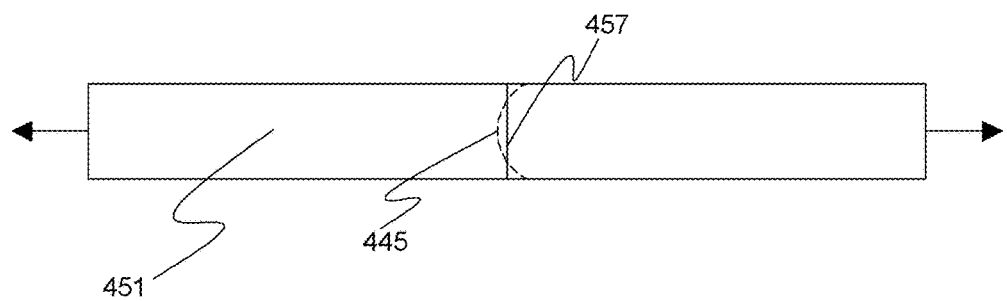

A material condition gradient 445 is shown within a structural component 451 in FIG. 10A. In this embodiment, the relevant position is through the thickness of a plate geometry. FIG. 10B demonstrates how a tensile test on the structural component 451 homogenizes the material condition gradient 445 to obtain an effective property 457 representative of a greater sample volume. This process considers the full distribution of material properties to obtain a single representative value. Effective properties may be obtained through a computational model of a tensile test of the structural component with a material condition gradient, analytical equations through homogenization theory, or other suitable means. Specific embodiments of the general approach for different manufacturing processes are given below.

Embodiments of Manufacturing Processes

Figure 11A:
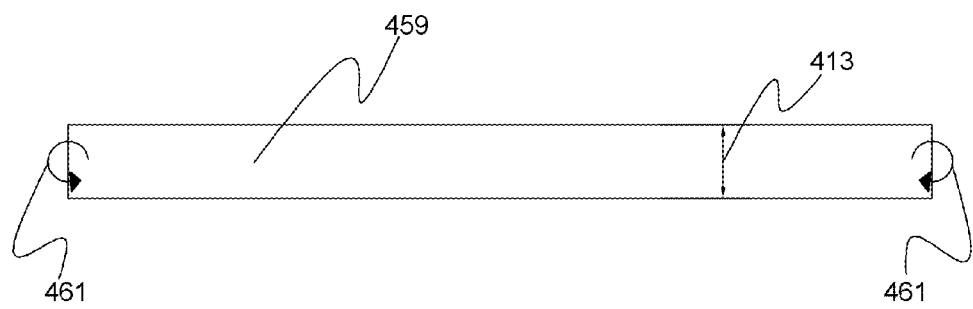
FIGS. 11A-C are schematics of gradients in material properties induced by permanent plastic deformation from mechanical loading.
Figure 11B:
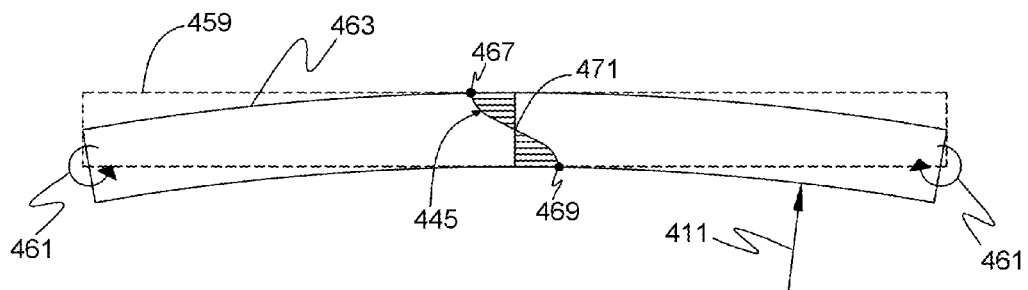
Figure 11C:
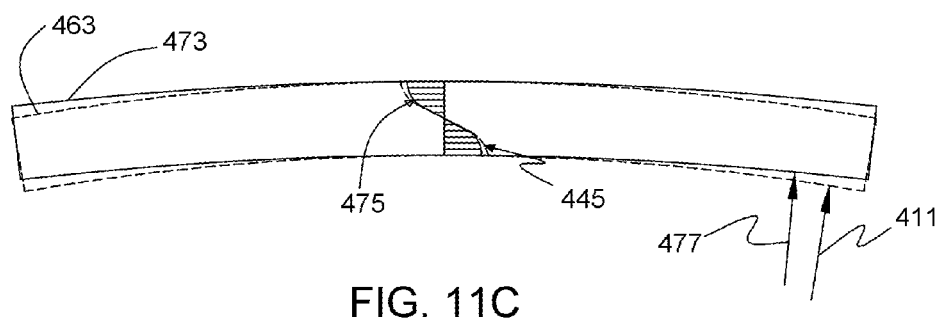
Figure 12A:
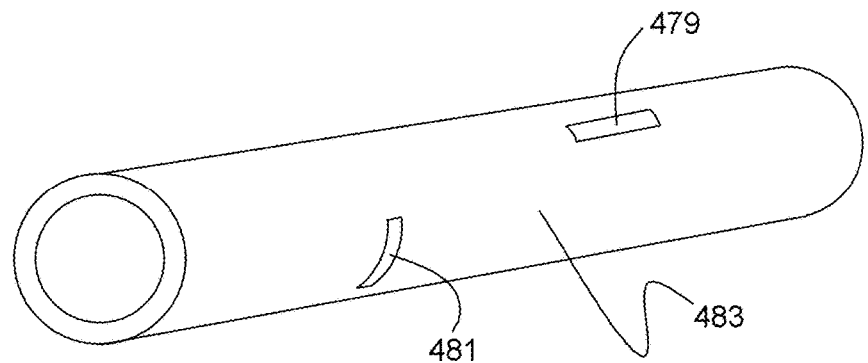
FIGS. 12A-C are schematics representing the processes associated with the standard test method for performing a standard tensile test for pipeline components.
Figure 12B:
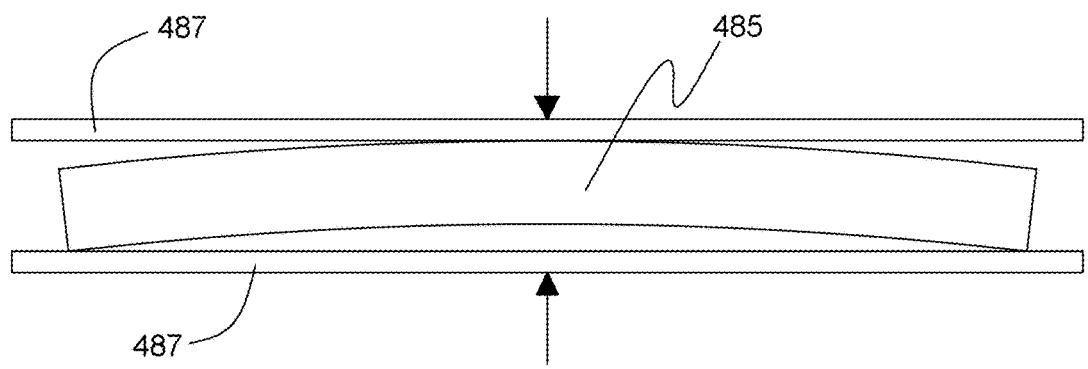
Figure 12C:
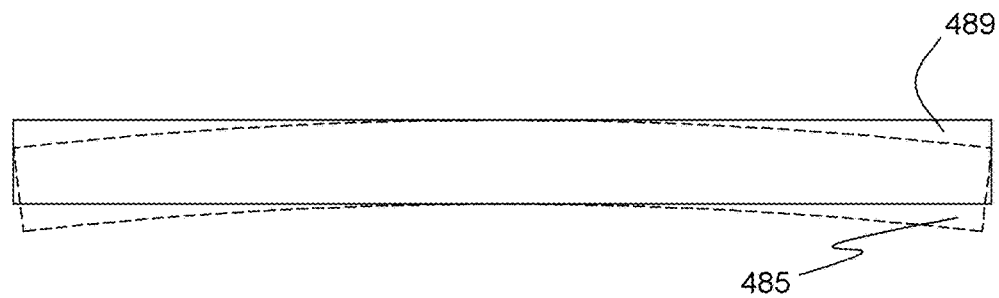

In one embodiment the algorithms are based on a computational model of permanent deformation from mechanical loads. An example is shown in FIG. 11, as the bending of an initially flat plate 459 with a specified thickness 413 into a curved shell or pipe geometry 463 with a known radius 411 (FIG. 11B). Bending may be accomplished through an applied moment 461, four-point bending test, contact with a die, or other suitable means. The bending induces a material condition gradient 445 that is dependent on the distribution of strain through the thickness 413. Material closest to the outer 467 and inner 469 diameters of the component have experienced the greatest change in material properties due to strain hardening, whereas almost no change has occurred near the mid-wall 471 where the material remains elastic or experiences the least permanent strain. If the bending load 461 is removed, elastic recovery 473 will occur resulting in a decrease in the measured material condition gradient 475 and increase in radius 477. An application of this embodiment is the extraction of tensile test coupons from fully formed pipes 483 which is shown FIG. 12A. Test coupons may be extracted from the longitudinal 479 or circumferential 481 direction of the formed pipe 483. These tensile coupons may undergo additional manufacturing processes when the initial curved geometry 485 is pressed to a flat plate 489 between two parallel plates 487 moving in the direction shown by the arrows in FIG. 12B. Flattening may occur through compression between rigid plates 487, a bending moment, or other suitable means. Flattening results in additional changes to material condition gradients because of the permanent shape change from the curved pipe section 485 shown in FIG. 7B and the flat plate 489 section shown in FIG. 12C. Although FIGS. 11 and 12 represent permanent mechanical deformation of pipe or shell geometries, other manufacturing processes are also applicable. These embodiments include, but are not limited to, rolling, stamping, forging, bending and shot-peening.

Figure 13A:
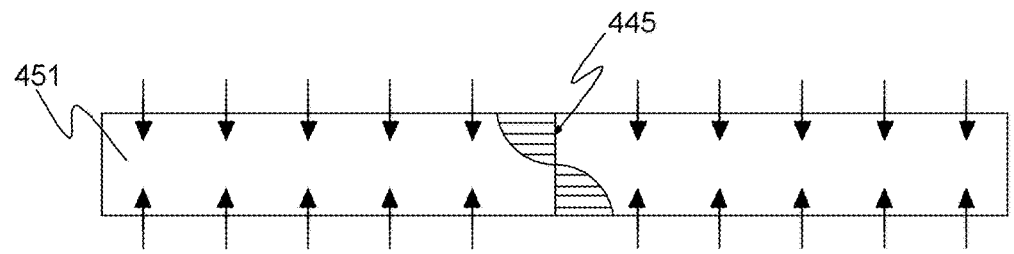
FIGS. 13A and 13B are schematics of gradients in material properties induced by thermal loads by adding or removing heat to a structural component.
Figure 13B:
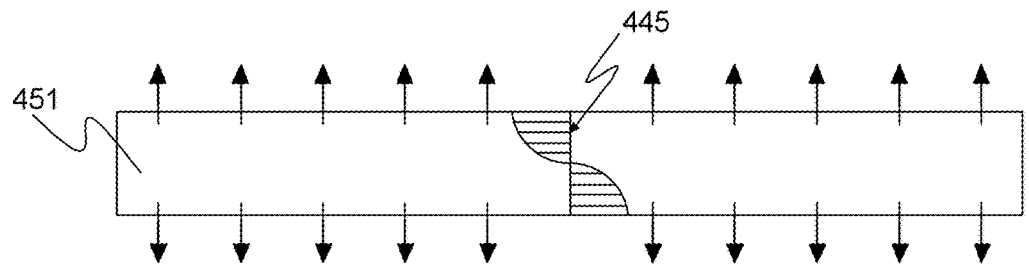

In another embodiment, thermal loads are considered to induce material condition gradients, as shown in FIG. 13. One embodiment of thermal loads is the input of heat, as shown by the arrows in FIG. 13A, to elevate the temperature of a structural component 451. This is performed at a controlled rate and to a desired temperature. Fast heating rates will result in material condition gradients 445 from differences in thermal expansion. Other gradients may arise due to microstructural changes from sustained heating at elevated temperatures. One embodiment of this process is annealing, resulting in a decrease in the yield strength and increase in strain hardening exponent of the initial material. Another embodiment of thermal loads is the removal of heat, as shown by the arrows in FIG. 13B, to reduce the temperature of a structural component 451. Similar to rapid heating, the rate of heat extraction may induce significant material condition gradients 445 in the material. An embodiment of this process is quenching. An embodiment that considers both rapid heating and cooling is the deposition of filler metal during the construction of a welded joint.

Figure 14:
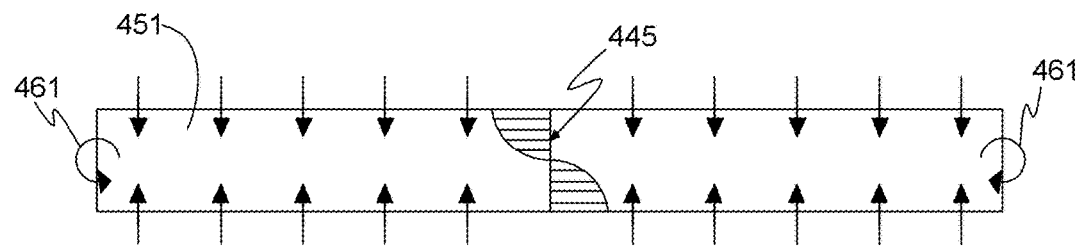
FIG. 14 is a schematic of combined effects from thermal and mechanical effects.

In another embodiment, the effect of mechanical and thermal loading is coupled as shown in FIG. 14. This results in material condition gradients through similar mechanisms observed in the prior embodiments, however, the magnitude of these changes will generally be reduced. An example of this embodiment includes hot rolling and forming.

Applications to Characterization of Cylindrical Tubing Manufacturing Normalization During the fabrication of welded tubing, a flat steel plate is cold formed to a cylindrical tube, with the opposing edges of the plate subsequently welded along a longitudinal or spiral (i.e. helical) seam. The cold forming process may be done through a continuous rolling process to progressively form a tube using internal and/or external rollers. Alternatively, cold forming may be accomplished through a series of mechanical presses featuring open U-shaped dies and closed O-shaped dies (UOE process). After forming and welding, additional finishing processes may include a heat treatment to "normalize" the steel at the seam location, heat treatment to "normalize" the entire tube, or cold-expansion of the tubing to approximately 1% of the tubing outer diameter. All of these manufacturing and finishing operations induce changes in the material condition gradient which effects the effective mechanical properties of the material that are measured during laboratory tensile tests on full wall thickness specimens.

The accurate measurement of effective properties for welded tubing with a contact mechanics test requires that the fabrication processes utilized are 1) identified with experiments and 2) considered in predictive algorithms that are developed through numerical models. The identification of fabrication processes for welded tubing is accomplished through a series of contact mechanics test at different locations around the tubing circumference. In one embodiment, a minimum of three contact mechanics tests are conducted to probe the response at the longitudinal welded seam, 180 degrees from the welded seam, and 90 degrees from the welded seam. Tests at the welded seam will provide a signature of the welding process used. In some embodiments, the hardness measured by the contact mechanics tester across the welded seam may show peaks associated with a heat-affected-zone (no normalization), a large or small plateau of increased hardness (low frequency or high frequency welding processes, respectively) or no noticeable change in material hardness (normalization). Contact mechanics tests at 180 degrees and 90 degrees from the welded seam are tests performed on base metal, however, 180 degrees from the seam experiences the largest cold forming strains and therefore a larger absolute value of hardness. In one embodiment, the ratio or absolute difference between hardness values at 180 and 90 degrees from the seam are used to identify whether cold forming, or cold forming and cold expansion were used during fabrication. Cold expansion can be identified if the contact mechanics tests at 180 and 90 degrees from the seam have very similar hardness values, because cold expansion homogenizes the material property gradient in tubing. If all three of these test locations have very similar hardness values, it is indicative that the entire pipe has been normalized.

A pipe that has more homogenized material condition gradients requires only a small, if any, correction to the surface value measured during a contact mechanics test. Therefore, identifying the presence of normalization or cold expansion will utilize a different set of algorithms for establishing the effective properties. For pipes that have only experienced cold forming, a significant material condition gradient exists and the surface property will have to be corrected. These corrections are performed through algorithms that are developed through simulations of the fabrication processes employed in the welded tubing. These algorithms are developed prior to conducting experimental contact mechanics tests by considering a wide range of structural component geometries and fabrication process parameters. In one embodiment, the hardness measurements are used as inputs into algorithms to predict an effective yield strength or ultimate tensile strength, based on the identified fabrication processes. In another embodiment, the algorithms also provide an estimate of the cold expansion performed to the tubing based on the differences in hardness values around the tubing circumference. In another embodiment, the fabrication processes are identified from pipe material specifications that were maintained by the owner of the operator. In another embodiment, a historical database is used to improve determinations of fabrication processes based on the year of fabrication and manufacturing vendor of the company, which reflects the methods used with changing technologies.

Detailed Description of Apparatus

Stylus

The stylus 20 profile that engages with the substrate 16 is what influences the substrate 10 response. As such, we can differentiate between different types of styluses 20 based on their produced response. Styluses intended to generate primarily permanent or time-dependent deformations in the substrate utilize a ploughing action. Referring again to FIG. 5A, according to an exemplary embodiment, the stylus 20 has a conical geometry with a total included angle 22 between about 120° and about 170°, which corresponds to about 5° to about 30° of cone surface elevation with respect to the substrate surface 16. The included angle 22 of the stylus 20 has an effect on the substrate contact response 12 during testing, and is selected based on the contact conditions, such as friction. The stylus 20 may have other types of geometries (not shown in the figure). For example, the stylus may be pyramidal, spherical, a wedge, or any other suitable geometries. For example, the stylus may have any suitable bottom cross-section, such as a triangular cross-section. In one example, the stylus 20 may be any commercially available shape, including Vickers, Rockwell, etc. The stylus 20 may be formed of any material with a sufficient hardness to penetrate the substrate 10 and form a deformation 11 in the substrate 10, including, but not limited to, silicon, titanium oxide, sapphire, diamond, and steel with an appropriate coating or surface treatment.

Figure 57:
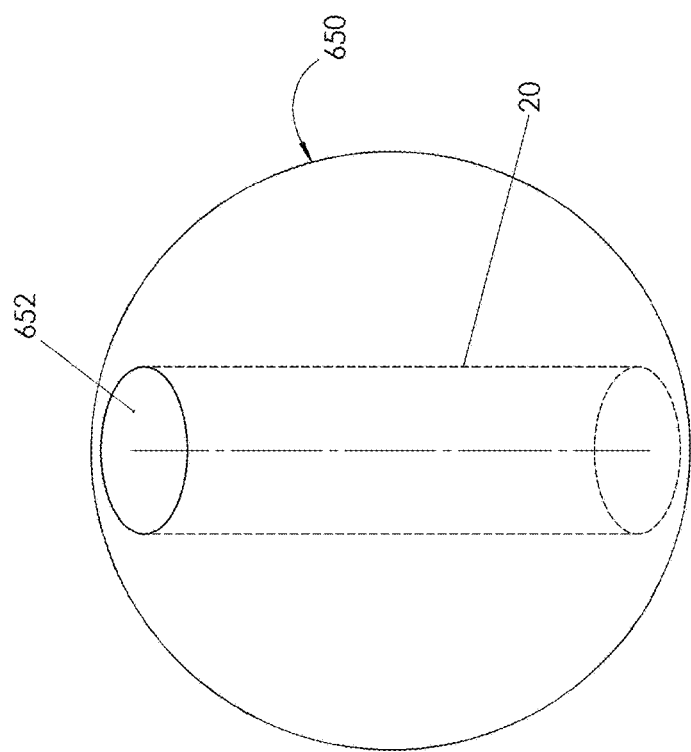
FIG. 57 depicts a schematic side view of stylus which was manufactured from a spherical ball bearing according to embodiments of the present invention.

The stylus may also be formed from a product of sufficient material quality which has been manufactured for an originally different purpose. For example, when the stylus tip requires a precision spherical diameter, a silicon carbide ball bearing of sufficient material grade and surface finish may be cut, ground, and shaped to produce the desired stylus geometry with the original bearing surface left untouched at one end. The process extracts a cylindrical section with a central axis intersecting the central point of the original sphere. FIG. 57 illustrates the process by showing the original bearing geometry 650 compared to the resulting stylus 20 with the original bearing surface 652.

Figure 15:
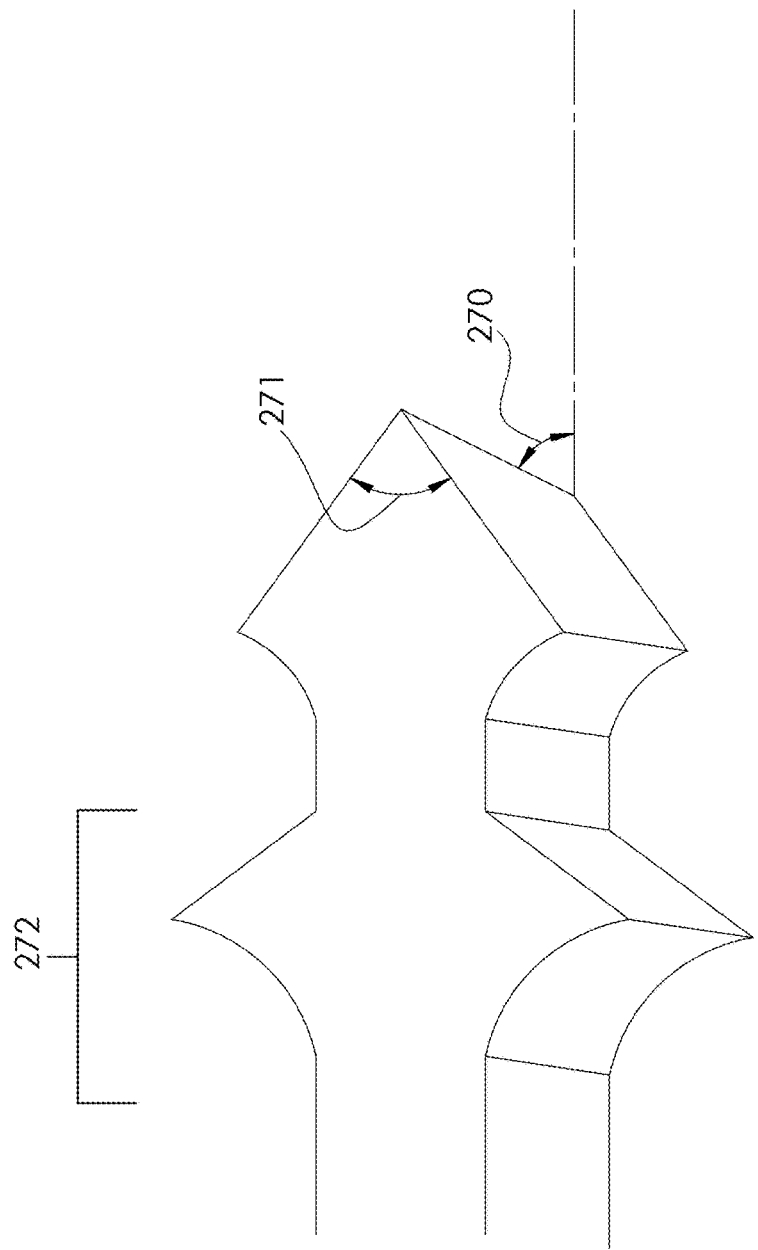
FIG. 15 is a schematic perspective of a stylus having a wedge-shaped profile.
Figure 16:
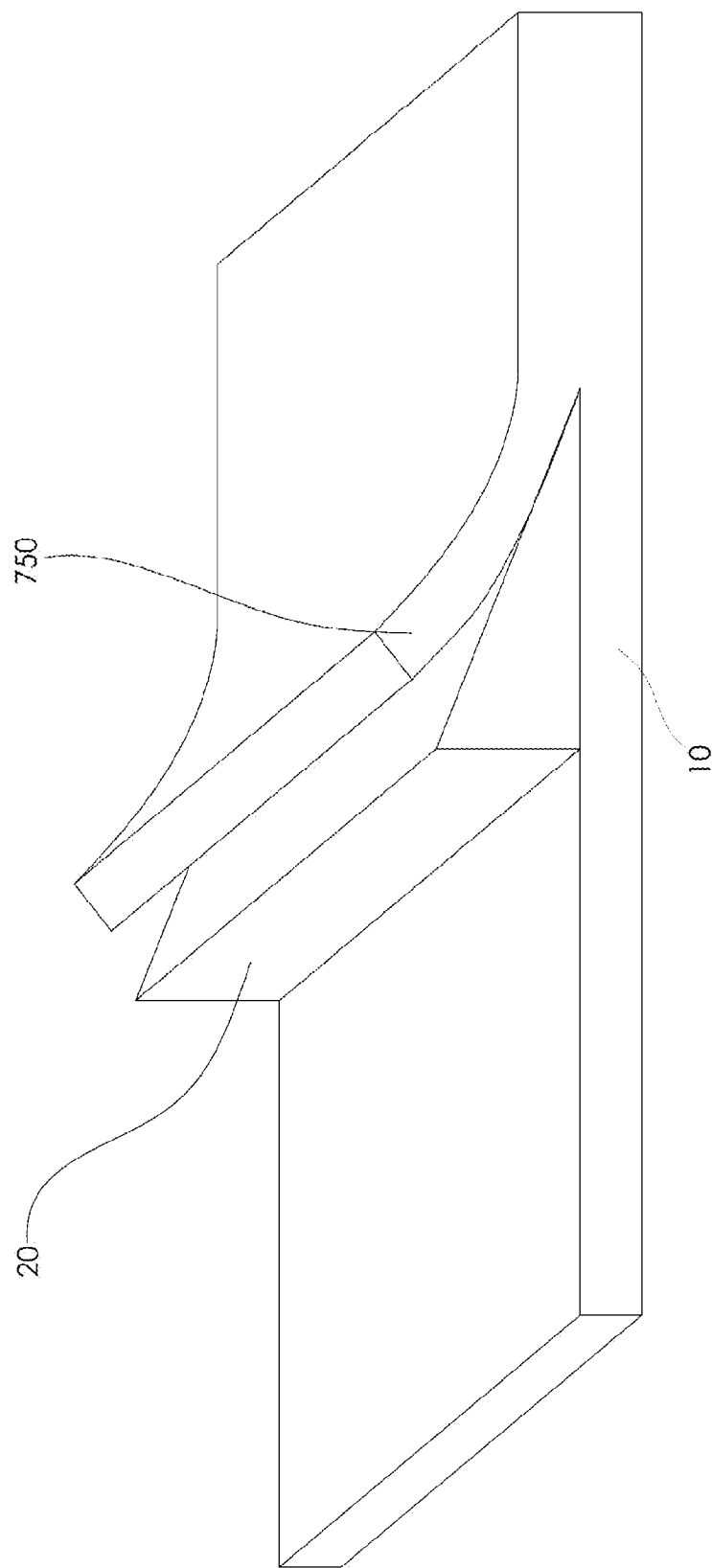
FIG. 16 is a schematic perspective view of a stylus with a wedge-shaped, cutting tool profile engaging with the substrate.

FIG. 15 shows a wedge stylus configuration. Preferably, the stylus includes a blunted front as indicated by angles 270 and 271 to cause the plastic flow of the material without the formation of chips or the creation of dead-zones (areas where the material remains stationary with respect to the stylus) and, further downstream, has the ability to grab the material and push it away using a wedge 272 from the substrate contact response centerline to create enough biaxial tension to create the deformation. In one embodiment, as shown in FIG. 16, the wedge stylus 20 may be simplified to near triangular in order to use advanced machining techniques such as focused ion beam milling instead of other techniques such as additive manufacturing by laser sintering or other lithography techniques. A wedge stylus configuration will typically be shaped to enforce a machining or non-ductile response in the substrate 10, resulting in chip or ribbon formation 750.

Embodiments of Alignment Mechanisms

Figure 17:
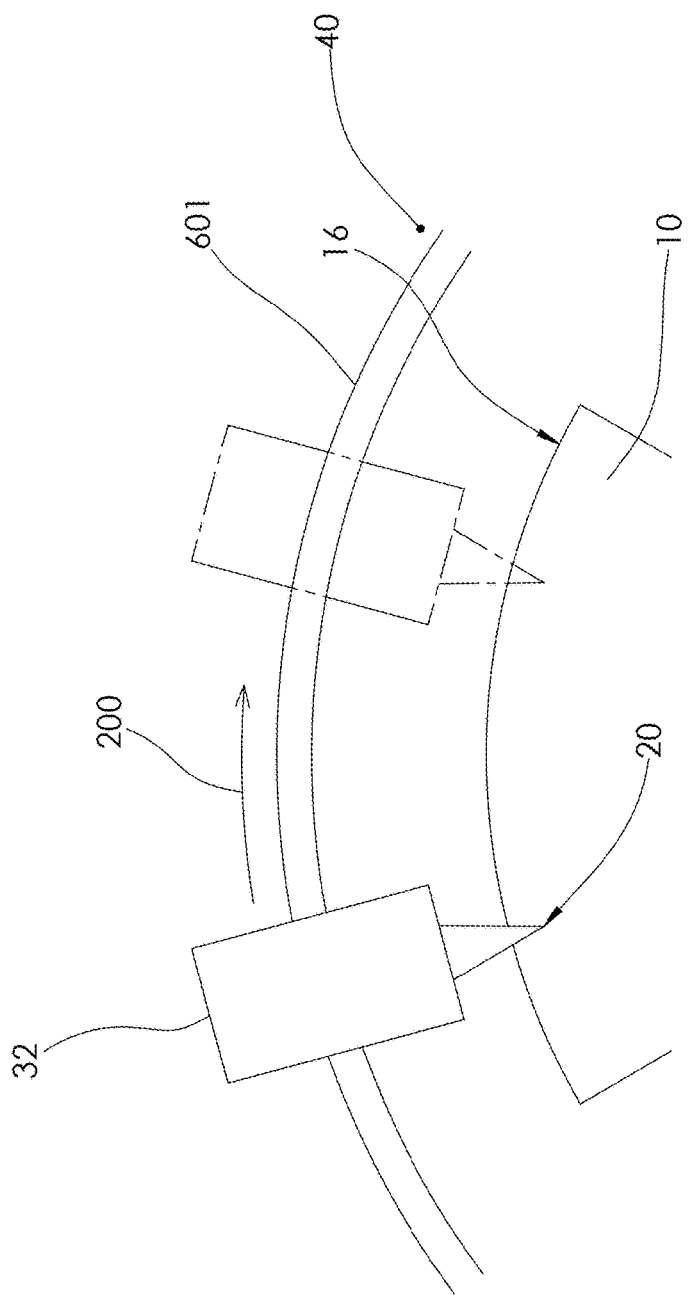
FIG. 17 is a schematic side view of a contact mechanics test apparatus and path referencing alignment mechanism according to embodiments of the present invention.
Figure 18:
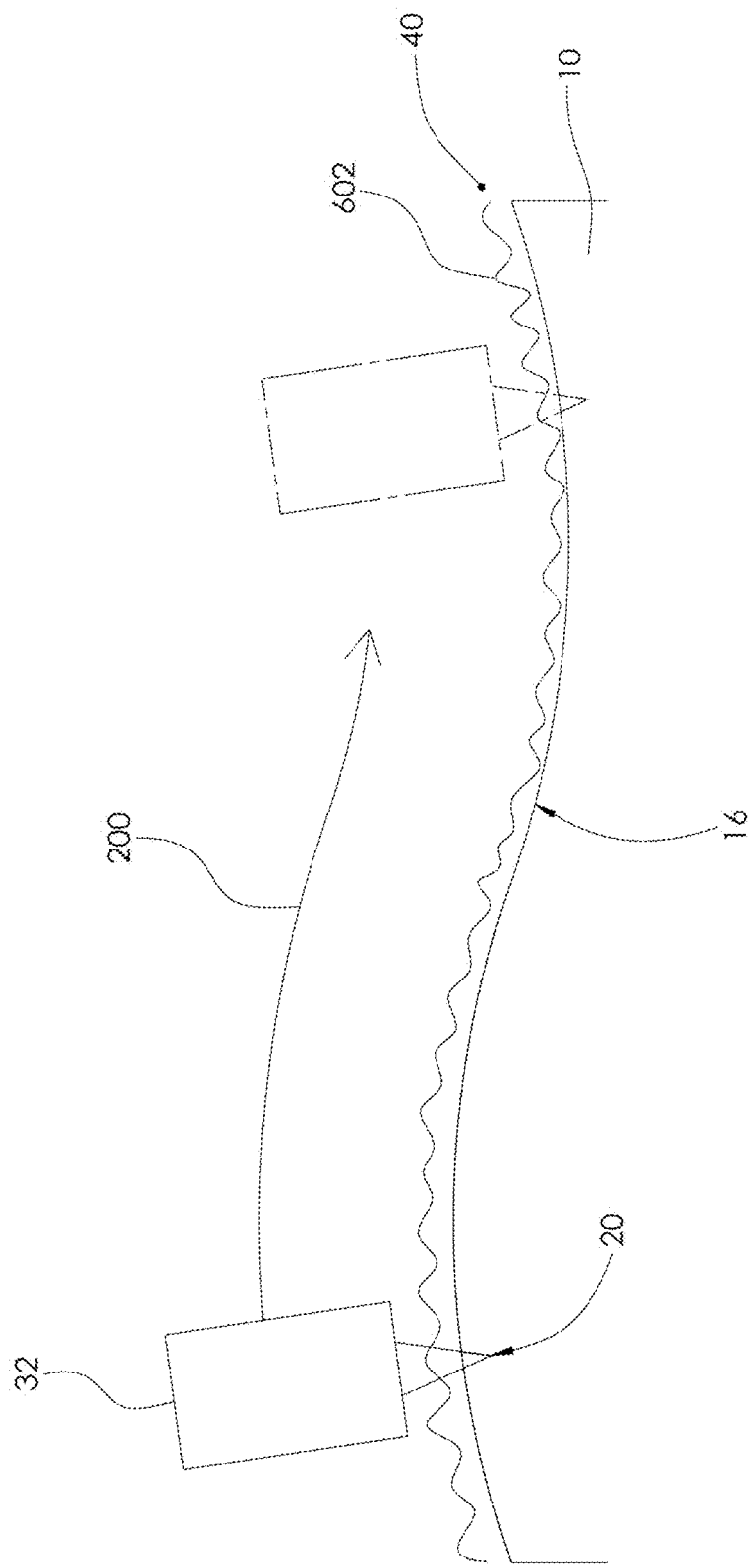
FIG. 18 is a schematic side view of another exemplary contact mechanics test apparatus and path referencing alignment mechanism according to embodiments of the present invention.

One category of embodiment is a path referencing system that is preset as part of the frame engagement mechanism before the contact mechanics test and guides the movement of the stylus to ensure that it maintains the desired local angular orientation with the substrate surface. In this category of embodiments, the core engagement can be contiguous with the frame. One embodiment of a path referencing alignment mechanism is a set of curved tracks that are fairly stiff and selected, for example, to be coaxial with the radius of a pipe. For a round pipe, the path referencing alignment mechanism can also be a track that has points of contact with the substrate surface and conforms and is normal to the local substrate surface. In the latter case, the surface can have multiple curvatures. FIG. 17 shows a possible embodiment of the alignment mechanism 40 where a pre-set track 601 is configured to the geometry of the substrate surface 16 and allows for alignment of the core 32 (and stylus 20). In this embodiment, the track is rigidly attached to the substrate 10 of the component being tested. In another embodiment, as seen in FIG. 18, the conforming track 602 contacts the substrate surface 16 to match the geometry, but the contact does not require attachment that may damage the substrate 10. In both embodiments, the direction of movement 200 of the core 32, and therefore stylus 20, is maintained by the respective path referencing embodiments of the alignment mechanism 40.

Detailed Description of Contact Referencing

Referring now to FIGS. 20-27B, a testing apparatus 30 is shown in detail according to several exemplary embodiments. As shown schematically in FIGS. 20 and 21, the testing apparatus 30 includes a core 32 to which the stylus 20 is coupled. The core 32 provides structural support for the apparatus by accommodating reaction forces on the stylus 20 from engagement with the substrate 10 and applied loads from the stylus engagement mechanism 41 and core engagement mechanism 36. During a frictional sliding test, the stylus 20 is moved relative to the substrate surface 16 to deform the substrate 10 by applying an engagement load to the stylus 20 with a stylus engagement mechanism 41 and applying a transverse load to the core 32 with a core engagement mechanism 36. During an indentation test, the stylus 20 is moved relative to the surface 16 of the substrate 10 to travel to different testing locations as part of a series of one or more indentations. According to an exemplary embodiment, the core engagement mechanism 36 is coupled to the core 32 with a transfer module 35, shown as a mechanical link. The core engagement mechanism 36 may have a normal force actuator 37 that applies a normal force to the core 32 to maintain contact between the contact referencing alignment mechanism and the substrate surface 16. The testing apparatus 30 may be coupled to the substrate 10 by a frame engagement mechanism 321. As the deformation in the substrate 10 is formed by the stylus 20, the testing apparatus 30 simultaneously measures the substrate contact response with a substrate monitoring device 39 coupled to the core 32. The contact mechanics test and substrate contact response 12 measurements need not occur simultaneously. In one embodiment, these two processes may take place sequentially. In one embodiment, regardless of whether the two processes take place simultaneously or sequentially, the two processes are carried out by one single apparatus. Another embodiment involves multiple deformations being produced simultaneously with measurement of the substrate contact response which may occur simultaneously or sequentially.

Referring to FIGS. 21-26, a core 32 enables reliable monitoring and/or control of the position and principal axis 21 of the stylus 20 at a desired local angular orientation 23 to the substrate surface 16 of the substrate 10 at the same time that the deformation is being made. This process is referred to as contact referencing, and represents one embodiment of the alignment mechanism. The contact referencing alignment mechanism is configured to operate in either a monitor mode or a control mode. In the monitor mode, the core 32 allows the testing apparatus 30 to establish the local angular orientation of the principal axis of the stylus 20 under a predetermined applied engagement load with the substrate surface 16, allowing for a load control experiment. In the control mode, the core 32 allows the testing apparatus 30 to form a deformation of a constant and known depth within the substrate 10, and to detect the reaction force from engagement of the stylus 20 with the substrate 10, allowing for a displacement control experiment. In either the monitor mode or the control mode, testing apparatus 30 induces deformation in the substrate 10, resulting in a characteristic substrate contact response 12 which may be utilized with reverse algorithms to predict mechanical properties.

Embodiments of Contact Referencing

Figure 32B:
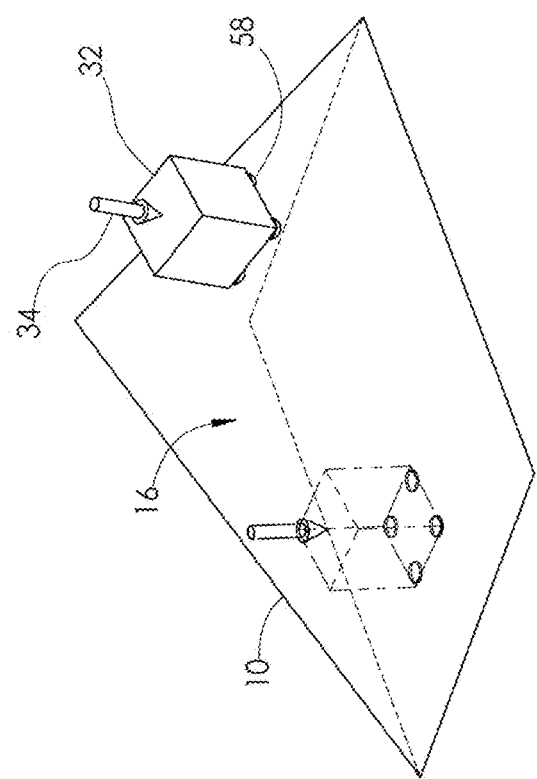
FIGS. 32A and 32B are schematic perspective views of a contact mechanics test apparatus and contact referencing alignment mechanism according to an exemplary embodiment.
Figure 32A:
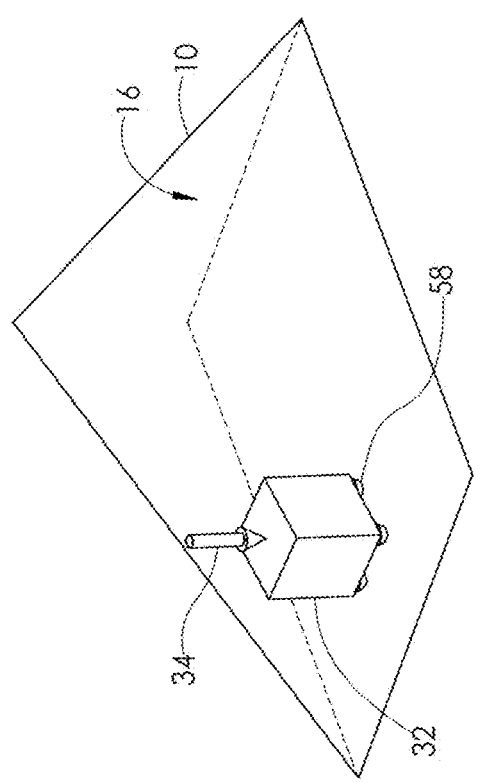

Embodiments include setting the local angular orientation of the stylus 20 based on a survey of the substrate surface 16 profile. This can be done with the use of contact floats 58, as shown in FIG. 32A and FIG. 32B. The floats are in contact with the substrate surface 16 and cause the core 32 (and stylus 20) to automatically re-orient with respect to the local substrate surface. As the local angular orientation of the stylus 20 is adjusted, the direction of the engagement load provided by the stylus engagement mechanism 41 is also modified. As discussed in detail below, the contact referencing may be implemented using floats.

Figure 23:
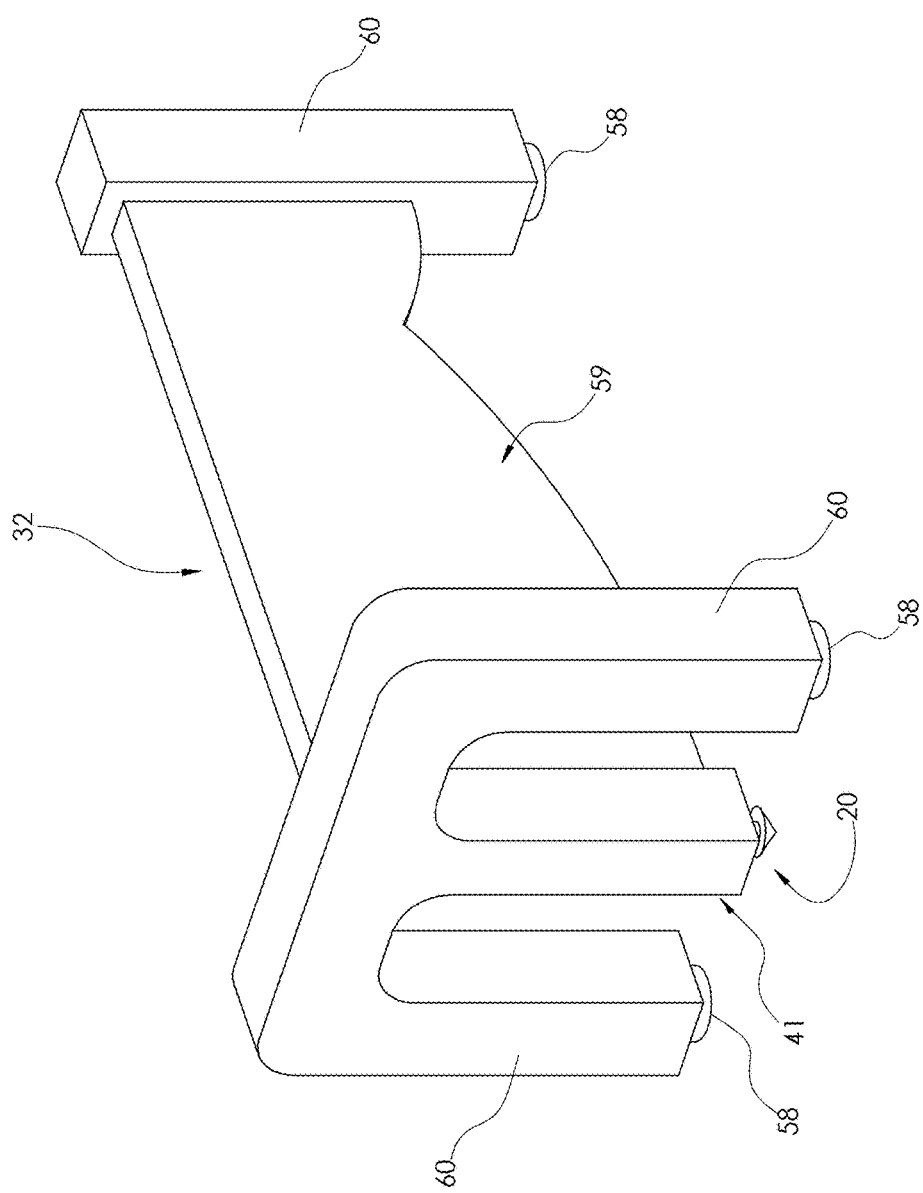
FIG. 23 is a schematic perspective view of an exemplary contact referencing alignment mechanism for the apparatus of FIGS. 1 and 19 according to embodiments of the present invention.
Figure 24:
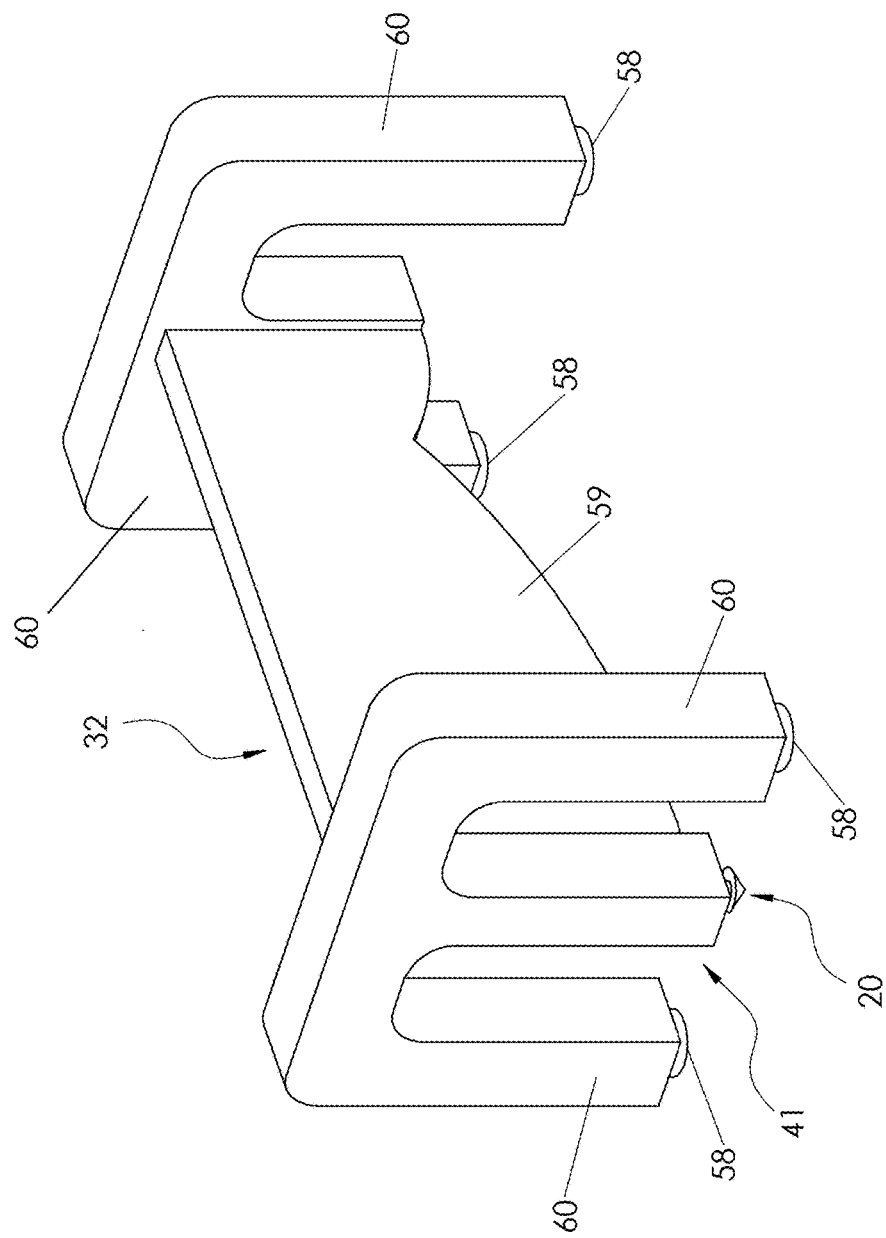
FIG. 24 is a schematic perspective view of another exemplary contact referencing alignment mechanism for the contact mechanics testing apparatus of FIG. 1 according to embodiments of the present invention.

According to exemplary embodiments, a core 32 may comprise two floats 58 (FIG. 22), three floats 58 (FIG. 23), four floats 58 (FIGS. 24 and 27A), or more, which contact the substrate 10 outside of the location being deformed by the stylus 20 in order to perform contact referencing alignment. Contact of the floats 58 with the substrate 10 is accomplished by applying sufficient load to the core 32. For a two float 58 alignment mechanism, the floats 58 contact the substrate 10 at the same plane as engagement of the stylus 20 with the substrate 10 in the length direction of deformation. For a core 32 comprising three or more float 58, additional floats are included either forward or rearward of the stylus 20 (e.g., in the direction of the deformation). In one embodiment, the core 32 may include a single member 60 positioned in line with the trajectory of the stylus 20 as shown in FIG. 24. In another embodiment, the core 32 may include two or more members 60 positioned rearward from the stylus 20 as shown in FIG. 25. The members 60 may be in line with the trajectory of the stylus 20, or they may be positioned laterally, to the side of, the trajectory of the stylus 20. The rearward members 60 and the members 60 positioned on either side of the stylus 20 may be utilized to reference the substrate surface 16 in the direction of the trajectory of the stylus 20. In another embodiment incorporating three or more floats 58, the span length between the stylus 20 and the front floats 58 and the span length between the stylus 20 and the rear floats 58 may be set at a predetermined ratio. This configuration allows for the correction of an irregular substrate surface with substantial curvature in the length direction and contact width 24 direction of deformation. For these embodiments, the floats 58 and stylus 20 are coupled by the core 32 to allow for the core 32 to be utilized in a monitor mode to perform load control or control mode to perform a displacement control experiment.

Referring to FIG. 22, the elevations 46 of the coupling members 60 of a two float 58 contact referencing alignment mechanism 40 are shown on either side of the stylus 20. In control mode, the elevations 46 sets the relative offset between the stylus 20 deforming the substrate 10 and the floats 58 contacting the substrate 10 outside of the area being deformed, allowing for a constant and known substrate contact response depth 26 for a displacement control experiment. The same principles apply to contact referencing systems with more than two floats 58, where contact between the multiple floats 58 and substrate 10 sets the penetration depth 26 of the stylus 20. In monitor mode, the offset between the stylus 20 and floats 58 is not maintained, as the stylus 20 may translate in the direction of the penetration depth 26 based on the load applied by the stylus engagement mechanism 41 and the reaction force with the substrate 10 to perform a load control experiment. For this embodiment, the alignment mechanism 40 controls the local angular orientation but not the depth of the stylus 20.

Cores 32 comprising 2 or more floats 58 in either monitor or control mode may allow for correction of the local angular orientation of the principal axis of the stylus 20 with the substrate 10. For high load applications, the testing apparatus 30 is sufficiently rigid to transform the contact force between the substrate 10 and the floats 58 into a rotation of the core 32. Local angular orientation may also be set by the predetermined lengths between the floats 58 and stylus 20 in the length and contact width 24 directions of deformation. In another embodiment, the local angular orientation is set by a transfer module 35 attached to the core engagement mechanism 36 that allows for low friction torsional rotation of the rigidly connected core 32 and core engagement mechanism. In low load applications, where the corrective torque provided by the core engagement mechanism to the core 32 is insufficient to provide local angular orientation correction, the core 32 may only provide elevation correction. Low load applications may include applications in which the contact force between the substrate 10 and the floats 58 is not translated into a rotation of the core 32. Local angular orientation correction may not be needed when the substrate 10 and stylus 20 are set perpendicular or close to perpendicular (e.g., to within a few degrees of perpendicular) depending on the accuracy needed. Alignment using elevations 46 may reference the substrate surface 16 in a direction transverse to the direction of the deformation.

The floats 58 may include electrical contact indicators or contact load indicators 57 such that an error message may be provided if contact between the floats 58 and the substrate surface 16 is lost. The floats 58 may establish contact with the substrate surface 16 through frictional sliding, rolling contact, air flow or other contact mechanics mechanisms. The contact between the floats 58 and the substrate surface 16 may be elastic, although in some instances plastic contact may be possible. The floats 58 may be adjustable to allow for a change in the deformation depth. For example, in one embodiment, the floats 58 may be movable relative to static members 60 that are part of the core 32. The floats 58 may be movable in a direction normal to the substrate surface 16. Other directions of movement are also possible.

Figure 28B:
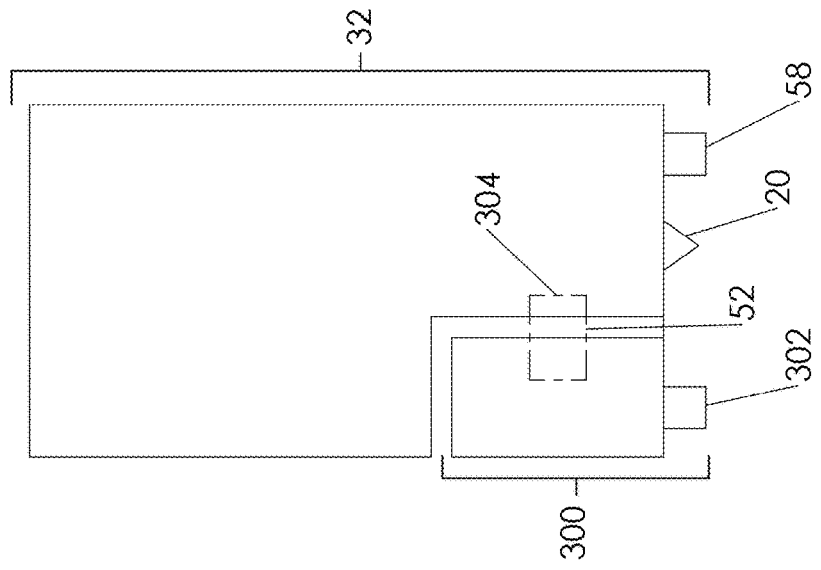
FIGS. 28A and 28B are schematic views of an exemplary rocking float subassembly according to embodiments of the present invention.
Figure 28A:
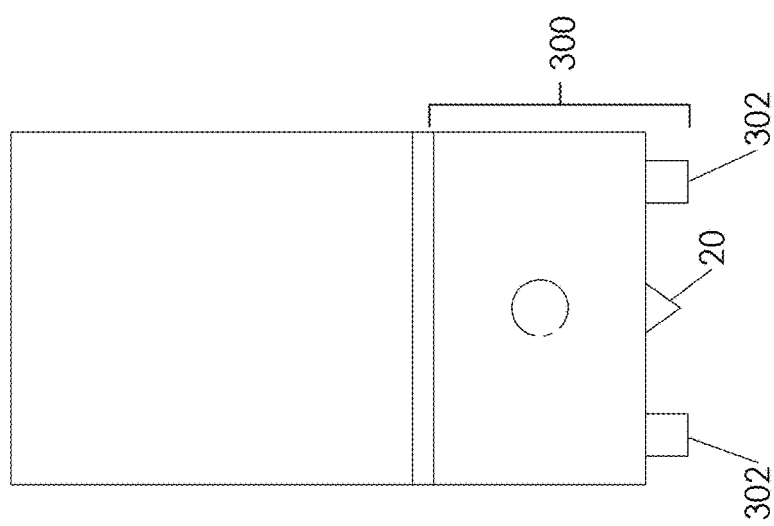
Figure 29B:
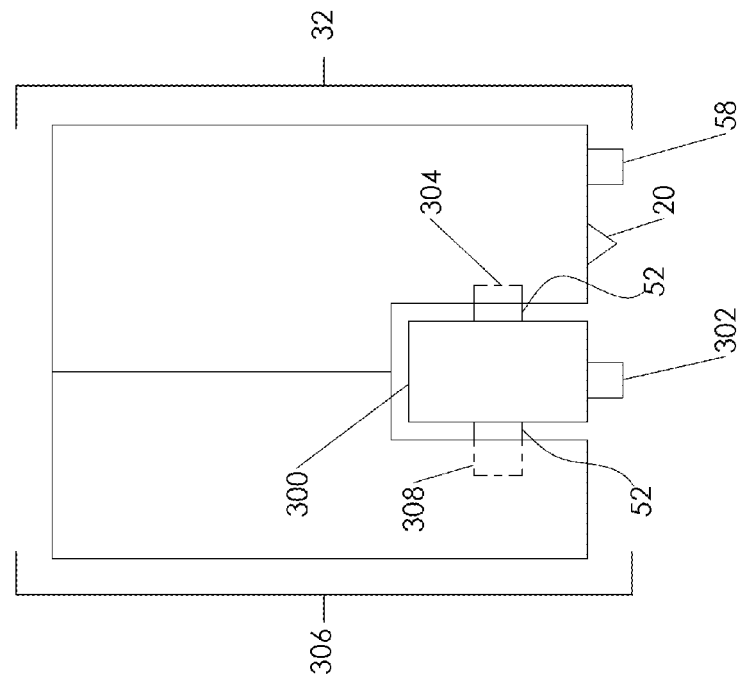
FIGS. 29A and 29B are schematic views of an exemplary rocking float subassembly according to embodiments of the present invention.
Figure 29A:
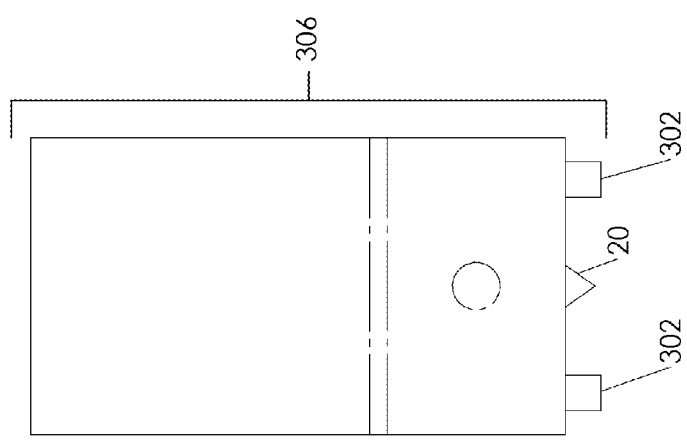
Figure 31C:
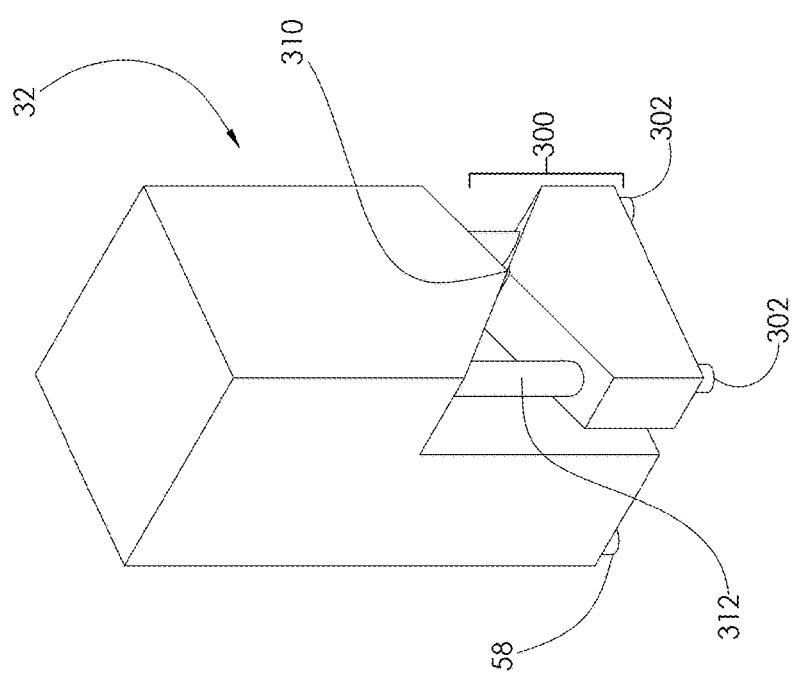

Two possible embodiments of a core configured for contact referencing alignment will include either three or four floats. The benefit to three floats is that, with sufficient normal force, all three will remain in contact with the substrate surface regardless of surface topography. However, mounting three floats symmetrically without interfering with the path of the frictional sliding test, which can cause premature surface deformation, or compromising stability, which may result in the core tipping, is a challenge. A core with four floats does not have this concern, but will have more difficulty keeping all floats in contact with the substrate surface at all times during a contact mechanics test, due to slight variations in float height or substrate surface topography, which can cause the core to suddenly rock between floats. One possible solution is to mount two of the four floats such that the effective point of contact is the average between them, determined mechanically. FIGS. 28-23 show embodiments of the core 32 with a stylus 20 and two floats 58, and a rocking float subassembly 300, which includes two additional independent floats 302. The rotation of the rocking float subassembly 300 is capable of keeping both independent floats 302 in contact with the substrate surface (not shown) during a frictional sliding test. FIG. 28 shows an embodiment which includes an on-core attachment 304 to support the rotational attachment 52. FIG. 30 shows an embodiment which includes an off-core component 306 with an off-core attachment 308, which the rocking float subassembly 300 and rotational attachment 52 can mount to independently of the core 32. FIG. 31 shows an embodiment that utilizes both an on-core attachment 304 and off-core component 306 with off-core attachment 308 to significantly increase the stiffness of the rocking float subassembly 300 and rotational attachment 52. FIG. 31 shows an embodiment which includes a pivot attachment 310 and two rocking float stabilizers 312, though only one rocking float stabilizer 312 may also be used.

Embodiments of Scanning Referencing

Figure 33:
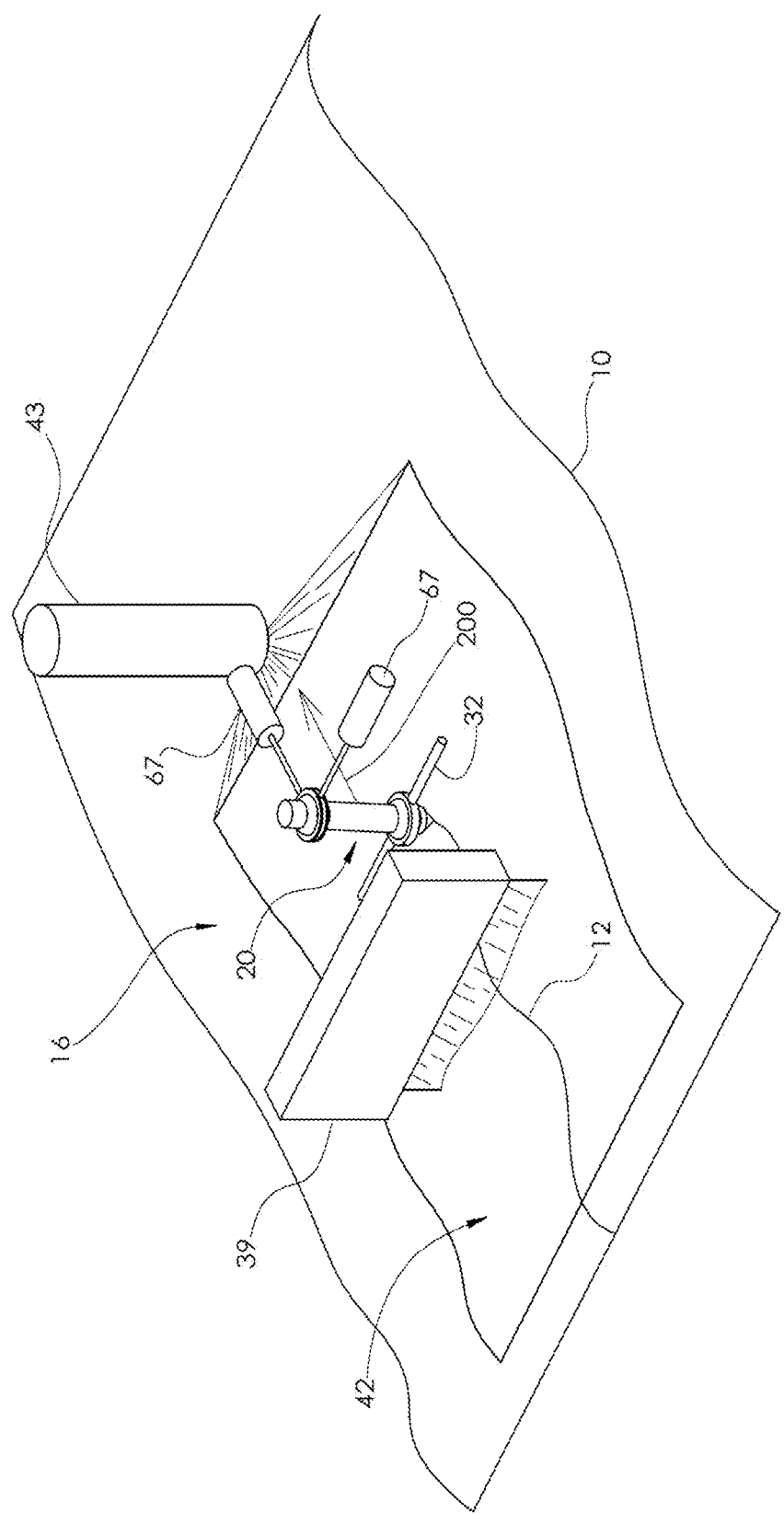
FIG. 33 is a schematic perspective view of an exemplary scanning referencing alignment mechanism for the contact mechanics testing apparatus of FIGS. 1 and 19 according to embodiments of the present invention.

Another embodiment for orienting the stylus, as shown in FIG. 33-34B, performs a survey of the substrate surface 16 to gather surface topographic measurements using a topographic probe 43 and then actuate the core 32 (and stylus 20) using one or more translation actuators 67 as the stylus 20 travels along the substrate surface 16. The topographic probe 43 can be mechanical, optical, and/or electromagnetic. The surface topographic probing can be done before and/or during the contact mechanics test. The core 32 is actuated by the core engagement mechanism 36 to rotate around one or two axes of rotation set approximately in plane with the local substrate surface 16 using information obtained from the scanned substrate surface 42. The translation actuator 67 can be mechanical, hydraulic, electrical, or magnetically actuated. The selection depends greatly on the size-scale required for the testing objective.

Figure 58:
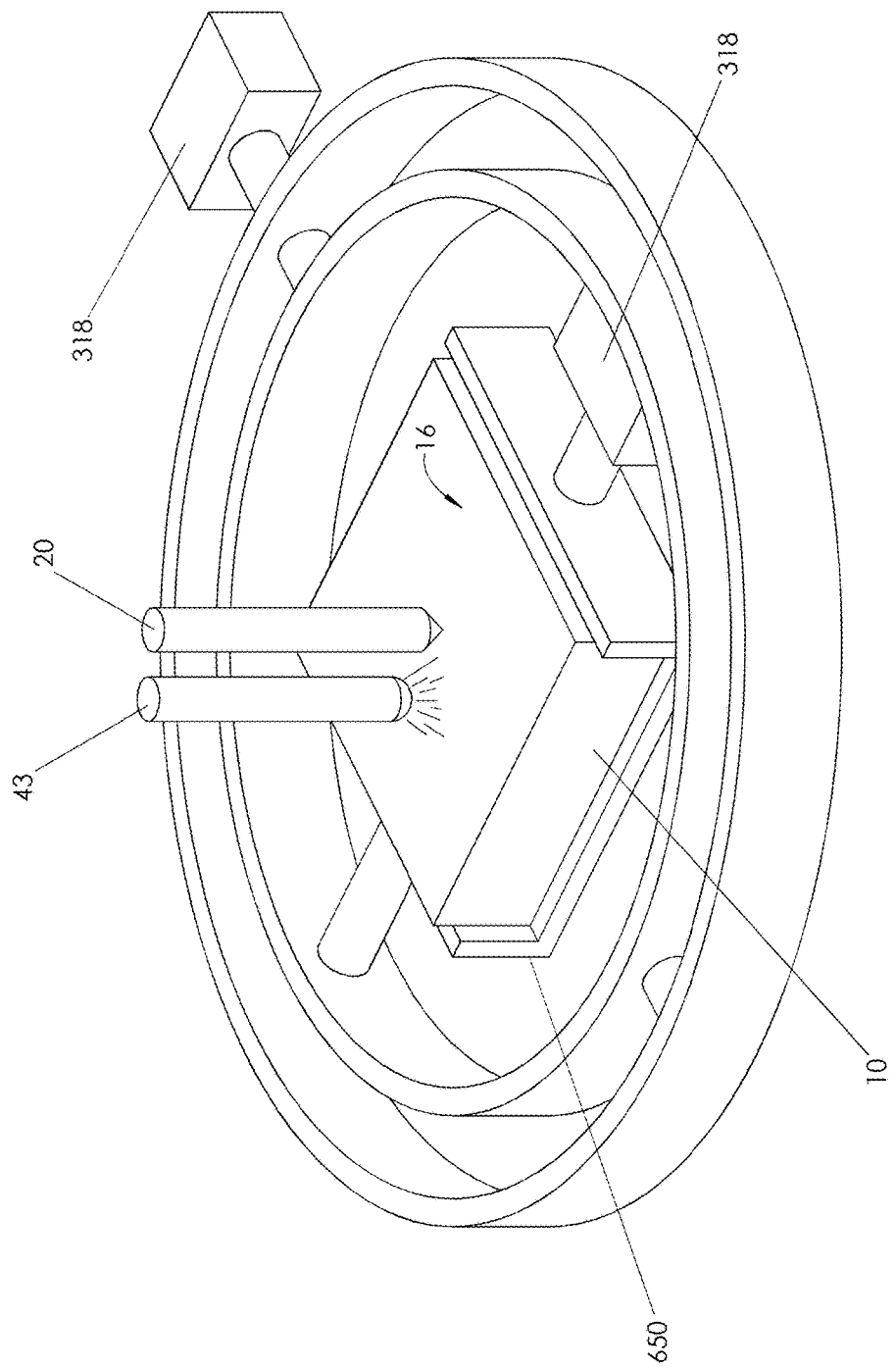
FIG. 58 is a schematic perspective view of an exemplary scanning referencing alignment mechanism for the contact mechanics testing apparatus of FIGS. 1 and 19 according to embodiments of the present invention.
Figure 59:
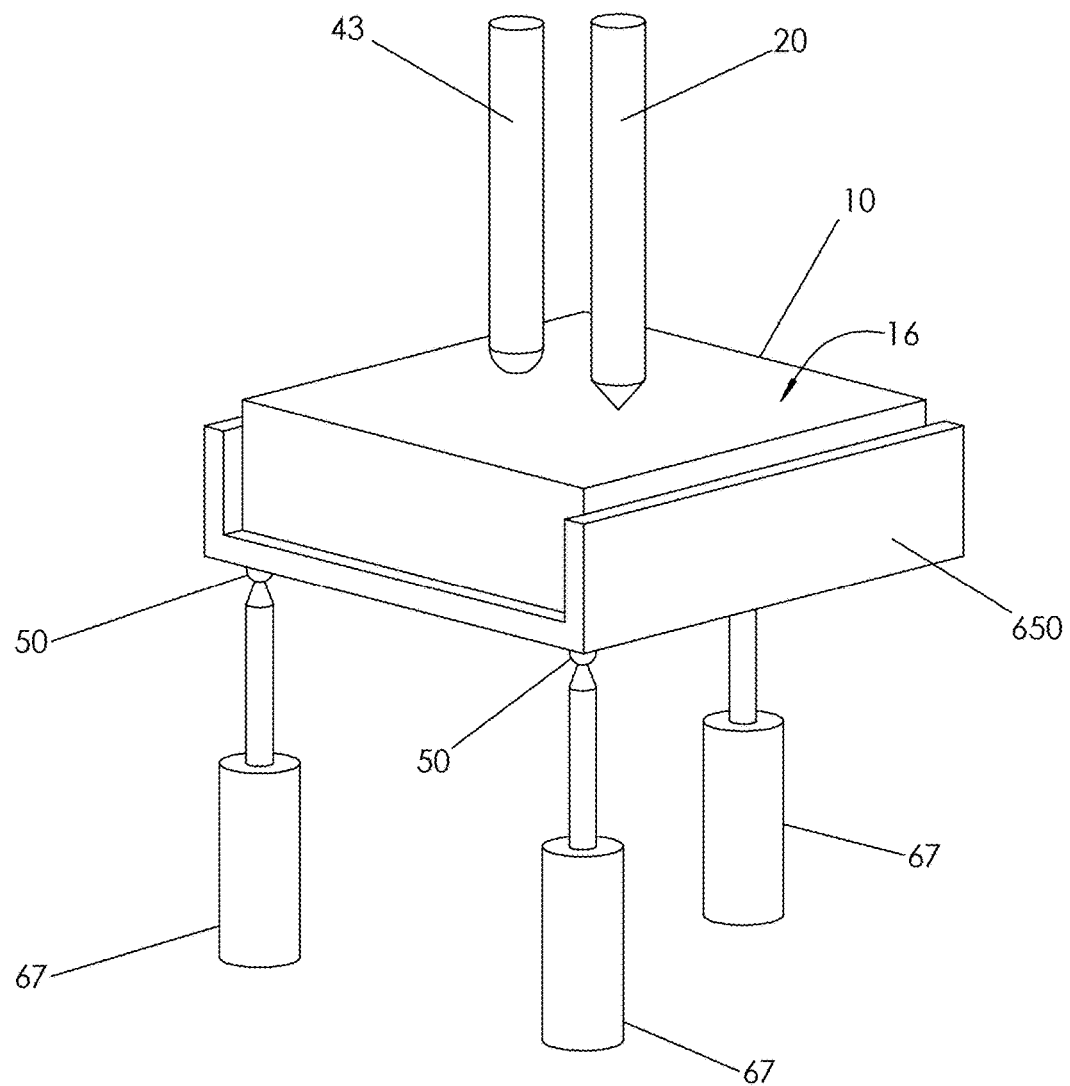
FIG. 59 is a schematic perspective view of an exemplary scanning referencing alignment mechanism for the contact mechanics testing apparatus of FIGS. 1 and 19 according to embodiments of the present invention.

In another embodiment of scanning alignment, shown in FIGS. 58-59 the substrate 10 and substrate surface 16 is oriented relative to a fixed stylus 20. This embodiment is applicable for testing small, even micro-scale, laboratory samples. In this embodiment, the stylus 20 is fixed rigidly and a substrate 10 is mounted onto a substrate alignment stage 650. As the topographic probe 43 performs a survey of the substrate surface 16, translation actuators 67, rotation actuators 318, or both articulate the substrate 10 as the stylus 20 travels along the substrate surface 16, in order to maintain stylus engagement with the substrate surface 16 at the desired depth, orientation, and relative displacement. This adjustment can be provided by an electronic gimbal with rotational actuators 318, as shown in FIG. 58, or by three translation actuators 67 with multi-axial attachments 50, as shown in FIG. 59. In the latter embodiment, one translation actuator 67 may be replaced with a fixed multi-axial attachment 50, which would allow for only two translation actuators 67 to be used. Both are capable of controlling the orientation of the substrate 10 such that the point of contact between the stylus 20 and substrate surface 16 is always perpendicular to the principal axis of stylus. By mounting these embodiments of the scanning alignment mechanism onto a 2-axis engagement mechanism (such as the embodiments described in Core Engagement Mechanism and illustrated in FIGS. 43, 45, and 46, such that the core 32 is replaced with the sample alignment mechanism), the stylus can remain fixed while performing a frictional sliding test, and requires no form of contact referencing. This is particularly useful, for example, when laboratory testing small samples with irregular surface geometry, or non-planar samples for which mechanical properties are desired without reshaping of the original substrate surface.

Core

Figure 37:
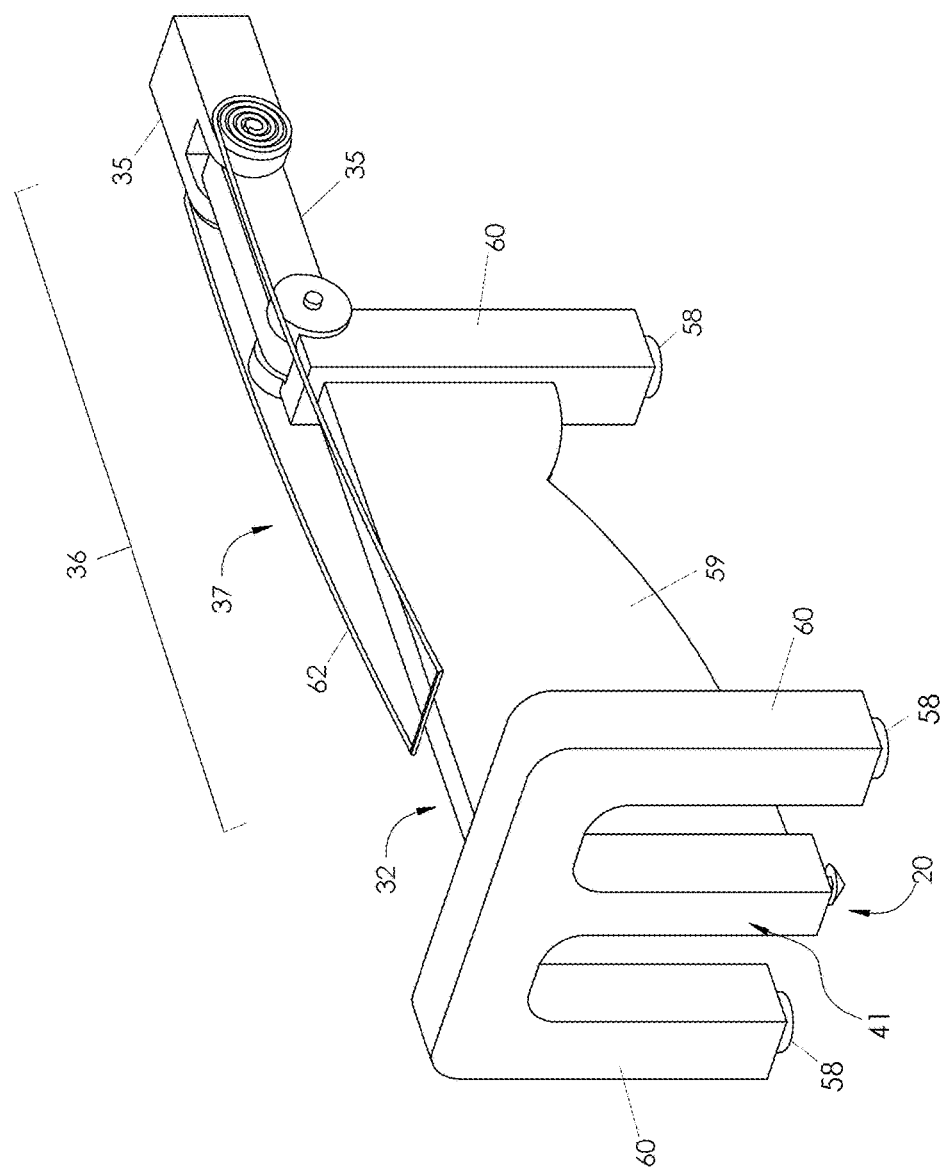
FIG. 37 is a schematic perspective view of an exemplary normal force actuator for the testing apparatus of FIGS. 1 and 19 according to embodiments of the present invention.
Figure 38:
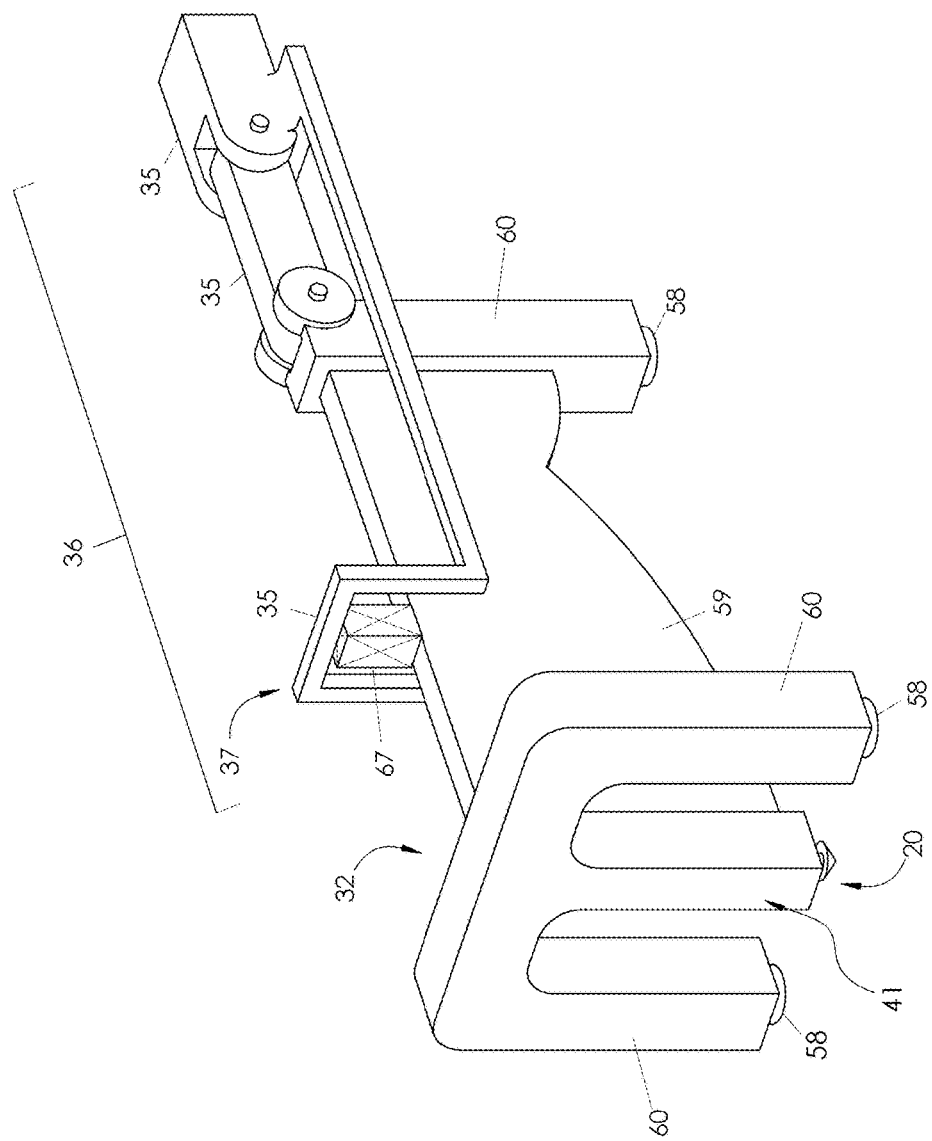
FIG. 38 is a schematic perspective view of an exemplary normal force actuator for the testing apparatus of FIGS. 1 and 19 according to embodiments of the present invention.
Figure 39:
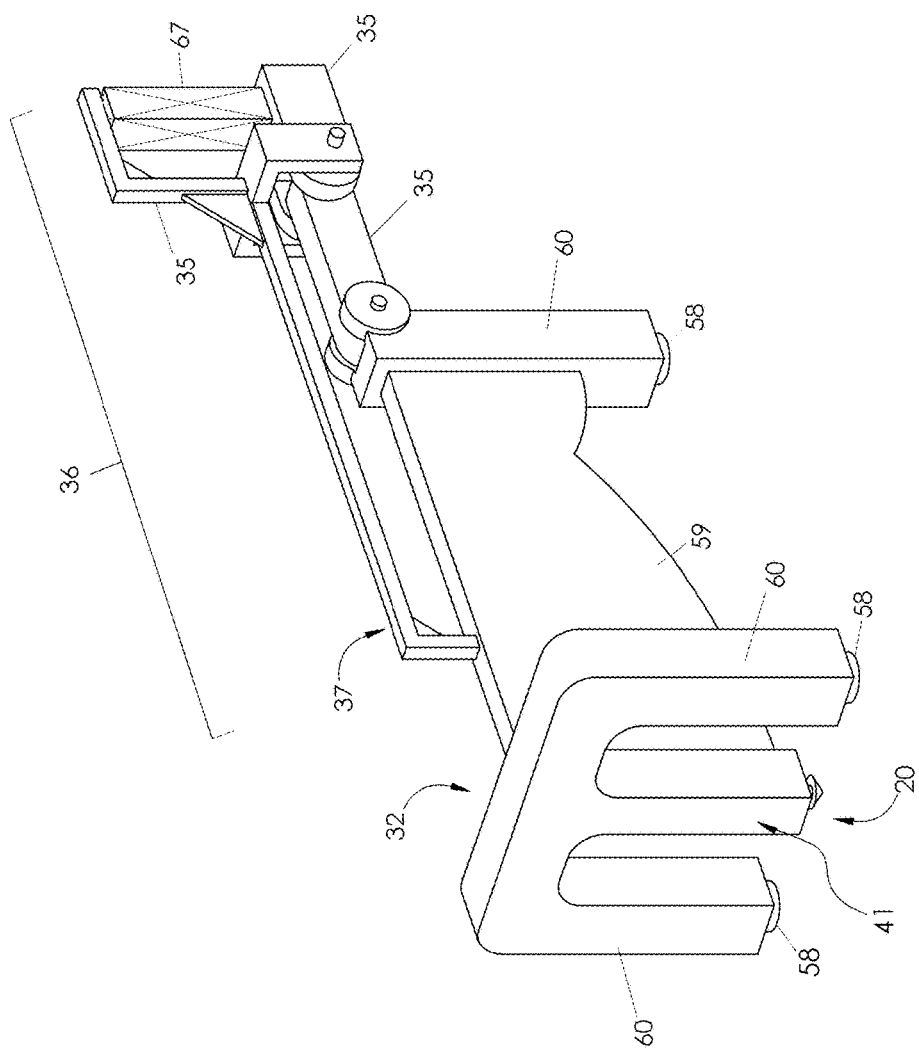
FIG. 39 is a schematic perspective view of an exemplary normal force actuator for the testing apparatus of FIGS. 1 and 19 according to embodiments of the present invention.
Figure 40:
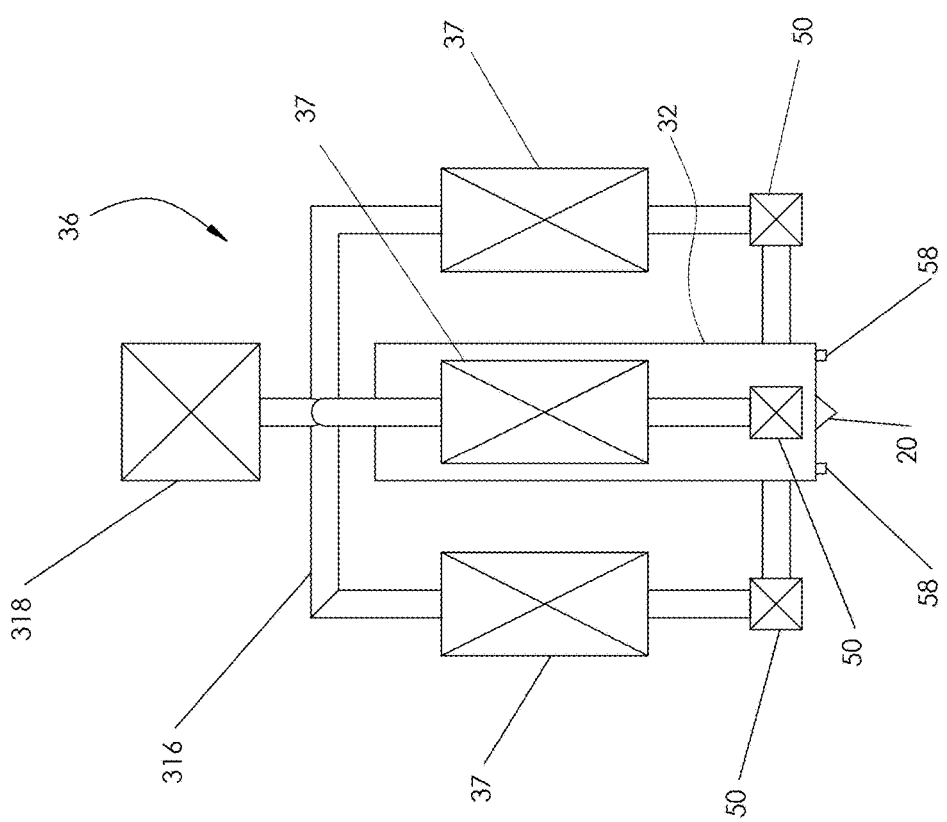
FIG. 40 is a schematic side view of an exemplary normal force actuator for the testing apparatus of FIGS. 1 and 19 according to embodiments of the present invention.

In some embodiments, the stylus 20 is supported by or continuous with the core 32, which is a load bearing assembly accommodating reaction forces from the substrate 10 as well as applied loads from the stylus engagement mechanism 41 and core engagement mechanism 36. Referring to FIGS. 37-40, the core 32 may be configured to provide lateral support to isolate the lateral frictional load from the engagement load reaction force on the stylus 20. In one exemplary embodiment, as shown in FIGS. 37 and 38, the core 32 may include a rib 59 extending parallel to the trajectory of the stylus 20 and the direction of the deformation. The rib 59 may be a plate, gusset or other reinforcement. In another embodiment, as shown in FIG. 40, the core 32 may be configured to have an enhanced stiffness per weight—such as by altering the cross-section shape of the core 32. In another embodiment, as shown in FIG. 40, the core 32 may include a brace 61, extending between the stylus 20 and the core 32.

Figure 27A:
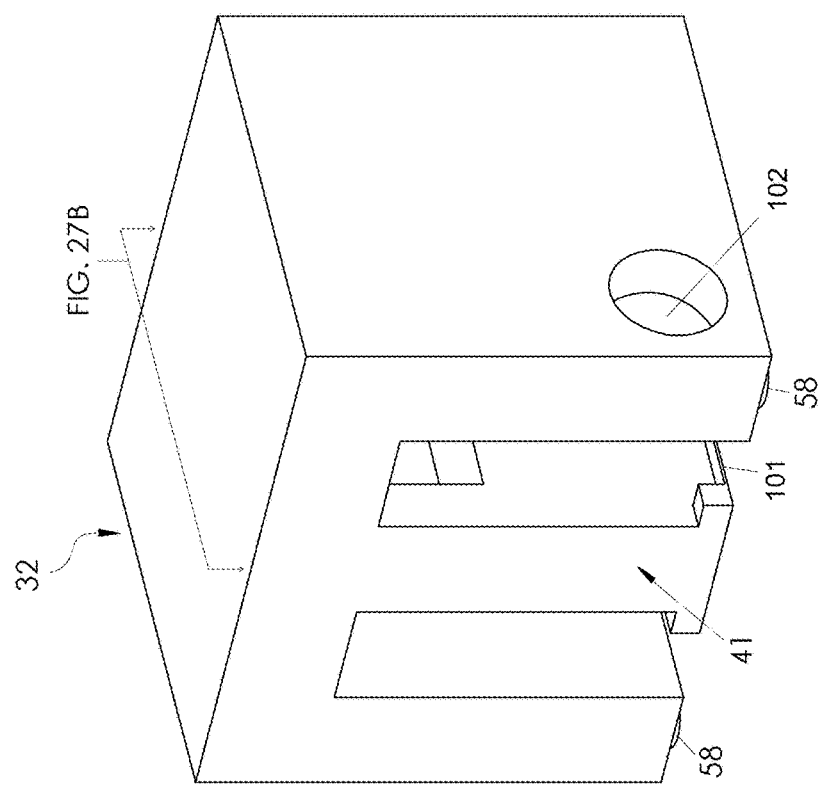
Figure 27B:
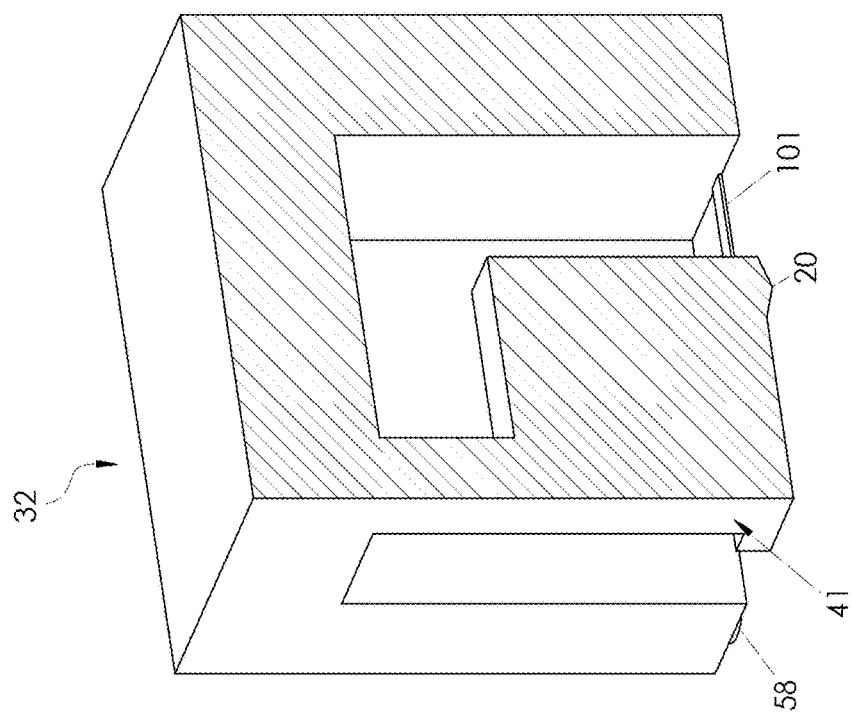
Figure 27C:
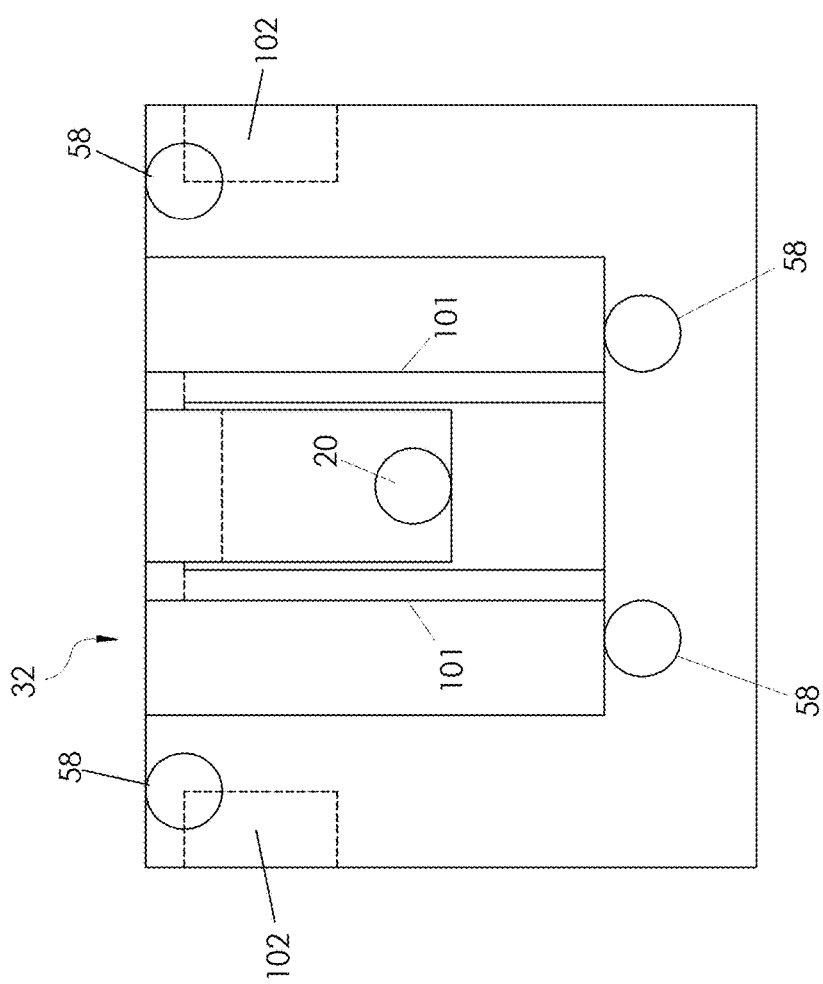

FIGS. 27A-B and 55A-C show an example of a core 32 which is part of a testing apparatus 30 and substrate monitoring device 39. The testing apparatus 30 may include floats 58 on the core 32 that supports the stylus 20. A contact referencing alignment mechanism is shown in FIG. 27C with four floats 58. The number of floats may be adjusted based on the application. Two of the floats 58 may be located closer to each other to avoid an intermittent three-point contact between the core 32 and the substrate surface 16. The two floats 58 located closer together are shown at the front of the device, but may be located at the back of the device. The configuration shown in FIG. 27C provides more room for the substrate monitoring device 39. The testing apparatus 30 may include one or more tension ties 101 to limit the tangential contact force between the stylus and the substrate. FIGS. 27D-27F provides an exemplar embodiment of tension ties 101 for a testing apparatus 30. Floats 58 are not shown, but may be used. The tension ties 101 may comprise one or more slender cross-sections which are sufficiently strong to resist axial and shear loads but compliant enough to be flexible in bending. The testing apparatus 30 may be machined from a block, manufactured by etching methods, or constructed using 3D printing techniques, including laser sintering. A 3D printing method may be employed to form the testing apparatus 30 from steel, nickel alloys, or titanium. Other materials and fabrication techniques are also possible. The testing apparatus 30 may be formed from a unitary block of material. In one embodiment, the testing apparatus 30 may include a stylus engagement mechanism 41, residual substrate measurement device 39 and core 32, as described above, which may be integrated in one body, such as a unitary block of material. According to one embodiment, the testing apparatus 30 may include a core 32 formed from a unitary block of material. The unitary block of material may be formed by any suitable process, e.g., machining a block of material or building up the block of material through 3D printing. Portions of the testing apparatus 30 may have a surface coating or treatment providing increased wear resistance. The testing apparatus 30 may also include load transfer points 102 to maximize stability with the core engagement mechanism. The load transfer points 102 may be set between the stylus 20 and the rear floats 58 to help distribute the load between the floats 58. The testing apparatus 30 may also include substrate monitoring device mounts 103 located on the side, bottom, and/or the top of the testing apparatus 30.

In the testing apparatus 30, the substrate monitoring device 39 may be mounted after the stylus 20 is installed. As shown in FIG. 27B, the rear end of the testing apparatus 30 may be extended to host the substrate monitoring device 39, protecting it from potential damage and providing locations for monitoring and measuring the substrate contact response 12. Additionally, the substrate monitoring device 39 of other forms described above may be included within the testing apparatus 30, either being attached to the core 32, or utilized in a stand-alone system.

Figure 36A:
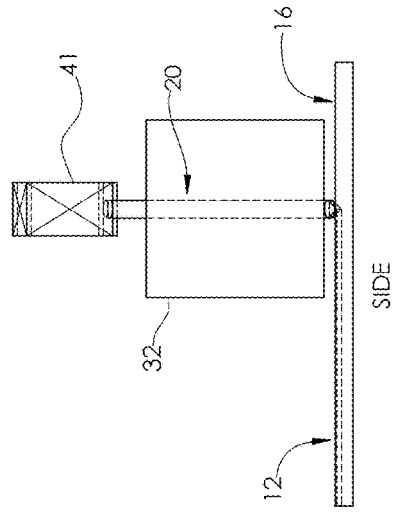
FIGS. 36A-C are schematic perspective view, front view, and side view, respectively, of another exemplary testing apparatus core capable of hosting two styluses according to embodiments of the present invention.
Figure 36C:
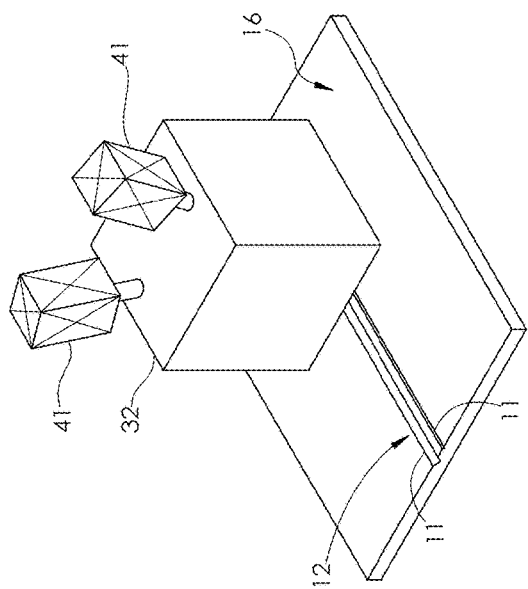
Figure 36B:
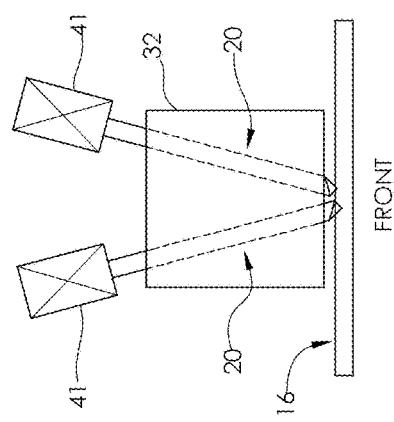

The testing apparatus 30 including multiple styluses 20 may also be utilized to perform multiple concurrent deformations 11 with varying engagement loads and varying stylus 20 geometries. A multi-deformation apparatus could be configured in a number of ways. Some embodiments can be seen in FIGS. 35A-36C. In another embodiment, three floats 58 are used as a contact referencing alignment mechanism to maintain the local angular orientation of the styluses relative to the substrate surface 16. Within the area of these three or more floats 58, is one or more styluses 20, each of which are free to move along their principal axis in the core 32 with a stylus engagement mechanism. The styluses 20 could each have the same geometry, or dissimilar geometries. Once the multiple deformations 11 are made, the mechanical properties can be calculated from measurement of the individual substrate contact responses 12, but also from the comparison of the substrate contact response behavior relative to differences in stylus 20 geometry, engagement loads, sliding loads, or other variable factors. Multiple deformations 11 could be run concurrently or by multiple sequential contact mechanics tests using the same stylus 20. In FIGS. 35A-C, the center points of the stylus 20 are not aligned in the Y direction, as they are in FIGS. 36A-C. The styluses are staggered in the Y direction and thus closer in X, bringing the deformations 11 closer together. By rotating the multi-stylus assembly, deformations 11 could be brought as close together as desired. In FIGS. 36A-C, the closest the styluses 20 can be placed is the diameter of the bushings or bearings, or the styluses 20 themselves if no external bushing is added. The distance between the styluses 20 is equal to the distance between deformations 11. In some instances, a minimum distance between deformations 11 must be observed to not have strain effects from the leading edge affect the trailing edge. However, strain effects could be measured on purpose by having the trailing edge within the strain hardened area produced by the leading edge.

One instance of when using multiple styluses presents an advantage over a single stylus is when performing a frictional sliding test across a welded region. For example, if testing the seam weld of a steel pipe, utilizing three conical styluses with different included angles may provide more accurate results. This is due to generating slightly different high-strain regions in the substrate, which is ideal for this particular test scenario. Another example is using a combination of conical and spherical styluses for more accurate results when testing blindly or a large range of material characteristics. This is due to each stylus generating significantly different amounts of strain in the substrate, which acts as complementary information. The benefit of multiple styluses of similar or different geometries applies to many other testing situations, and the best combination may be determined and selected by analytical or physical research, and catered to produce the most accurate test results.

In another embodiment, the apparatus consists of more than one cores, which host one or more styluses. A multi-core apparatus could be configured in a number of ways. For example, two or more cores may travel in parallel or they can travel in directions perpendicular to one another. The apparatus may use multiple core engagement mechanisms to connect to a single frame.

Stylus Engagement Mechanism

In one embodiment, the testing apparatus is configured to form a deformation in a substrate 10 using an stylus engagement mechanism 41 operating in either load or displacement control. If the stylus engagement mechanism 41 is operated in displacement control mode than the testing apparatus is configured to perform a displacement control test. FIG. 22 shows an embodiment where the stylus 20 is fixed to the core 32, the penetration depth of the stylus 20 is controlled and the stylus load with the substrate 10 is measured. In one embodiment, this is controlled by adjusting the elevation 46 of the alignment mechanism 40, as discussed above. The stylus engagement mechanism 41 may constantly measure a component of the reaction force (e.g., normal or frictional reaction force) on the stylus 20. The stylus engagement mechanism 41 may measure the stylus load by a variety of direct or indirect methods. In one embodiment, the stylus load reaction force is detected by monitoring the deformation of the stylus 20, such as with a strain gauge detecting the strain on the surface of the core 32 or other component of the alignment mechanism, or by monitoring the change in height of all or a portion of the core 32; e.g., with linear voltage displacement transducers (LVDT) or optical sensors (such as a laser sensor, an inductance sensor, etc.). In another embodiment, the engagement load reaction force is detected with an in-line force transducer hosted within the core 32.

The contact mechanics test may also be conducted in load control. In one embodiment, the stylus 20 may be movable relative to the core 32 through the use of a stylus engagement mechanism. Embodiments of the stylus engagement mechanism include a threaded connection, spring, piezoelectric element, dead weight, lever arms, piston or other means. For example, the stylus 20 may be coupled to a movable piston actuated by any appropriate method, including electromechanically, mechanically, hydraulically, pneumatically, etc. The apparatus described deforms the substrate with a fixed load, but is free to move vertically within the core 32. As the apparatus is driven across the substrate surface 16, the substrate contact response depth will vary according to the local mechanical properties of the substrate. Load controlled tests eliminate the need for monitoring the normal load of the stylus 20 during contact mechanics testing. This confers distinct advantages in contact mechanics testing over irregular surfaces, and in measuring changing properties in a single material, such as across a weld, encompassing base metal, the heat-affected zone, and the weld itself. The load controlled embodiment allows for multiple concurrent deformations to occur with varying engagement loads and varying stylus 20 geometries, which is discussed later as a specific embodiment of the core 32. Furthermore, load control allows the stylus to travel over asperities that may exist on the substrate surface.

Figure 60A:
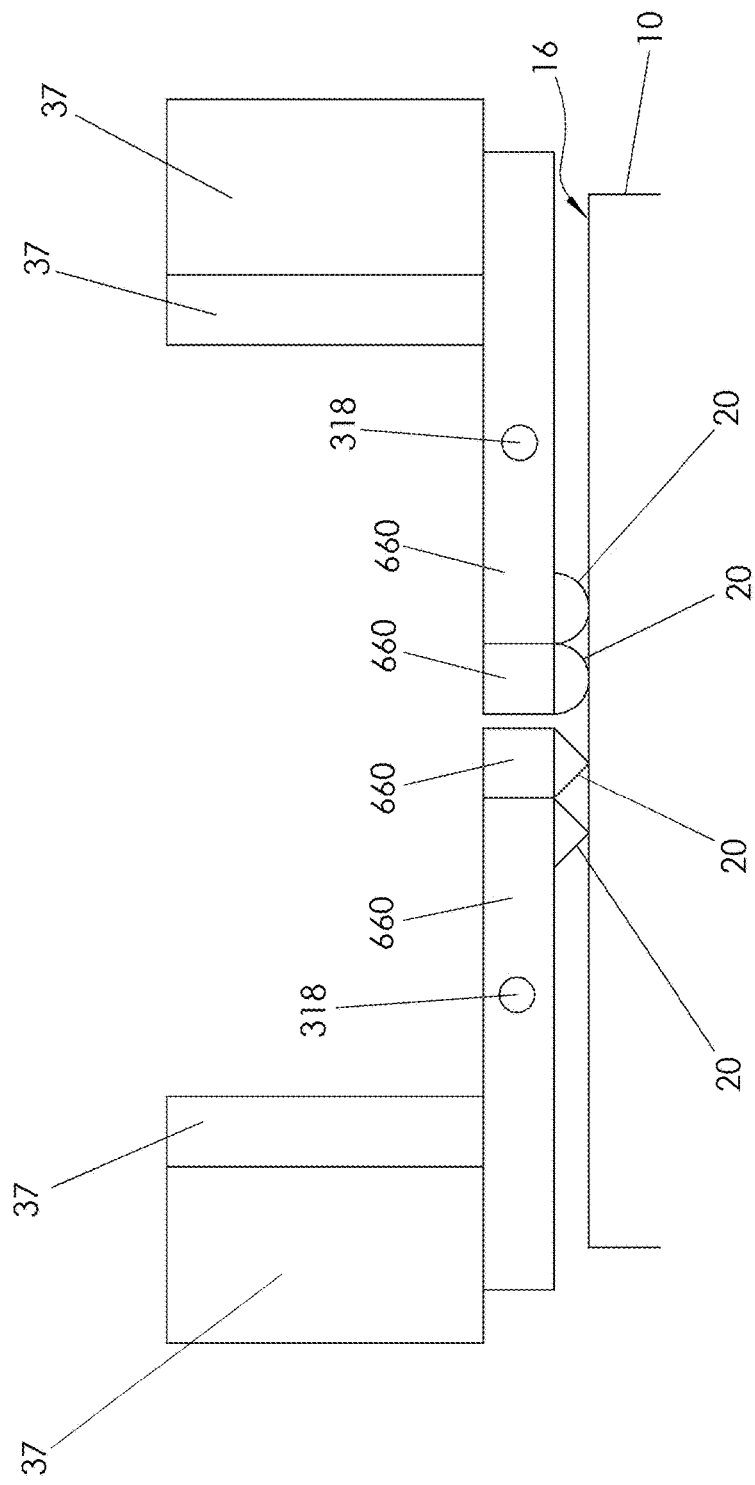
FIG. 60A depicts a schematic side view and FIG. 60B depicts a schematic perspective view of an exemplary stylus engagement mechanism for the contact mechanics testing apparatus of FIGS. 1 and 19 according to embodiments of the present invention.
Figure 60B:
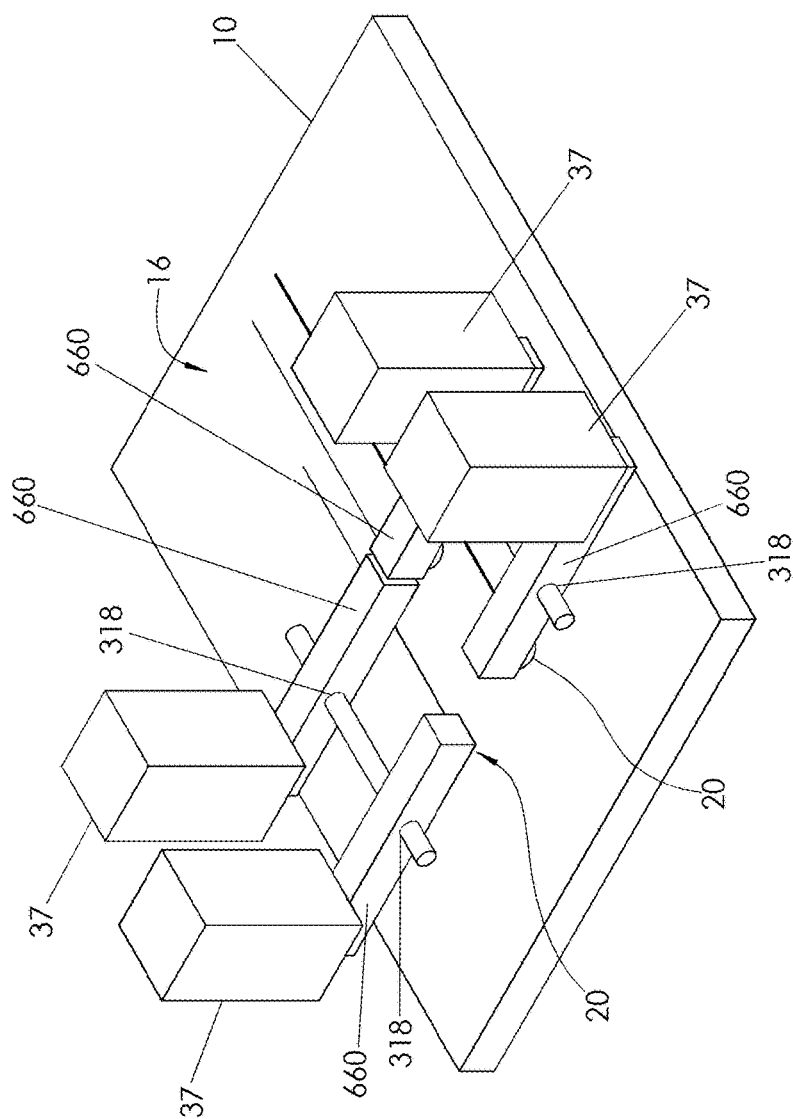

In one embodiment, in which a normal force actuator 37 provides a load to the stylus 20 via a lever arm 660, the stylus 20 and lever arm 660 may be rigidly connected, as shown in FIGS. 60A-B. In the embodiment shown, there are multiple styluses 20, although there may only be one. The lever arm 660 is situated perpendicular to the direction of movement such that a rotational attachment 318 carries the loads seen by the stylus 20 without significant frictional forces from the stylus 20 contacting the substrate surface 16. The advantage to this type of implementation is the reduction of friction errors caused by using a lever arm to apply an engagement load to a stylus via a linear bearing, as well as significantly reducing the overall height of the core, stylus, and stylus engagement mechanism necessary. In addition, the lever arms allow the stylus engagement load to be applied remotely, and the distance between styluses, and subsequent residual substrate surfaces, to be reduced.

Normal Force Actuator for Contact Referencing

For apparatuses operating using a contact referencing stylus alignment mechanism, external loads must be applied to the core 32 to ensure engagement of the stylus 20 and/or floats 58 with the substrate 10. Referring now to FIGS. 37-41, the normal force actuator 37 applies an engagement force to the core 32 and the stylus engagement mechanism 41 applies an engagement load to the stylus 20. For a control embodiment, the engagement load is applied to the core 32 such that the load at the stylus 20 is greater than the reaction force between the stylus 20 and substrate surface 16. The magnitude of the engagement load reaction forces is dependent on the substrate 10, the geometry of the stylus 20, and the residual substrate contact response depth 26. As shown in FIG. 37, in one embodiment, the normal force actuator 37 includes a torsional spring 62. The torsional spring 62 is anchored to a structure fixed to the substrate 10, such as the core engagement mechanism 36, and engages an arm applying an engagement load to a portion of the core 32. In another embodiment, the normal force actuator 37 may include another mechanism, such as a linear actuator. As shown in FIG. 38, the normal force actuator 37 may include a translation actuator 67 coupled to a transfer module 35 that is anchored to the core engagement mechanism 36 and applying an engagement force to a portion of the core 32. As shown in FIG. 39, the normal force actuator 37 in another embodiment may include a translation actuator 67 mounted to a transfer module 35 anchored to the core 32 and applying an engagement load to the core 32 through a transfer arm.

FIG. 40 illustrates a schematic side view of an embodiment of a core load applicator which uses one or more normal force actuators 37, in this case four (one not shown), to apply a normal force to the core 32 via one or more multiaxial attachments 50. The normal force actuators 37 may be coupled to a yoke 316, which provides additional translational displacement and/or force application from the drive mechanism. The core 32 is shown connecting the stylus 20 and floats 58 to the multiaxial attachments 50, though the stylus 20 and floats 58 may also be coupled independently of the core 32. In this embodiment, the yoke 316 is shown mounted to a rotational displacement actuator 318, which allows for controlled rotation of the core 32 independently of the displacements and forces being applied by the drive mechanism. These displacements and forces would be applied through the rotational displacement actuator 318 and yoke 316 to the core 32.

Core Engagement Mechanism

According to an exemplary embodiment, the testing apparatus 30 is configured such that one or more core engagement mechanisms 36 may transmit translational motion to the core 32 and the stylus 20 while the core 32 and the stylus 20 may move independently of the core engagement mechanism 36 at a local angular orientation to the substrate surface 16. The core engagement mechanism may be operated at multiple translational velocities, which will impose different strain rates into the substrate for a frictional sliding test. The core 32 may be coupled to the core engagement mechanism 36 with a transfer module 35. In one embodiment, the transfer module 35 is configured to transfer translations to the core 32 from the core engagement mechanism 36 with pinned connections 63.

Referring to FIGS. 41A-42B, the core engagement mechanism 36 for providing translational motion along the substrate surface 16 is shown according to several exemplary embodiments. The core engagement mechanism 36 provides translational motion through the transfer module 35 without interfering with the alignment of the stylus 20 as prescribed by the core 32. In other embodiments, the core engagement mechanism 36 may be coupled to the core 32 with another suitable connection. The translational motion may be applied with a lateral force in the pushing or pulling force; e.g., a force in a direction towards or away from the stylus 20. According to an exemplary embodiment, the lateral force is applied with a displacement actuator 66 operating in the direction parallel to the substrate surface 16 being tested. The displacement actuator 66 may be any suitable mechanism (e.g., mechanical, hydraulic, pneumatic, electro-magnetic, etc.) capable of providing a sufficient force to overcome the friction resulting from the engagement load applied by the stylus engagement mechanism 41.

Figure 41A:
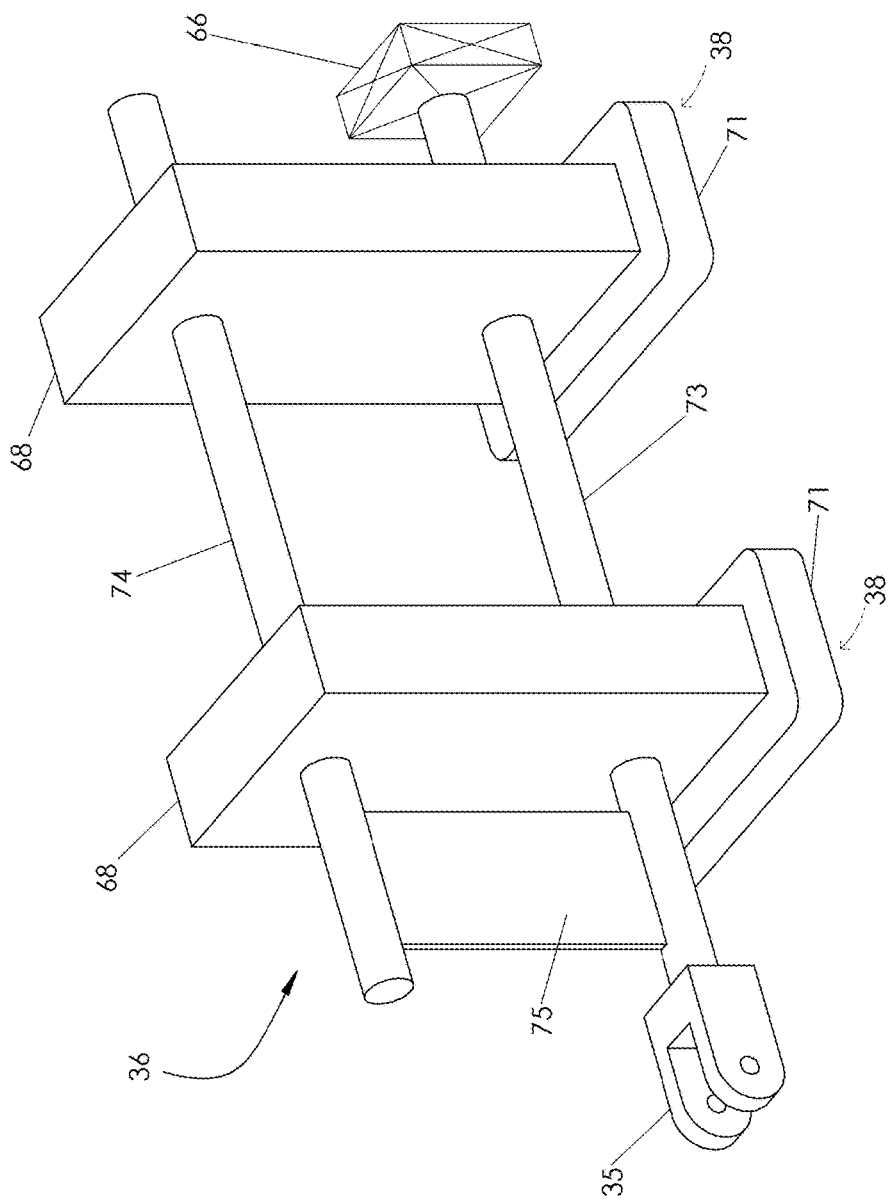
FIG. 41A is a schematic perspective view and FIG. 41B is a schematic side view of an exemplary portion of a frame engagement mechanism for the testing apparatus of FIGS. 1 and 19 according to embodiments of the present invention.
Figure 41B:
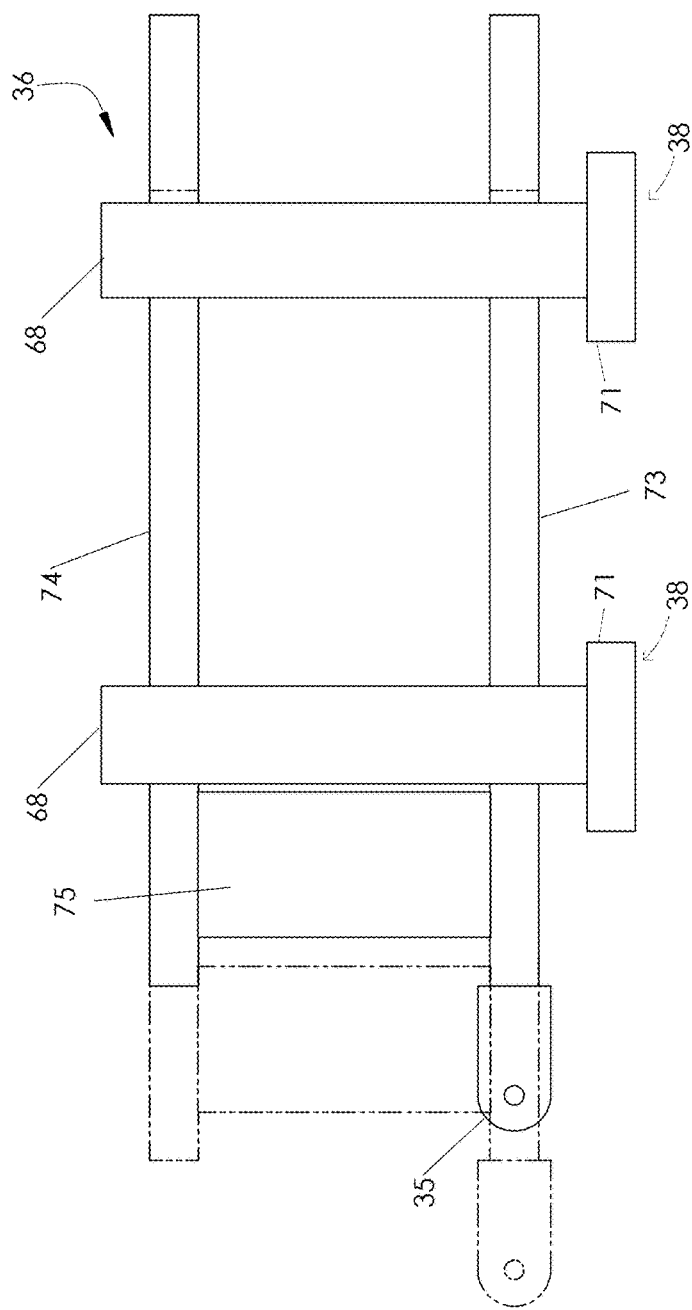

Referring to FIGS. 41A-B, the displacement actuator 66 acts upon a sliding guide 73. The sliding guide 73 is held in place using support structures 68 and mounts 38 (for example, magnets 71), which may also act to align the sliding guide 73 with the desired load application point, e.g., the transfer module 35. The load application point connecting the core engagement mechanism 36 to the core 32 is preferably positioned close to the substrate surface 16 to reduce the moment imparted on the stylus 20 when a sliding load is applied. This also prevents the effective reduction of the engagement load applied to the stylus 20 when a sliding load is applied. To provide stability in the core engagement mechanism, a plurality of mounting support structures 68 may be used at multiple locations along the sliding guide 73 path to guide an optional secondary sliding guide 74 connected to the sliding guide 73 by a connecting member 75. Each of the mounting support structures 68 may be coupled to the substrate 10 by the frame engagement mechanism mounts 38.

Figure 42A:
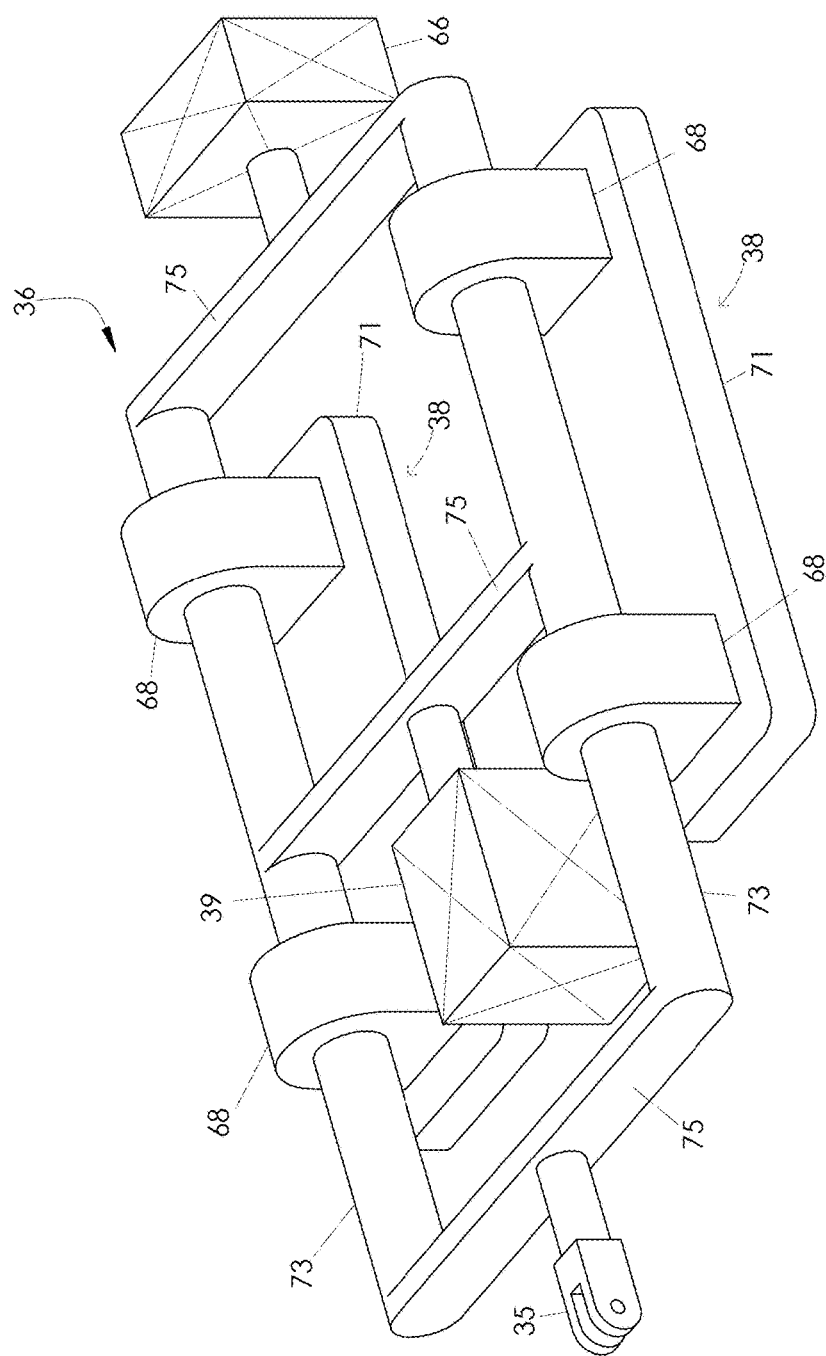
FIG. 42A is a schematic perspective view and FIG. 42B is a schematic side view of an exemplary portion of a frame engagement mechanism for the testing apparatus of FIGS. 1 and 19 according to embodiments of the present invention.
Figure 42B:
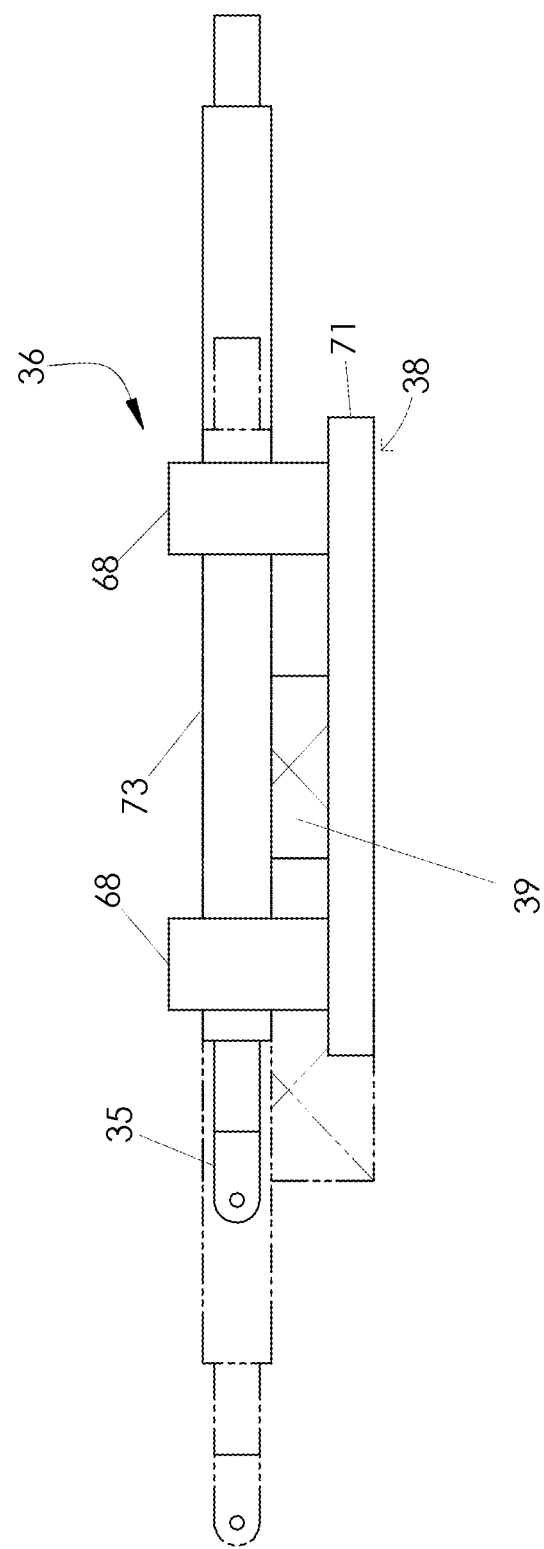

Referring to FIGS. 42A-B, in another embodiment, the core engagement mechanism 36 may include multiple sliding guides 73. The sliding guides 73 are held in place using multiple support structures 68 which also act to align each of the sliding guides 73. The multiple sliding guides 73 may be connected by connecting members 75 such that they act in unison upon the desired load application point. In such an embodiment, the substrate monitoring device 39 may be included in the core engagement mechanism.

Figure 43:
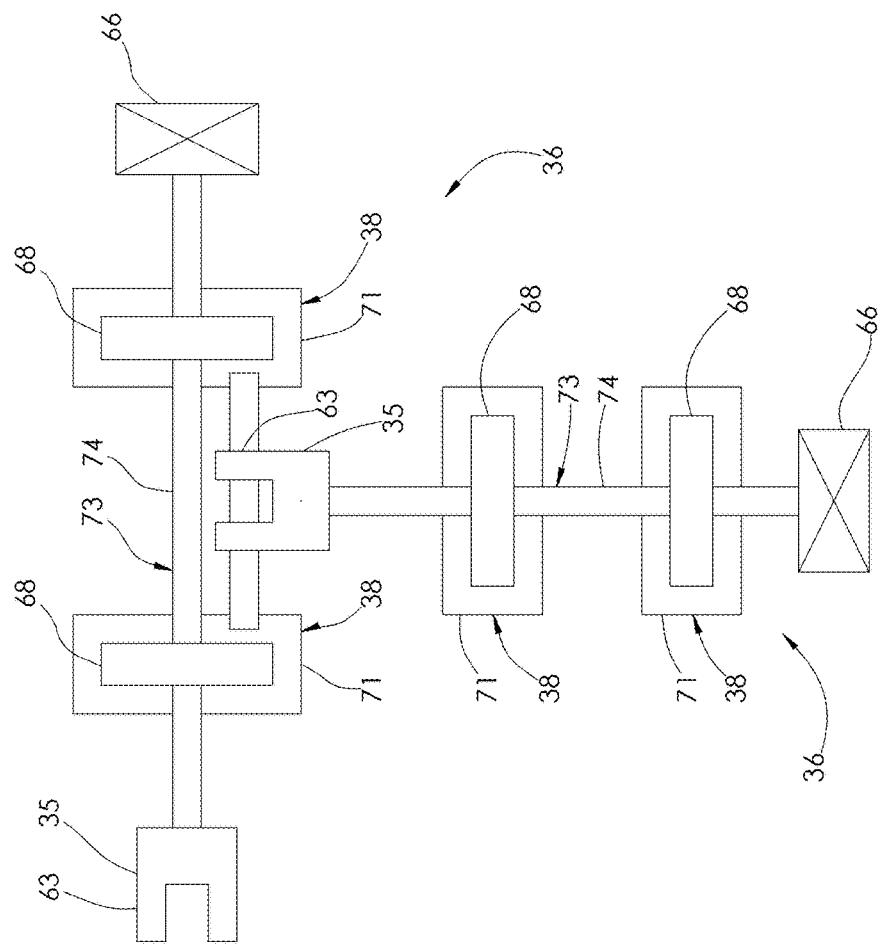
FIG. 43 is a schematic top view of an exemplary portion of frame engagement mechanisms coupled to create multi-axial movement according to embodiments of the present invention.
Figure 44:
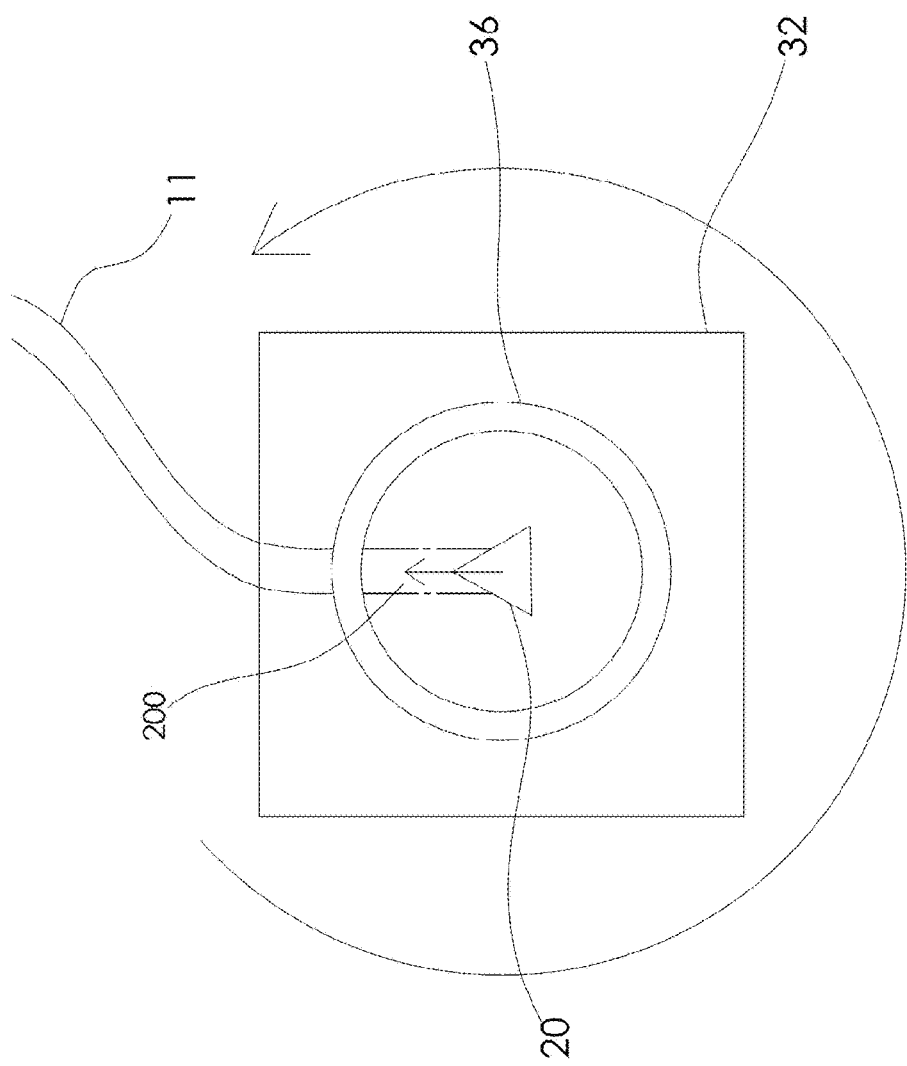
FIG. 44 is a schematic top view of an exemplary core for stylus rotation according to embodiments of the present invention.

Referring to FIG. 43, in another embodiment, the testing apparatus 30 may include multiple core engagement mechanisms 36, each with a different orientation, to move the core 32 (and stylus 20) through independent line trajectories, including a two-dimensional, non-linear trajectory. Each core engagement mechanism 36 may be coupled to one or more pinned connections 63. Referring to FIG. 44, the core 32 may rotate through the use of bearings and a rotational core engagement mechanism 36 to maintain the local angular orientation of the core 32 (and stylus 20) with respect to the instantaneous direction of movement 200 of the core 32 (and stylus 20), and as such also the direction of the deformation 11.

Figure 45:
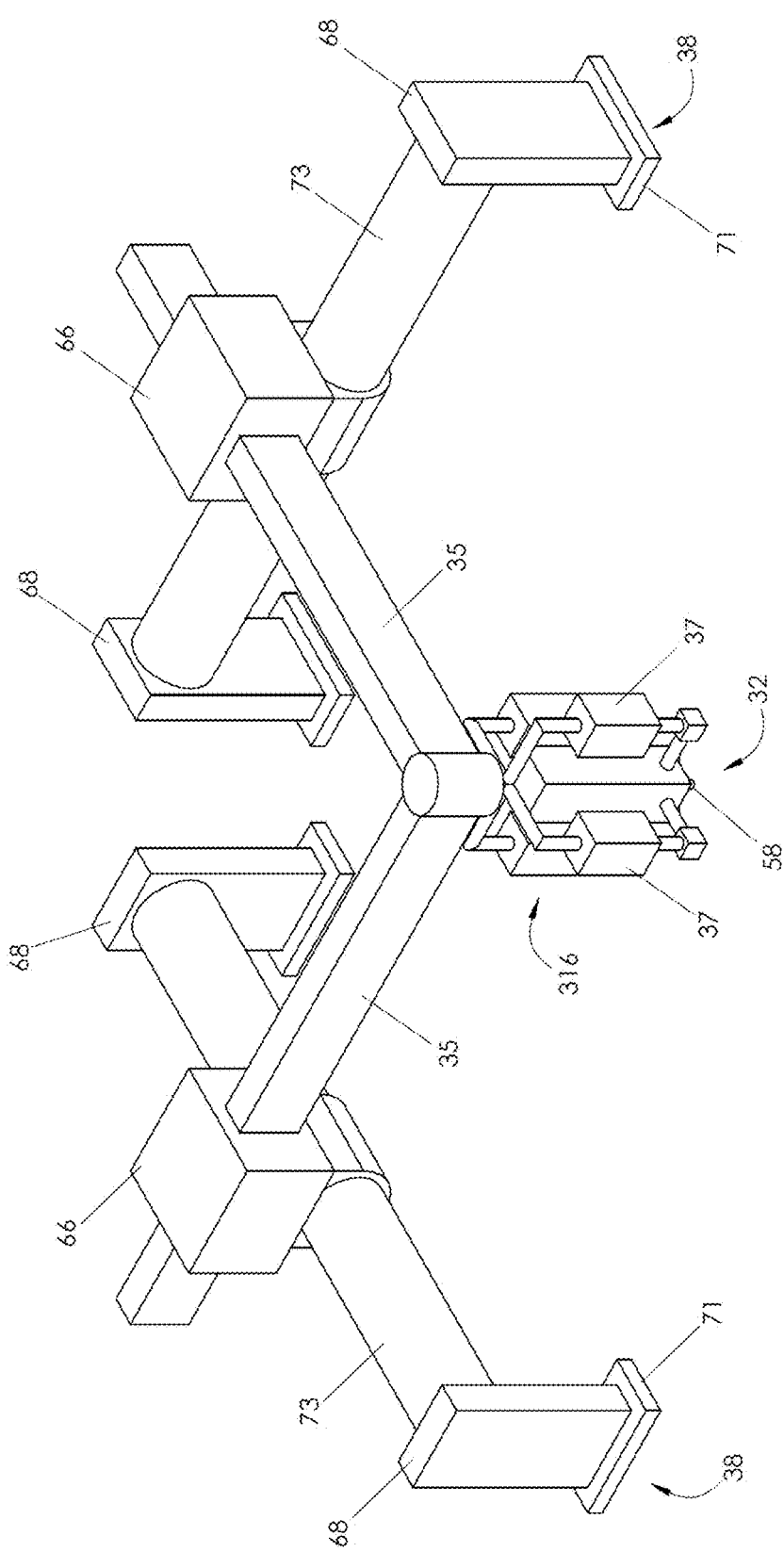
FIG. 45 is a schematic perspective view of exemplary frame and core engagement mechanisms for the testing apparatus of FIGS. 1 and 19 according to embodiments of the present invention.

FIG. 45 shows a schematic isometric view of an embodiment of the apparatus drive mechanism capable of performing a multi-directional frictional sliding test. Two displacement actuators 66 apply a translational displacement to the core 32 via a yoke 316. A rotation actuator (not shown) may also apply a rotational displacement to the core 32 via the yoke 316. A normal force is applied to the core 32 and floats 58 by four normal force actuators 37 (one not shown). The displacement actuators 66 are coupled to sliding guides 73, which may include translational attachments, and may be coupled to mounts 38, and supports 68. In this embodiment, each support 68 is fixed to the substrate surface 12 using magnets 71. The core 32 and yoke 316 shown in this embodiment are presented in greater detail in FIG. 40.

Figure 46:
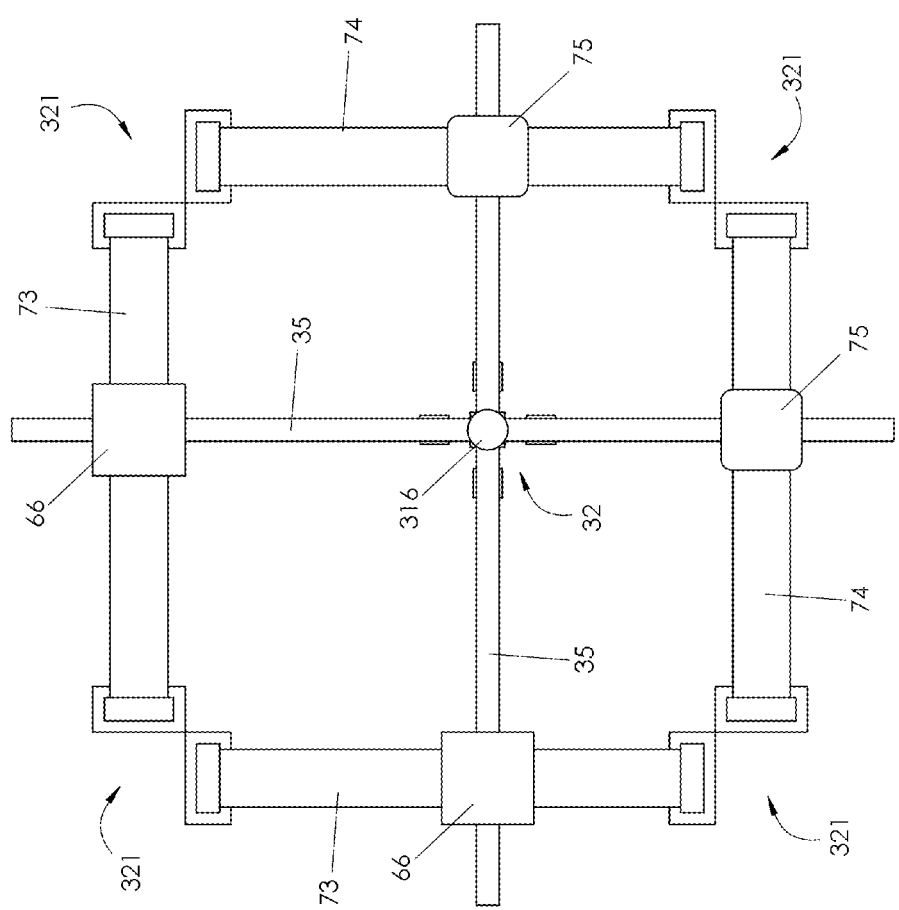
FIG. 46 is a schematic top view of exemplary frame and core engagement mechanisms for the testing apparatus of FIGS. 1 and 19 according to embodiments of the present invention.

FIG. 46 shows a schematic top view of the embodiment described in FIG. 45, except configured to operate with the use of secondary sliding guides 74, which are coupled to the transfer module 35 by a connecting member 75. The secondary sliding guides 74 provide additional stiffness to the transfer modules 35.

Figure 47:
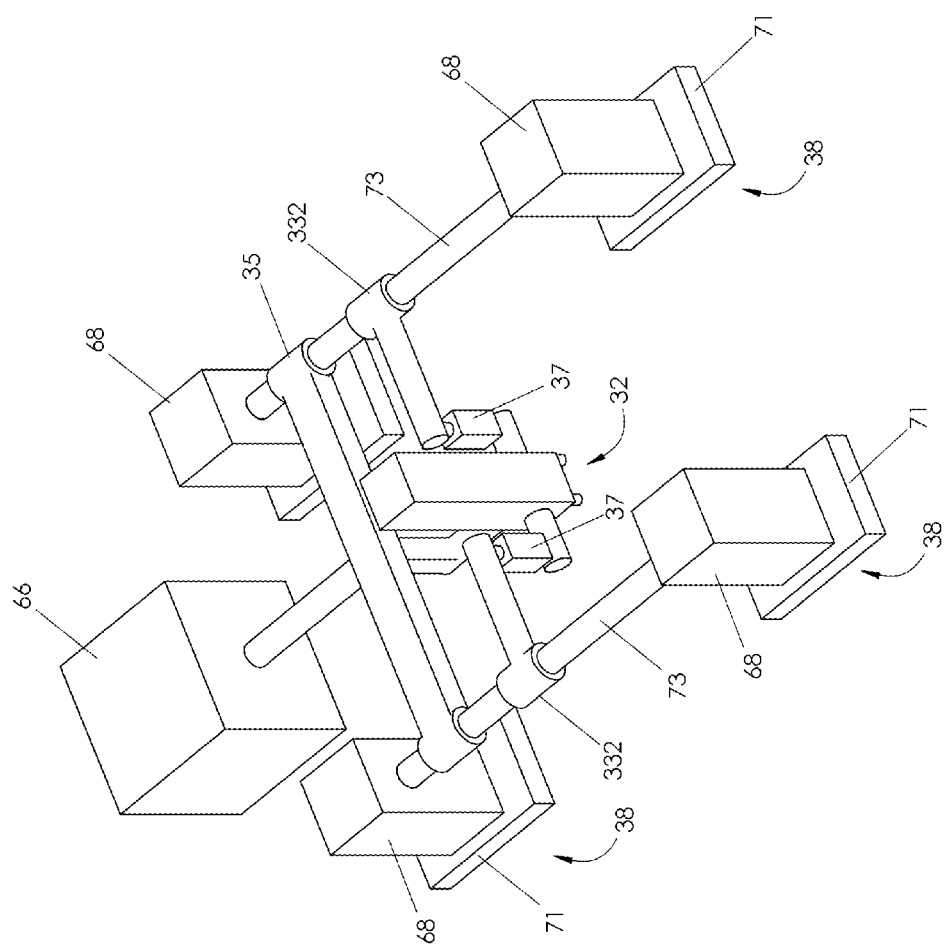
FIG. 47 is a schematic perspective view of exemplary frame and core engagement mechanisms for the testing apparatus of FIGS. 1 and 19 according to embodiments of the present invention.

FIG. 47 shows a schematic isometric view of another embodiment of the apparatus core engagement mechanism configured to increase the overall stiffness. In this embodiment, a displacement actuator 66 applies a translational displacement to the core 32 via a transfer module 35. A normal force is applied to the core 32 and floats 58 via two normal force actuators 37. The normal force actuators 37 are mounted to normal load actuator mounts 332, which are coupled to the transfer modules 35, which may include translational attachments, mounts 38, and supports 68. In this embodiment, the supports 68 are fixed to the substrate surface using magnets 71 as mounts 38.

In another embodiment (not shown in figures), the testing apparatus may include a position measuring device that measures, with respect to the substrate surface or the alignment mechanism, the movement and position of the one or more reference points on the styluses. The position measuring device can be one or more of the following string potentiometer, encoder, LVDT, optical measurement device including confocal, photonic triangulation or spectral laser system. In certain modes, the displacement can be measured using a charge-coupled device (CCD). Other embodiments use the same measurement methodologies as used for the substrate monitoring devices.

Frame and Frame Engagement Mechanism

The testing apparatus is structurally supported by the frame and the frame is coupled to the substrate through the frame engagement mechanism. The frame engagement mechanism is further comprised of mounts which provide direct contact with the substrate and supports which provide a fixed or adjustable connection between the mounts and the frame. In one exemplary embodiment the frame and frame engagement mechanism are fixed rigidly to the substrate and provide structural support for the test apparatus as it is driven by the displacement actuators along a path of fixed distance. In another exemplary embodiment the frame and/or frame engagement mechanism are configured to move with the testing apparatus allowing for an infinite range of motion such as continuous testing around the circumference of a pipe.

Figure 48A:
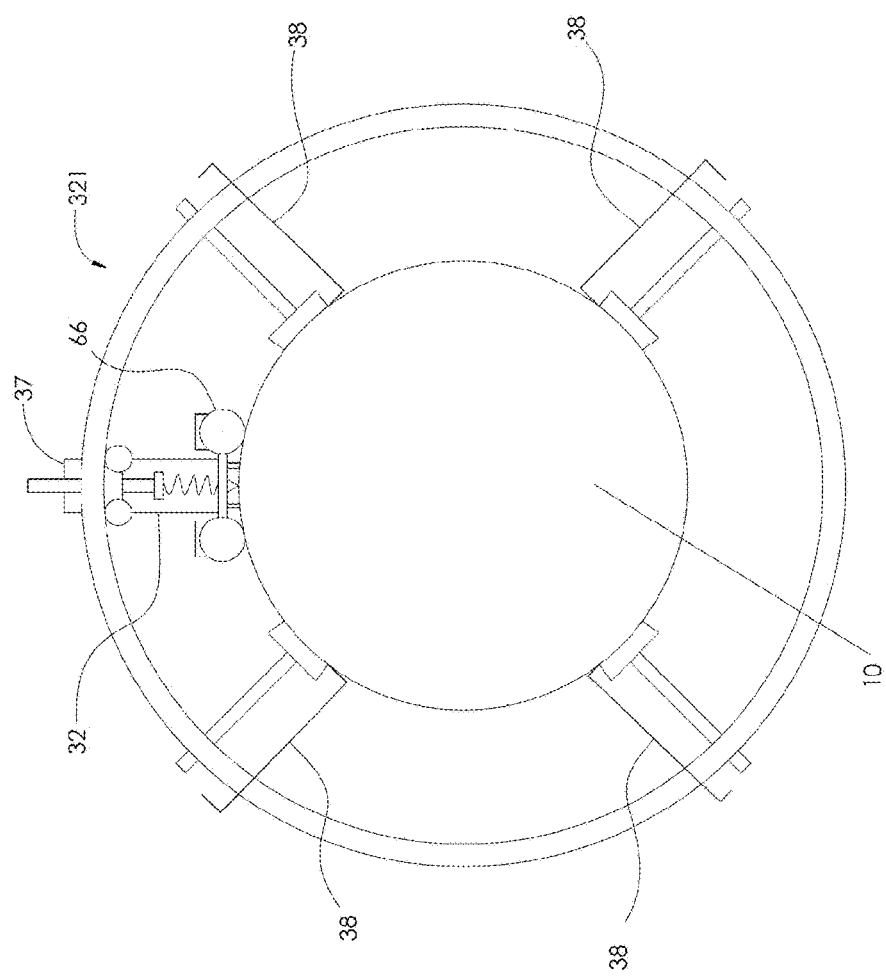
FIGS. 48A and 48B are schematic views of an exemplary frame and frame engagement mechanism for the testing apparatus of FIGS. 1 and 19 according to embodiments of the present invention.
Figure 48B:
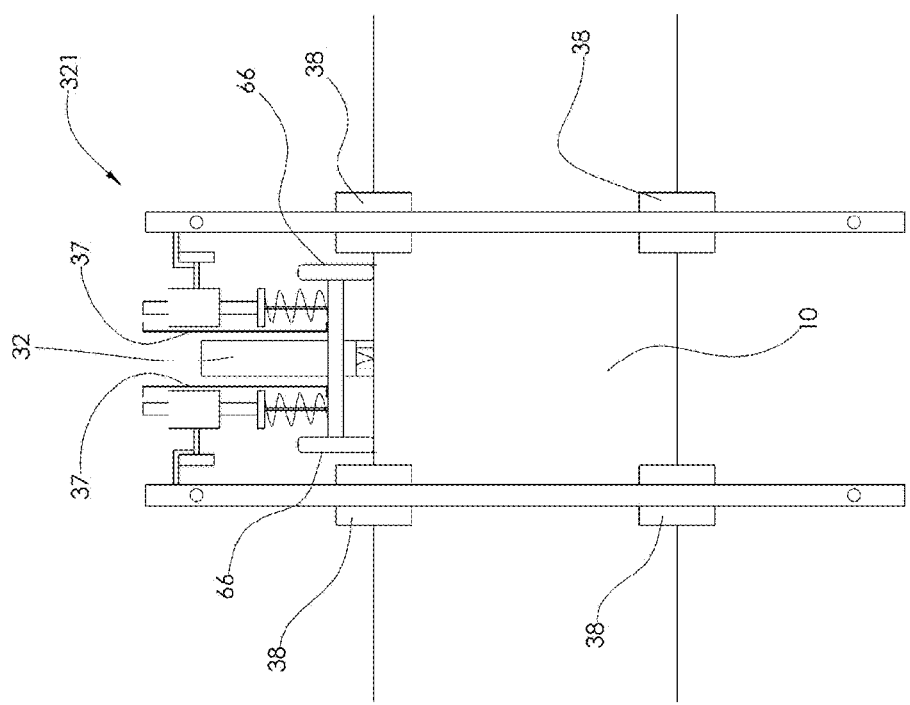

Referring to FIG. 48A-B, in another embodiment, the frame is configured as moveable object which follows a path around a circular substrate 10 set by the circular frame engagement mechanism 321. The frame engagement can conform to circular substrates of varying diameter via the height adjustable mounts 38. The frame 320 engages with the frame engagement mechanism 321 via the normal force applicator 37 and is driven around the circular path via displacement actuator 66.

Figure 49A:
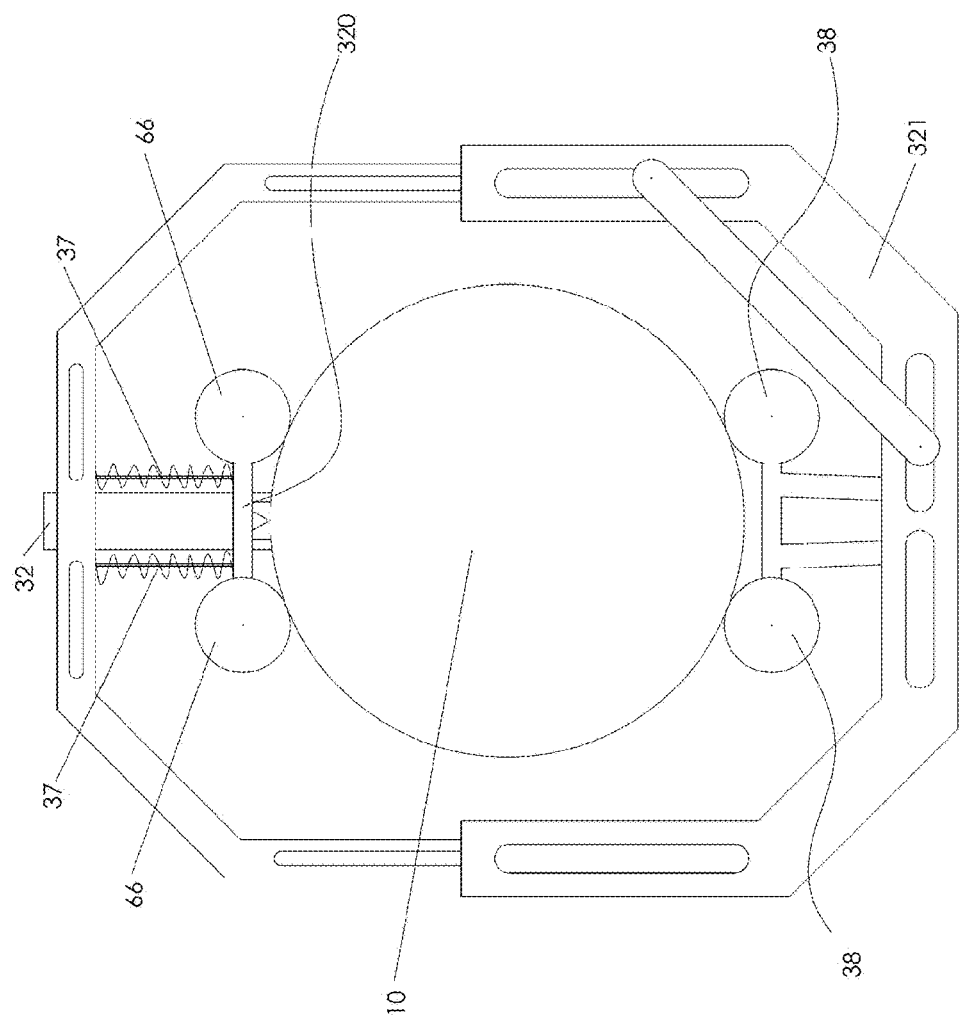
FIGS. 49A and 49B are schematic views of an exemplary frame and frame engagement mechanism for the testing apparatus of FIGS. 1 and 19 according to embodiments of the present invention.
Figure 49B:
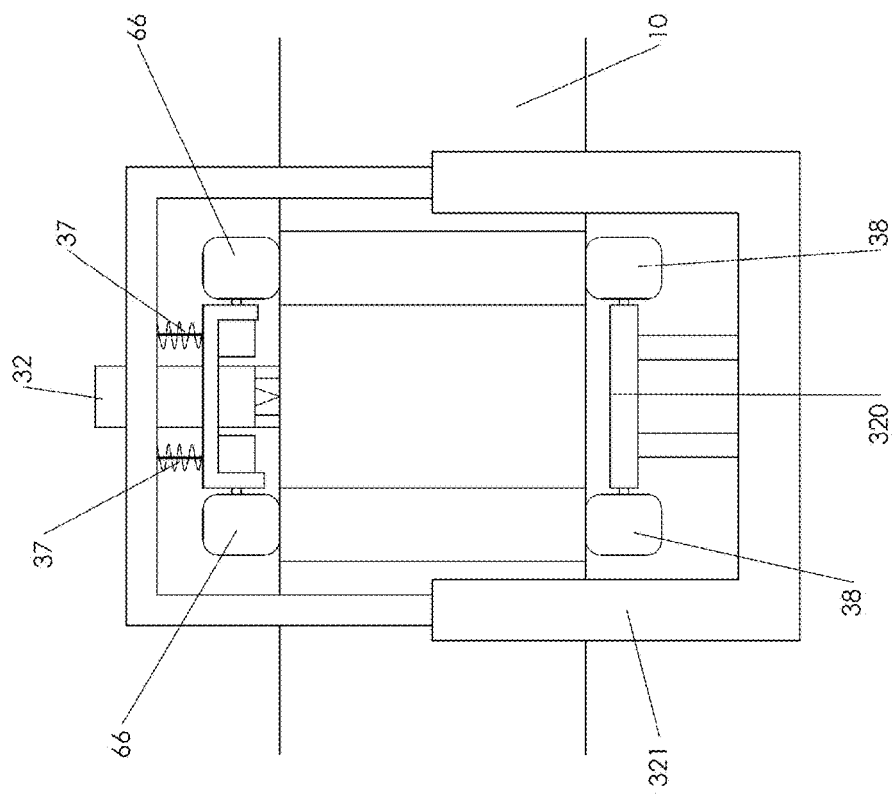

Referring to FIG. 49A-B, in another embodiment, the frame 320 is fixed rigidly to the frame engagement mechanism 321 while the frame engagement mechanism 321 is translated around the circular substrate 10 via displacement actuator 66 mounted to the frame 320 and the wheel mount 38 opposite the core 32. Normal force is applied to the core 32 through the normal force applicator 37. The frame engagement mechanism 321 contains adjustments which all the device to conform to substrates 10 of varying diameter.

Referring to FIG. 50, in another embodiment, the frame 320 translates around the circular substrate 10 and is engaged with the substrate 10 via the mounts 38 and the frame engagement mechanism 321, which is comprised of a cable 701 held in tension via a pulley 702 around the substrate 10. The cable 701 provides flexible structural support for the frame 320 which is engaged with the frame engagement mechanism 321 via the normal force actuator 37. The frame 320 is driven around the circular substrate 10 via pulley-style displacement actuator 66 to the frame. The frame engagement mechanism mounts to the substrate via mounts 38 which allow the frame to freely translate around the circular substrate 10.

Portable Attachment Mechanism

One embodiment of the support 38, shown in FIGS. 41A-42B, may be a portable attachment structure that is configured to couple the testing apparatus to the substrate. In a field environment, there may be many mounting configurations necessary to collect the required data. For testing seam welded pipes, the mounting structure must accommodate performing a frictional siding test in the circumferential direction of the pipe. For butt-welded pipe, the mounting structure would have to allow the device to contact mechanics test along the length of the pipe. In other instances, such as on structural beams or bridges, the testing apparatus would have to mount securely to flat surfaces. In one exemplary embodiment for a portable testing apparatus, the mounting structure may include magnetic devices such as electromagnets similar to those utilized in mag-drills to create the contact, as well as high pressure suction, with a ferro-magnetic substrate. In some exemplary embodiments, the testing apparatus may be utilized in a field environment, and the material sample may be prepared (e.g., with a surface preparation) prior to a contact mechanics test.

Substrate Monitoring Device

In one embodiment, the substrate monitoring device 39 shown in FIG. 1 is configured to collect ribbons or chips of material that are removed during a frictional sliding test performed in a machining mode. The substrate monitoring device 39 may consist of one or more components such that it is still capable of measuring characteristics of the substrate contact response 12. This device is placed on the trailing side of the stylus and collects material removed from the substrate surface using one or more methods such as magnetic traction, suction or adhesion. In one embodiment, the material collection device is a wheel that engages with the substrate surface and picks-up the material removed. In another embodiment, suction is used to gather the material and storage is based on adhesion or the use of compartments.

In one embodiment, during a contact mechanics test, the substrate contact response depth 26 is known through the core 32, and the engagement load reaction force on the stylus 20 is either controlled or measured. The substrate monitoring device 39 is configured to detect additional parameters of the substrate contact response 12. Computer algorithms may be used to predict the physical properties of the substrate 10 using these measurements. As shown in FIG. 21, the substrate monitoring device 39 may be positioned behind the stylus 20. In other embodiments, the substrate monitoring device 39 may be positioned under the stylus 20, or be coupled to one of the trailing floats 58 of the core 32. The substrate monitoring device may include both contact and non-contact devices.

The pile-up height 28 may be measured directly using at least one optical, electromagnetic, or mechanical method. Optical methods include laser confocal displacement meters, although other suitable methods are possible. The pile-up height 28 may be measured with a contact mechanism or a non-contact mechanism. When detecting the pile-up height 28, the average of the pile-up heights 28 from each side of the substrate contact response 12 may be measured to simplify post-processing methods.

Figure 51:
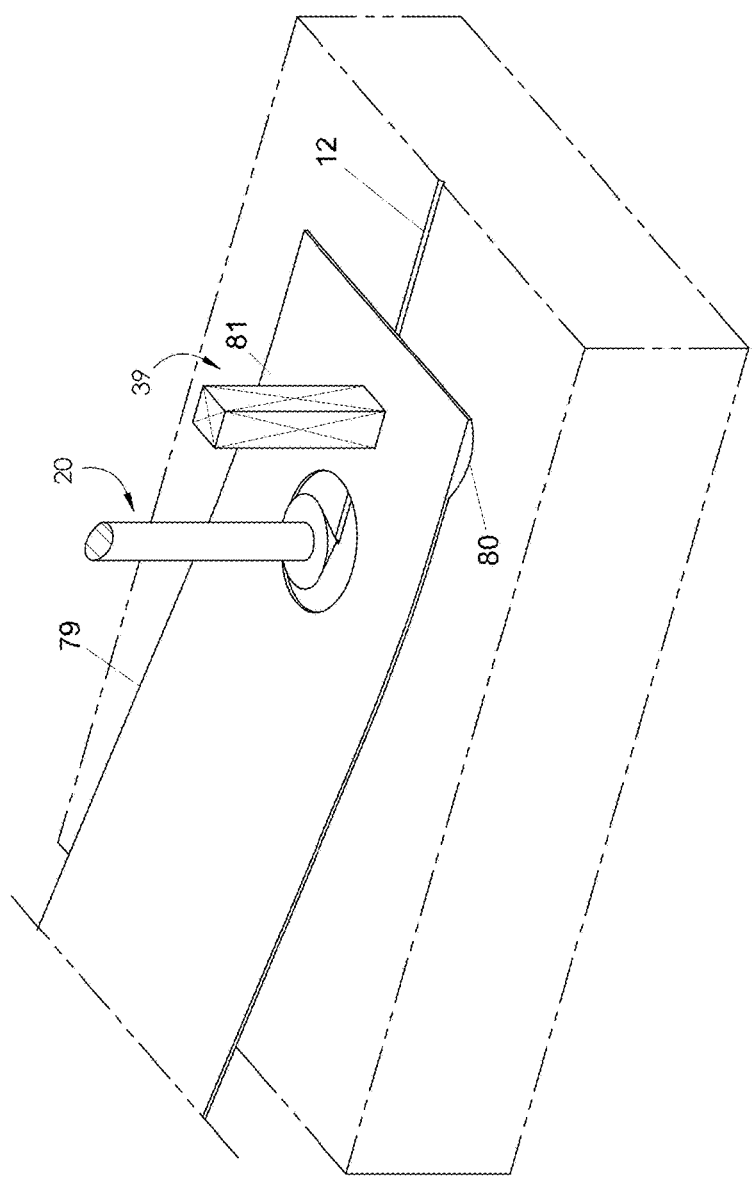
FIG. 51 is a schematic perspective view of an exemplary substrate monitoring device for the testing apparatus of FIG. 1 according to embodiments of the present invention.

Referring to FIG. 51, according to one exemplary embodiment, the substrate monitoring device 39 may include a leaf spring 79. The leaf spring 79 is coupled to the core 32 such that the distal end of the leaf spring 79 is positioned at or below the elevation of the stylus 20. A protrusion 80 (e.g., a wedge or ridge) is provided at the distal end of the leaf spring 79. The protrusion 80 is configured to contact the top of the piles 14 on either side of the substrate contact response 12. The biasing properties of the leaf spring 79 may allow maintaining contact between the protrusion 80 and the piles 14. The contact between the piles 14 and the protrusion 80 deflects the distal end of the leaf spring 79 upward. The magnitude of the deflection of the leaf spring 79 may be detected with a displacement transducer 81 located over the protrusion 80 and used to calculate the pile-up height 28. The transducer 81 may be an LVDT, a plate capacitor, a piezoelectric unit, a laser sensor, an optical focus sensor, or any other suitable device. If included with a core 32 as part of device testing apparatus 30, the profiles for the tracers may span from the front of the device towards the back and across the stylus 20, and may have sufficient compliance to accommodate the entirety of a measurement range.

Figure 52:
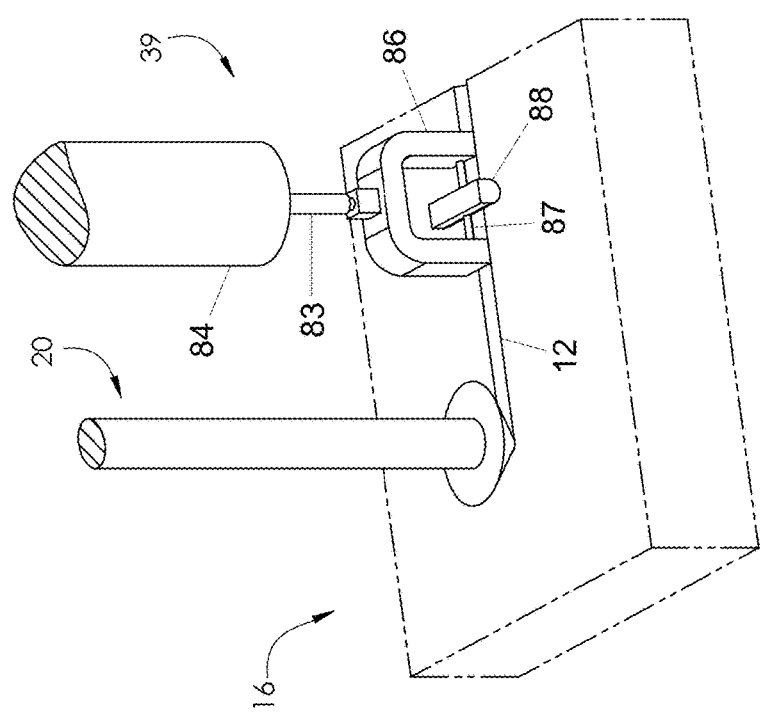
FIG. 52 is a schematic perspective view of an exemplary substrate monitoring device for the testing apparatus of FIG. 1 according to embodiments of the present invention.

Referring to FIG. 52, according to another exemplary embodiment, the substrate monitoring device 39 may include a transducer 84 coupled to the core 32 in a generally vertical orientation. A mount 86 is disposed below the transducer 84, proximate to the substrate surface 16, and is coupled to the transducer 84 via a connection rod 83. A wedge beam 88 is coupled to the mount 86 on a freely rotating pin 87, the pin being oriented generally in line with the trajectory of the stylus 20 and the wedge beam 88 being transverse to the trajectory of the stylus 20 and extending across the contact width of the substrate contact response 12 such that it contacts the piles 14 on either side of the substrate contact response 12. The magnitude of the deflection of the mount 86 may be detected with the transducer 84 and used to calculate the pile-up height 28. The transducer 84 may be an LVDT, a plate capacitor, a piezoelectric unit, a laser sensor, an optical focus sensor, or any other suitable device.

In another embodiment, the measurement apparatus 39 may instead be configured to measure the contact width 24. The contact width 24 may be measured with profilometry, or by direct imaging with a microscope or magnifying device.

Figure 53:
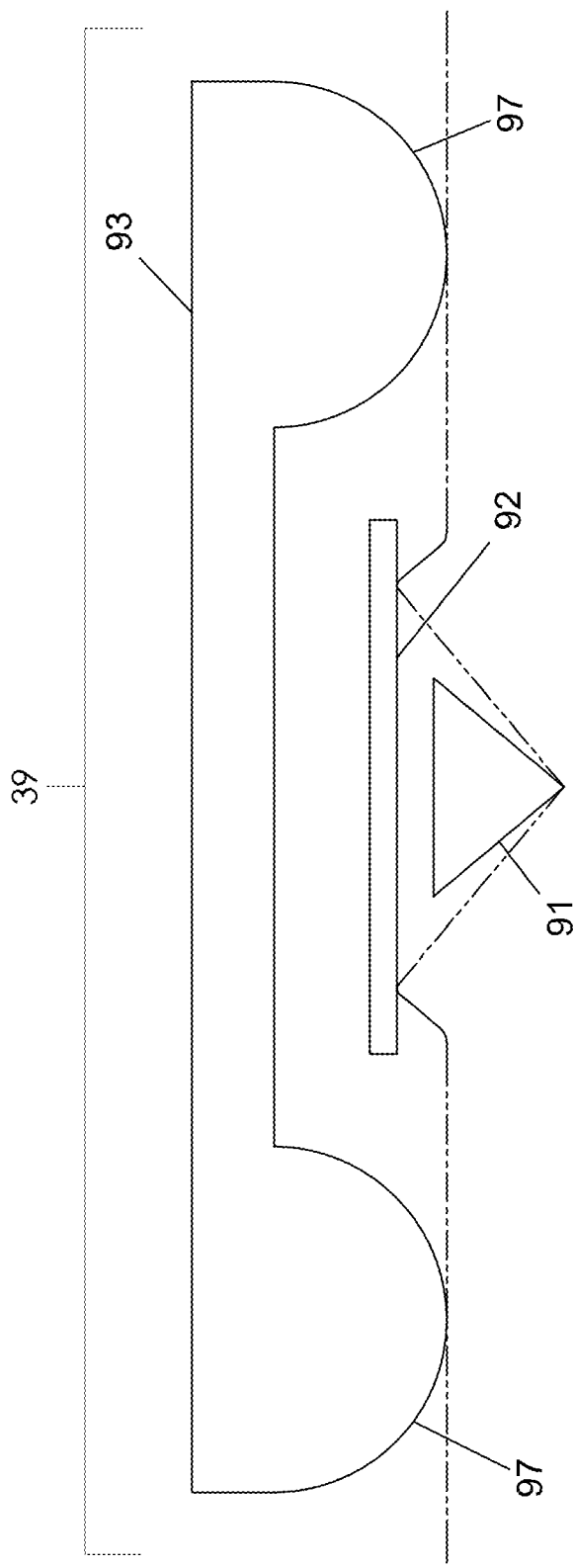
FIG. 53 is a schematic cross-sectional view of an exemplary substrate monitoring device that monitors more than one substrate contact response feature according to embodiments of the present invention.
Figure 54B:
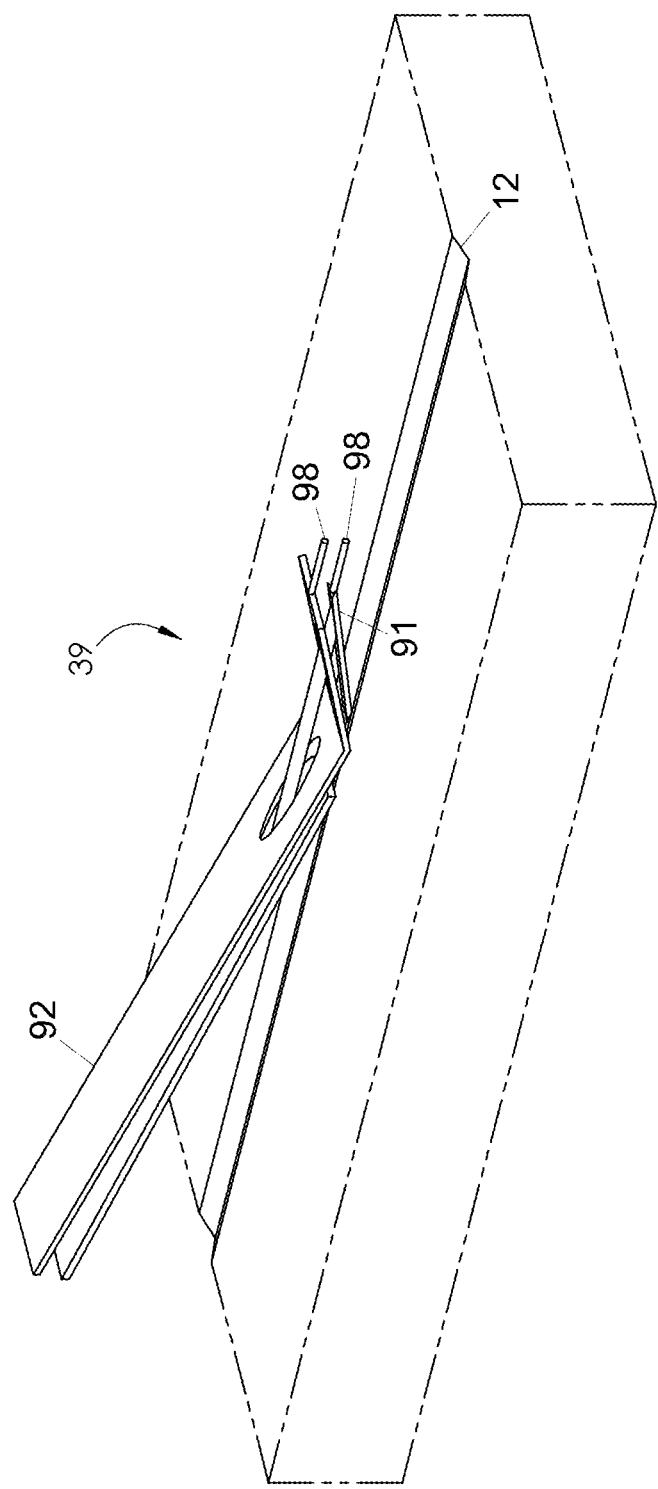
Figure 54C:
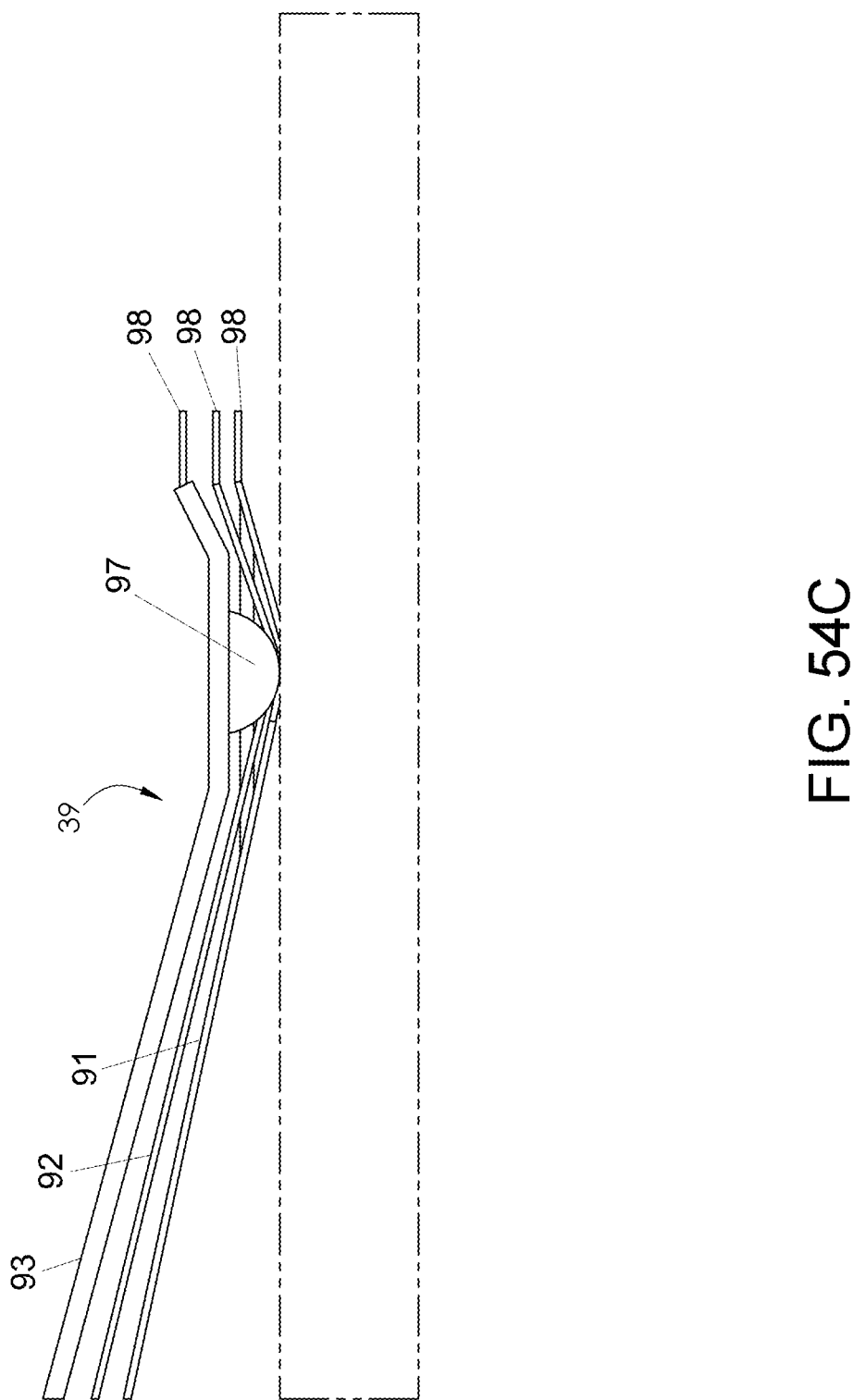
FIGS. 54C and 54D are side view and front view, respectively, of an exemplary substrate monitoring device according to embodiments of the present invention.
Figure 54D:
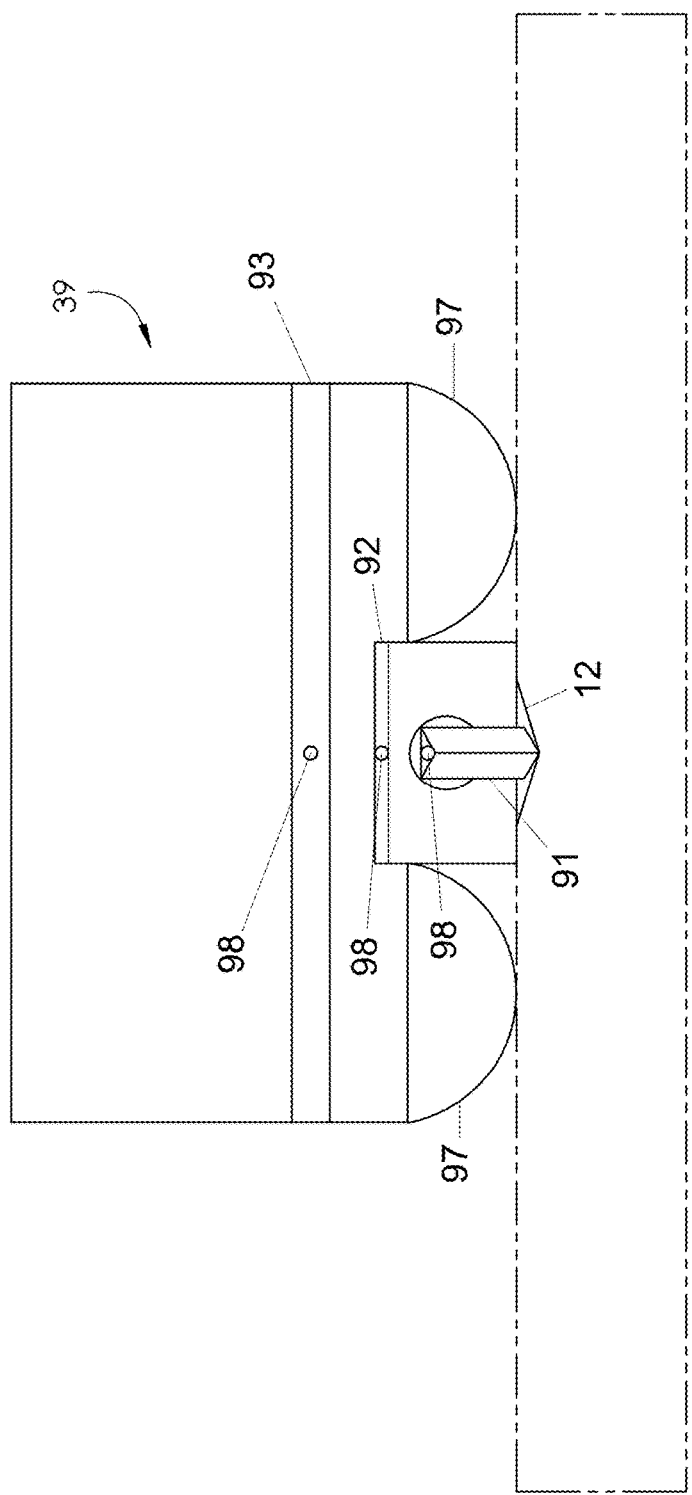
Figure 55A:
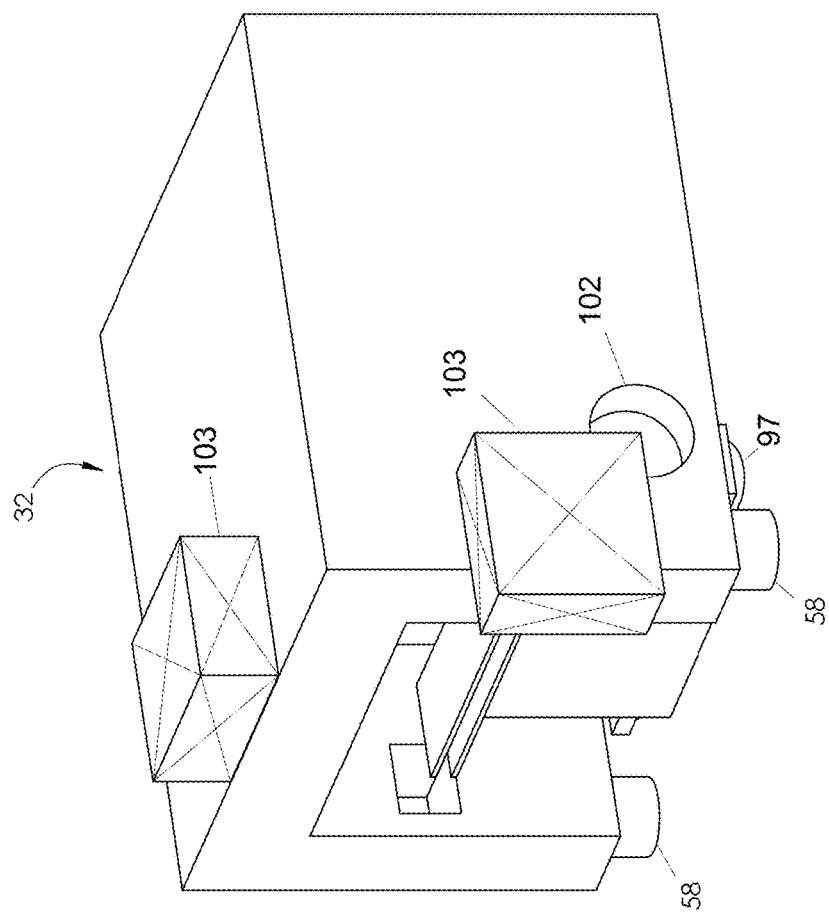
FIGS. 55A-C are schematic perspective view, cross-sectional perspective view, and bottom view, respectively, of an exemplary testing apparatus and substrate monitoring device according to embodiments of the present invention.
Figure 55B:
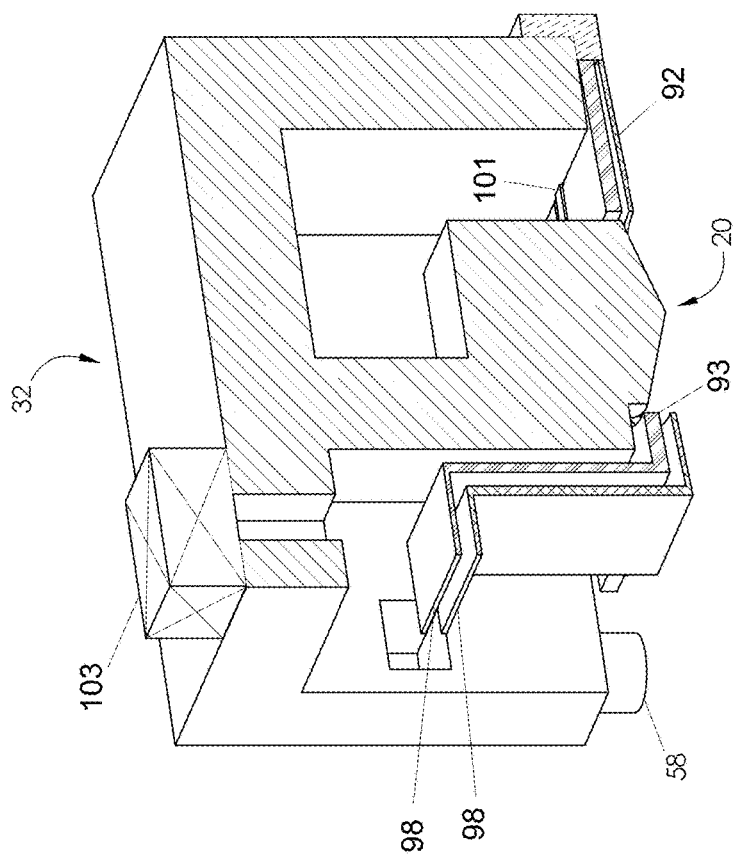
Figure 55C:
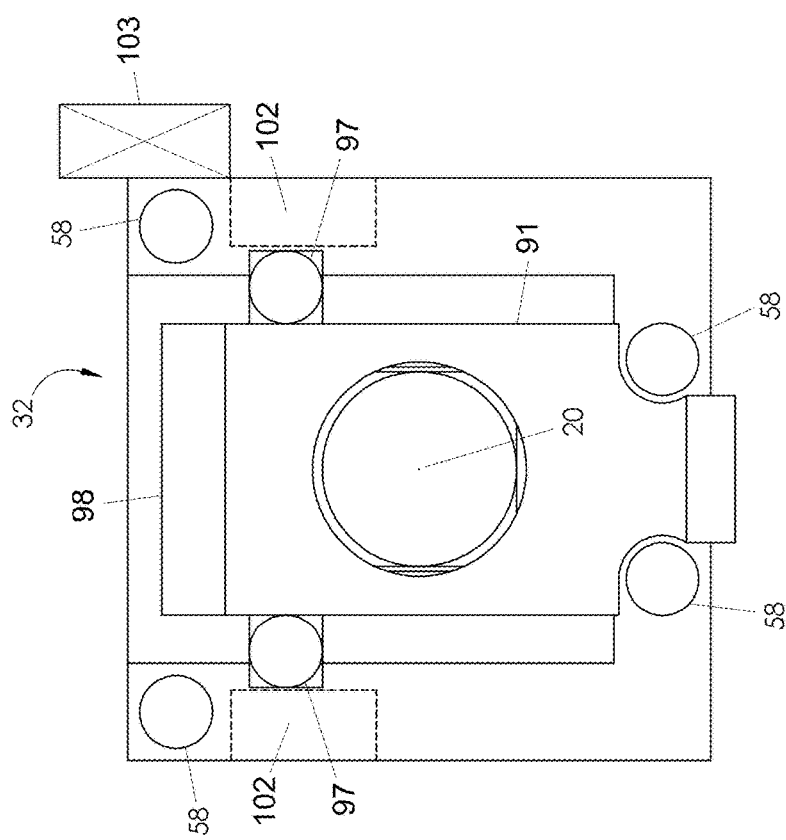

As shown in FIG. 53-54D, a substrate monitoring device 39 allows for monitoring additional information about the substrate contact response 12. According to one embodiment, the substrate monitoring device 39 may include a combination of tracers. The tracers may be separate or combined by branching off from a larger tracer or another apparatus. A deformation center tracer 91 allows for monitoring the substrate contact response depth 26, and the deformation center tracer 91 may have a smaller included angle than the included angle 22 at the center of the substrate contact response, as shown in FIG. 54. The deformation center tracer 91 may also identify and measure surface roughness and local variations caused by pores, inclusions and micromodifications in the material. A pile-up height tracer 92 may be similar to the one shown in FIGS. 54A-B, but is utilized in conjunction with a substrate surface tracer 93. The pile-up height tracer 92 and the substrate surface tracer 93 may be sufficiently compliant under torsion to ensure contact on both sides of the substrate contact response even in the presence of tilt. All tracers may be elastically preloaded to ensure sufficient contact pressure when the testing apparatus engages with the substrate. In addition, the contact pressure may be induced through other mechanisms; e.g., self-weight or air pressure. The pile-up height tracer 92 may have a protrusion 80 for pile-up contact, a pile-up tracer corner 96, or a straight end. The substrate surface tracer 93 may have substrate surface tracer floats 97, a straight end, or both.

The tracers, which are a part of the profile monitoring apparatus 90, may be monitored through electronic, optical, mechanical and other like methods. Electrical methods may include monitoring capacitance, inductance, piezo-electric properties, or any combination of the like. Optical methods may include confocal and optical micrometry with the light source illuminating from any suitable direction, e.g., from the top or side. Mechanical methods may include the use of an LVDT or other displacement transducers. According to one embodiment, the instrumentation may be mounted to the substrate surface tracer 93. An additional embodiment includes a tracer extension 98 for use with optical methods. Tracer extensions 98 may be mounted to the deformation center tracer 91, the pile-up height tracer 92, the substrate surface tracer 93, or any combination of these to be used as reference point for monitoring and each respective profile property. Alternatively, the end of the tracers may be flat, to be used with, for example, optical methods such as with the use of confocal lenses.

As an alternative to the profile monitoring apparatus 90, a 2D profilometer, either contact-based or optical, may be mounted to the testing apparatus 30 behind the stylus 20. The 2D profilometer may allow for a full description of the substrate contact response. In addition, a laser confocal displacement sensor, or similar residual substrate measurement device 39, may be utilized to obtain a complete description of the substrate contact response 12.

Electronic Controls

In one embodiment, the test apparatus is configured with an electronic control system which may automate the motion of moving components of the test apparatus. The electronic controls may monitor motions of devices or test processes using electronic sensors and manage or direct their respective response. For example, the motion of the core may be monitored via position sensors and directed via the electronic controls, or the motion of the stylus may be monitored via a load cell and the electronic controls send commands to an actuator to maintain the desired tip force.

Substrate Surface Preparation

Figure 56A:
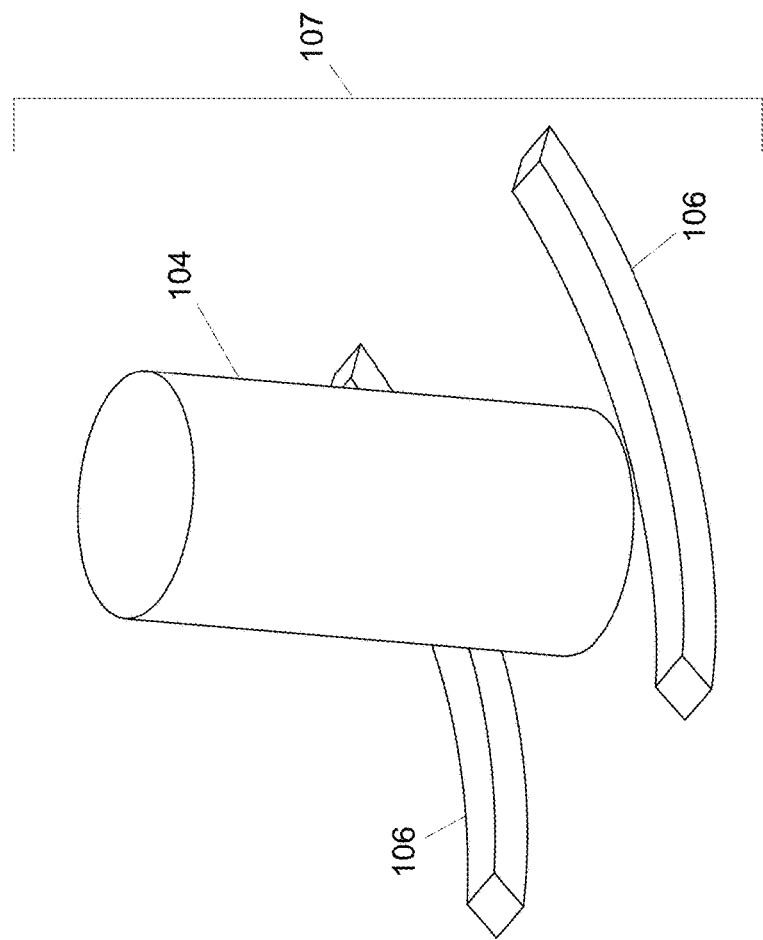

FIGS. 56A-B show an embodiment of an apparatus utilizing a substrate surface preparation device 107. Surface preparation may be utilized prior to performing a contact mechanics test, or subsequent to conducting a test to remove the deformation 11 from the substrate surface 16. The apparatus may include a surfacing tool 104 mounted with or without a substrate surfacing tool tilt 105 to engage the substrate as guided by a surfacing referencing device 106. The surfacing referencing device 106 may include a guiding tool 108 set having a set curvature. The substrate surface preparation device 107 may introduce a predetermined curvature to the substrate surface, which may also be corrected for by the alignment mechanism 40. For example, a material sample curvature introduced by the substrate surface preparation device 107 may be corrected for by actuating floats 58.

In one application, the substrate surface preparation allows for smooth transitions from the substrate to a weld. The substrate surface preparation device 107 may be based on abrasive techniques or machining, e.g., such as end milling. The detail of the surfacing tool 109 and the curvature of the surfacing referencing device 106 may be employed as an input to adjust the ratio of the span between the stylus 20 and the front floats 58 to the span between the stylus 20 and the rear floats 58.

Substrate surface preparation is optional. In general, any type of processing to precondition the substrate surface 16 may be considered substrate surface preparation. In one embodiment, a surface preparation device allows for verifying and/or improving at least one condition of the material substrate surface 12 before a contact mechanics test is performed. According to one embodiment, the substrate surface may be lubricated to reduce the friction of the substrate surface and/or the variation of the friction of the substrate surface. According to some embodiments, sample surface rehabilitation is used to remove the deformation and changes on or beneath the substrate surface. This includes grinding, sand-blasting or polishing. It also includes sample surface rehabilitation devices based on machining processes similar to those that can be used for automated surface preparation that can be integrated with the main apparatus or used sequentially.

Multiple Apparatuses

The embodiments of the testing apparatus discussed above may be utilized as part of an assembly of multiple devices. These devices may be linked in series or parallel, and contain cores containing one or more styluses, various styluses, or various substrate monitoring device to measure various characteristics of the deformation imposed in a substrate through contact mechanics tests. The assembly of devices may be driven by one or more core engagement mechanisms. In another embodiment, a variety of testing apparatuses 30 may be provided, each having a different relative height between the floats 58 and the stylus 20.

Fillet Welds

The testing apparatus 30 may be employed for the characterization of surfaces up to the toe of and through fillet welds and groove welds. For such an application, the floats 58 may be located behind the stylus 20. According to one embodiment, two floats 58 may be located behind the stylus 20. This arrangement allows the stylus 20 to approach a sloped portion of the weld. In some cases, two operations may be utilized to obtain the substrate contact response information up to the end of the trajectory of the stylus 20 when the floats 58 are located behind the stylus 20. A first operation includes the formation of a deformation utilizing an alignment device 40, and a second operation may include measuring the substrate contact response using an alignment mechanism 40. Transverse markers may be added on the substrate surface 16 prior to forming a deformation to establish a relationship between the engagement load reaction force and the substrate contact response. To combine the two operations, the residual substrate measurement device 39 may be mounted opposite to the orientation shown in FIGS. 51-54D. For example, the substrate monitoring device 39 may be attached at the rear of the testing apparatus 30 and the interaction with the substrate contact response may be just behind the stylus 20.

Computer System

The testing apparatus 30 may be connected to, or include, an analysis system that is configured to predict or estimate the physical properties of the substrate 10 based on the measured data produced during the contact mechanics test. The analysis system may be a computing device. According to one embodiment, the testing apparatus 30 may be connected to an analysis system by a wired connection, wireless connection, a USB connection, or any other connection or combination of connection types.

SUMMARY

The testing apparatus 30 as described above provides a simple to implement and reliable method of performing a contact mechanics test to determine mechanical properties of a substrate 10. The testing apparatus 30 is capable of performing a contact mechanics test and monitoring the inputs needed to predict mechanical properties. Further, through the use of an alignment mechanism 40, the testing apparatus 30 may maintain a prescribed stylus orientation with respect to the surface throughout a contact mechanics test. The alignment mechanism 40 may also be utilized to monitor the undeformed substrate surface or control the local angular orientation of the stylus 20 through multiple methods. The testing apparatus 30 may control the engagement and sliding loads to accurately control the substrate contact response depth 26 during a contact mechanics test.

The testing apparatus 30 as described above is a relatively compact mechanism that is suitable for attachment to both portable and stationary implementations. This would allow for in situ testing of larger structures in a field environment with a portable device, as well as laboratory testing of smaller samples with a stationary device. The testing apparatus 30 can have a core engagement mechanism 39 capable of operating in either a push configuration or a pull configuration, and may be utilized with multiple core engagement mechanisms 39 based on the desired deformation, engagement load, sliding load, and substrate geometry.

The testing apparatus 30 described herein is able to continuously monitor the engagement load reaction force at the stylus 20 during a contact mechanics test. The testing apparatus 30 includes instrumentation to continuously measure the substrate contact response along the length of the deformation using both contact and non-contact methods.

A novel method is provided to obtain the material substrate response at different locations on the sample surface using a prescribed stylus alignment with respect to the sample surface. A novel method is also provided to infer about the property gradient and effective properties of the substrate.

Although the description contains the above specificities, these should not be construed as limiting the scope of the invention, but as merely providing illustrations of some of the presently preferred embodiments of this invention. For example, the testing apparatus described may be incorporated within a continuous quality control system where deformations are used to monitor changes in material properties throughout production, such as a metal fabrication shop or automotive manufacturer. It should be noted that any of the components of the testing apparatuses described herein, or any of the steps of the testing methods described herein using the testing apparatuses described herein, may be operated manually or by a computing device. The operation by a computer device may, for example, be carried out through the execution of the computing device by an algorithm (such as through a computer program). Similarly, the algorithms described herein may be computer algorithms stored as software on a non-transitory computer-readable medium. A computing device may refer to any device that comprises a processor. In addition, the testing apparatus may be manufactured from a variety of materials including aluminum and brass, with various polymer covers to house the important instrumented components. The alignment mechanism and associated mounting components may be made smaller or larger based on the desired substrate contact response, engagement load, sliding load and substrate geometry. The core engagement mechanism may exist in many different embodiments such that it may be attached to portable or stationary systems. The testing apparatus described herein may be packaged as modular units to offer specific features such as enhanced measurement resolution or different deformation properties. According to one embodiment, the substrate contact response parameters may be monitored by an independent substrate monitoring device that is located behind, and follows, the stylus. Also, the testing apparatus may include an optional substrate surface preparation device which provides substrate surface preparation by milling, grinding, polishing or the like. Other embodiments include configurations specific to creating or measuring deformations specific to applications referenced above, including the parameters necessary to generate an uniaxial stress-strain curve and measure existing service loads. These embodiments may be linked together through a variety of means to perform multiple contact mechanics tests simultaneously or sequentially. Additionally, the methods described herein may further include using equations derived from a computer simulation, such as finite element analysis, to establish predictors for the yield strength, the strain hardening exponent, the ultimate tensile strength, and/or an index of the elongation at break. Other analytical methods, such as analytical algorithms, may be employed to derive material property parameters.

The above-described embodiments of the invention may be implemented in any of numerous ways. For example, some embodiments may be implemented using hardware, software or a combination thereof. When any aspect of an embodiment is implemented at least in part in software, the software code may be executed on any suitable processor or collection of processors, whether provided in a single computer or distributed among multiple computers.

In this respect, various aspects of the invention may be embodied at least in part as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various embodiments of the technology discussed above. The computer readable medium or media may be transportable, such that the program or programs stored thereon may be loaded onto one or more different computers or other processors to implement various aspects of the present technology as discussed above.

The terms "program" or "software" are used herein in a generic sense to refer to any type of computer code or set of computer-executable instructions that may be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Although the above discussion discloses various exemplary embodiments of the invention, it should be apparent that those skilled in the art may make various modifications that will achieve some of the advantages of the invention without departing from the true scope of the invention.

What is claimed is:

1. An apparatus for performing a contact mechanics test on a substrate, the apparatus comprising:
   (i) a stylus having a principal axis and shaped to deform the substrate;
   (ii) a core, in which the stylus is hosted, configured to engage the stylus against the substrate;
   (iii) a topographic probe, coupled to the core, configured to gather substrate surface elevation or surface topographic measurements as scanning referencing before or during the contact mechanics test;
   (iv) a stylus alignment mechanism, coupled to the core, configured to utilize the surface topographic measurements to induce a desired orientation between the stylus and a surface of the substrate;
   (v) a stylus engagement mechanism, coupled to the core or the stylus, configured to induce a contact load between the stylus and the substrate surface;
   (vi) an engagement mechanism, coupled to the core or to the stylus alignment mechanism, configured to induce an in-plane relative displacement between the stylus and the substrate surface, wherein the engagement mechanism is a frame engagement mechanism and/or a core engagement mechanism; and
   (vii) a substrate monitoring device, coupled to the core, configured to measure characteristics of substrate contact response, collect material machined from the substrate, or both.

2. The apparatus of claim 1, wherein one or more coupled components are contiguous, wherein the coupled components include:
   (i) the topographic probe coupled to the core;
   (ii) the stylus alignment mechanism coupled to the core;
   (iii) the stylus engagement mechanism coupled to the core or the stylus;
   (iv) the engagement mechanism coupled to the core or the stylus alignment mechanism and/or;
   (v) the substrate monitoring device coupled to the core.

3. The apparatus of claim 1, wherein the contact mechanics test is a frictional sliding test and the apparatus is configured to perform the frictional sliding test on the substrate surface.

4. The apparatus of claim 1, wherein the contact mechanics test is a series of indentation tests and the apparatus is configured to perform the series of indentation tests on the substrate surface.

5. The apparatus of claim 1, wherein the stylus alignment mechanism is configured to adjust for position and contour of the substrate surface through control of the local angular orientation of the stylus with respect to the substrate surface to perform scanning referencing.

6. The apparatus of claim 1, wherein the stylus alignment mechanism is configured to adjust for position and contour of the substrate surface through articulation of the substrate with respect to the stylus to perform scanning referencing using information from the topographic probe.

7. The apparatus of claim 1, wherein the core is configured to host two or more styluses in parallel or in sequence to perform two or more contact mechanics tests in parallel or in series.

8. The apparatus of claim 1, wherein the stylus is manufactured from a spherical ball bearing.

9. The apparatus of claim 1, wherein one or more wedge-shaped styluses are used to generate a substrate contact response, including micromodifications on or beneath the sample surface.

10. A method for performing a contact mechanics test on a substrate, the method comprising:
    (i) providing the apparatus of claim 1;
    (ii) maintaining the principal axis of the stylus at a desired local angular orientation with respect to the substrate surface;
    (iii) causing the stylus to engage and deform the substrate;
    (iv) re-aligning the stylus as or after the stylus engages the substrate; and
    (v) measuring a substrate contact response.

11. The method of claim 10, further comprising preparing the substrate surface prior to causing the stylus to engage the substrate.

12. The method of claim 10, further comprising rehabilitating the substrate surface subsequent to measuring the substrate contact response.

13. The method of claim 10, further comprising measuring the thickness of the substrate before and after preparing the substrate surface and/or before or after the contact mechanics test.

14. The method of claim 10, further performing the contact mechanic test in more than one direction and orientation with respect to the sample surface.

15. The method of claim 10, further performing two or more contact mechanics tests performed in series or parallel while utilizing different stylus geometries to induce different effective strains within the substrate.

16. The method of claim 10, further comprising measuring the substrate contact response at multiple times to quantify rate-dependent and time-dependent strain release through viscoelastic and viscoplastic relaxation.

17. The apparatus of claim 1, further including an alignment mechanism for the core or the stylus, and the topographic probe is configured to collect relative elevation that provides input to the alignment mechanism.

18. The apparatus of claim 1, wherein the stylus alignment mechanism is a substrate alignment stage in which the substrate is mounted.

19. The apparatus of claim 18, wherein the substrate alignment stage further comprises an electronic gimbal with rotational actuators.

20. The apparatus of claim 18, wherein the substrate alignment stage further comprises three translational actuators with multi-axial attachments.

21. The apparatus of claim 18, wherein the substrate alignment stage further comprises two translational actuators and a fixed multi-axial attachment.

22. The apparatus of claim 18, wherein the engagement mechanism is part of the substrate alignment stage.

23. The apparatus of claim 1, further comprising a stylus load transfer mechanism, coupling the stylus engagement mechanism and the stylus, configured to transfer the contact load to the stylus.

24. The apparatus of claim 23, wherein the stylus load transfer mechanism is a lever arm situated perpendicular to a direction of movement of the stylus during the contact mechanics test.

25. The apparatus of claim 1, further comprising:

two or more styluses, each having a respective principal axis and shaped to deform the substrate and each having a respective stylus engagement mechanism; and two or more stylus load transfer mechanisms, each stylus engagement mechanism and stylus load transfer mechanism coupled to one stylus and configured to be implemented simultaneously with each other.

* * * * *